(12) United States Patent
Sack et al.

(10) Patent No.: US 10,765,526 B2
(45) Date of Patent: Sep. 8, 2020

(54) DISK FUSION IMPLANT

(71) Applicant: JMEA Corporation, Rockville, MD (US)

(72) Inventors: James A. Sack, Elverson, PA (US); Mohit K. Bhatnagar, Potomac, MD (US); Jack Y. Yeh, North Potomac, MD (US)

(73) Assignee: JMEA Corporation, Rockville, MD (US)

( * ) Notice: Subject to any disclaimer, the term of this patent is extended or adjusted under 35 U.S.C. 154(b) by 211 days.

(21) Appl. No.: 16/055,398

(22) Filed: Aug. 6, 2018

(65) Prior Publication Data
US 2019/0029840 A1   Jan. 31, 2019

Related U.S. Application Data

(63) Continuation of application No. 14/191,954, filed on Feb. 27, 2014, now Pat. No. 10,039,647, which is a
(Continued)

(51) Int. Cl.
*A61F 2/44* (2006.01)
*A61F 2/46* (2006.01)
*A61F 2/30* (2006.01)

(52) U.S. Cl.
CPC ............ *A61F 2/442* (2013.01); *A61F 2/4611* (2013.01); *A61F 2/4425* (2013.01); *A61F 2002/30014* (2013.01); *A61F 2002/30092* (2013.01); *A61F 2002/30133* (2013.01); *A61F 2002/30136* (2013.01); *A61F 2002/30291* (2013.01);
(Continued)

(58) Field of Classification Search
CPC ............ A61B 17/7094; A61B 17/7098; A61B 17/885; A61B 17/8852; A61B 17/8858; A61F 2/442; A61F 2/4455; A61F 2/4465; A61F 2/46; A61F 2/4611; A61F 2/4425; A61F 2002/4415; A61F 2002/4435; A61F 2002/444; A61F 2002/302; A61F 2002/4475; A61F 2002/448; A61F 2002/4485; A61F 2002/449; A61F 2002/4631; A61F 2002/4635; A61F 2002/4687; A61F 2002/4615
See application file for complete search history.

(56) References Cited

U.S. PATENT DOCUMENTS 3,741,205 A   6/1973   Markolf et al.
4,407,006 A   9/1983   Holick et al.
(Continued)

FOREIGN PATENT DOCUMENTS

FR   2712486   5/1995

OTHER PUBLICATIONS

International Search Report and Written Opinion, dated Aug. 12, 2009, from PCT Application No. PCT/US2008/069141.
(Continued)

*Primary Examiner* — Kevin T Truong
*Assistant Examiner* — Tracy L Kamikawa
(74) *Attorney, Agent, or Firm* — Piumsea Law Group, LLC

(57) ABSTRACT

An implant strip is disclosed. In some cases, the prosthesis can take the form of an implant strip that may be implanted through the use of a surgical procedure that minimizes incision sizes and may be considered less invasive than typical spinal implant procedures. The implant strip includes provisions for implantation, including teeth, spacing provisions, and various shapes.

20 Claims, 38 Drawing Sheets

Related U.S. Application Data continuation of application No. 13/463,041, filed on May 3, 2012, now Pat. No. 8,696,753, which is a continuation of application No. 12/118,503, filed on May 9, 2008, now Pat. No. 8,197,548, which is a continuation-in-part of application No. 11/774,584, filed on Jul. 7, 2007, now Pat. No. 7,922,767.

(52) U.S. Cl.
CPC ............ *A61F 2002/30563* (2013.01); *A61F 2002/30571* (2013.01); *A61F 2002/30594* (2013.01); *A61F 2002/30787* (2013.01); *A61F 2002/30841* (2013.01); *A61F 2002/30904* (2013.01); *A61F 2002/30971* (2013.01); *A61F 2002/444* (2013.01); *A61F 2002/448* (2013.01); *A61F 2002/4415* (2013.01); *A61F 2210/0014* (2013.01); *A61F 2230/0004* (2013.01); *A61F 2230/0015* (2013.01); *A61F 2230/0091* (2013.01); *A61F 2250/0018* (2013.01); *A61F 2310/00017* (2013.01); *A61F 2310/00023* (2013.01); *A61F 2310/00029* (2013.01); *A61F 2310/00179* (2013.01); *A61F 2310/00976* (2013.01)

(56) References Cited

U.S. PATENT DOCUMENTS

| | | |
|---|---|---|
| 4,834,757 A | 5/1989 | Brantigan |
| 5,171,280 A | 12/1992 | Baumgartner |
| 5,190,545 A | 3/1993 | Corsi et al. |
| 5,306,310 A | 4/1994 | Siebels |
| 5,405,391 A | 4/1995 | Henderson et al. |
| 5,423,826 A | 6/1995 | Coates et al. |
| 5,439,464 A | 8/1995 | Shapiro |
| 5,514,181 A | 5/1996 | Light et al. |
| 5,545,165 A | 8/1996 | Biedermann et al. |
| 5,595,621 A | 1/1997 | Light et al. |
| 5,676,667 A | 10/1997 | Hausman |
| 5,676,702 A | 10/1997 | Ratron |
| 5,902,231 A | 5/1999 | Foley et al. |
| 5,919,235 A | 7/1999 | Husson et al. |
| 5,976,146 A | 11/1999 | Ogawa et al. |
| 6,264,656 B1 | 7/2001 | Michelson |
| 6,273,889 B1 | 8/2001 | Richelsoph |
| 6,371,968 B1 | 4/2002 | Kogasaka et al. |
| 6,432,106 B1 | 8/2002 | Fraser |
| 6,436,103 B1 | 8/2002 | Suddaby |
| 6,447,512 B1 | 9/2002 | Landry et al. |
| 6,488,710 B2 | 12/2002 | Besselink |
| 6,524,312 B2 | 2/2003 | Landry et al. |
| 6,530,926 B1 | 3/2003 | Davison |
| 6,533,790 B1 | 3/2003 | Liu |
| 6,565,571 B1 | 5/2003 | Jackowski et al. |
| 6,610,094 B2 | 8/2003 | Husson |
| 6,616,671 B2 | 9/2003 | Landry et al. |
| 6,620,196 B1 | 9/2003 | Trieu |
| 6,656,178 B1 | 12/2003 | Veldhuizen et al. |
| 6,660,037 B1 | 12/2003 | Husson et al. |
| 6,800,084 B2 | 10/2004 | Davison et al. |
| 6,811,558 B2 | 11/2004 | Davison et al. |
| 6,913,622 B2 | 7/2005 | Gjunter |
| 7,569,233 B2 | 8/2009 | Malaviya et al. |
| 7,799,089 B2 | 9/2010 | Plouhar et al. |
| 7,901,460 B2 | 3/2011 | Sherman |
| 7,922,767 B2 | 4/2011 | Sack et al. |
| 8,197,548 B2 | 6/2012 | Sack et al. |
| 8,241,357 B2 | 8/2012 | Bhatnagar et al. |
| 8,257,395 B2 | 9/2012 | Bhatnagar et al. |
| 8,518,117 B2 | 8/2013 | Sack et al. |
| 8,518,118 B2 | 8/2013 | Sack et al. |
| 8,696,753 B2 | 4/2014 | Sack et al. |
| 10,039,647 B2 | 8/2018 | Sack et al. |
| 2002/0107573 A1 | 8/2002 | Steinberg |
| 2002/0198533 A1 | 12/2002 | Geisler et al. |
| 2003/0018390 A1 | 1/2003 | Husson |
| 2003/0073998 A1 | 4/2003 | Pagliuca et al. |
| 2003/0135216 A1 | 7/2003 | Sevrain |
| 2003/0171753 A1 | 9/2003 | Collins et al. |
| 2003/0175075 A1 | 9/2003 | Garrison |
| 2003/0225409 A1 | 12/2003 | Freid et al. |
| 2004/0034351 A1 | 2/2004 | Sherman et al. |
| 2004/0059431 A1 | 3/2004 | Plouhar et al. |
| 2004/0082960 A1 | 4/2004 | Davison |
| 2004/0106924 A1 | 6/2004 | Ralph et al. |
| 2004/0116931 A1 | 6/2004 | Carlson |
| 2004/0127902 A1 | 7/2004 | Suzuki et al. |
| 2004/0176842 A1 | 9/2004 | Middleton |
| 2004/0186482 A1 | 9/2004 | Kolb et al. |
| 2004/0204716 A1 | 10/2004 | Fanger et al. |
| 2004/0204717 A1 | 10/2004 | Fanger et al. |
| 2004/0215199 A1 | 10/2004 | Zinkel |
| 2004/0215341 A1 | 10/2004 | Sybert et al. |
| 2004/0220669 A1 | 11/2004 | Studer |
| 2004/0230309 A1 | 11/2004 | Dimauro et al. |
| 2004/0249459 A1 | 12/2004 | Ferree |
| 2004/0253185 A1 | 12/2004 | Herweck et al. |
| 2005/0004573 A1 | 1/2005 | Abdou |
| 2005/0015088 A1 | 1/2005 | Ringeisen |
| 2005/0043801 A1 | 2/2005 | Trieu et al. |
| 2005/0090822 A1 | 4/2005 | DiPoto |
| 2005/0119750 A1 | 6/2005 | Studer |
| 2005/0171610 A1 | 8/2005 | Humphreys et al. |
| 2006/0041313 A1 | 2/2006 | Allard et al. |
| 2006/0111715 A1 | 5/2006 | Jackson |
| 2006/0142858 A1 | 6/2006 | Colleran et al. |
| 2006/0149279 A1 | 7/2006 | Mathews |
| 2006/0229615 A1 | 10/2006 | Abdou |
| 2006/0264948 A1 | 11/2006 | Williams |
| 2007/0010826 A1 | 1/2007 | Rhoda et al. |
| 2007/0093906 A1 | 4/2007 | Hudgins et al. |
| 2007/0123986 A1 | 5/2007 | Schaller |
| 2007/0129811 A1 | 6/2007 | Plouhar et al. |
| 2007/0150064 A1 | 6/2007 | Ruberte et al. |
| 2007/0233071 A1 | 10/2007 | Dewey et al. |
| 2007/0270812 A1 | 11/2007 | Peckham |
| 2007/0270858 A1 | 11/2007 | Trieu et al. |
| 2008/0058952 A1 | 3/2008 | Trieu et al. |
| 2008/0133012 A1 | 6/2008 | McGuckin |
| 2008/0140199 A1 | 6/2008 | Briest |
| 2008/0255664 A1 | 10/2008 | Hogendijk et al. |
| 2008/0269893 A1 | 10/2008 | Bhatnagar et al. |
| 2009/0012617 A1 | 1/2009 | White et al. |
| 2009/0012621 A1 | 1/2009 | Sack et al. |
| 2009/0012622 A1 | 1/2009 | Sack et al. |
| 2009/0012623 A1 | 1/2009 | Sack et al. |
| 2009/0048675 A1 | 2/2009 | Bhatnagar et al. |
| 2009/0082810 A1 | 3/2009 | Bhatnagar et al. |
| 2010/0016967 A1 | 1/2010 | Weiss et al. |
| 2010/0310623 A1 | 12/2010 | Laurencin et al. |
| 2012/0165944 A1 | 6/2012 | McGuckin, Jr. |
| 2012/0269873 A1 | 10/2012 | Kerr et al. |
| 2013/0035762 A1 | 2/2013 | Siegal et al. |
| 2013/0110232 A1 | 5/2013 | Hupin et al. |
| 2013/0204374 A1 | 8/2013 | Milella, Jr. |

OTHER PUBLICATIONS

Office Action dated Jun. 8, 2009 in U.S. Appl. No. 12/038,613.
Response to Office Action filed Jul. 8, 2009 in U.S. Appl. No. 12/038,613.
Office Action dated Sep. 17, 2009 in U.S. Appl. No. 12/038,613.
Response to Office Action filed Dec. 17, 2009 in U.S. Appl. No. 12/038,613.
Interview Summary dated Dec. 23, 2009 in U.S. Appl. No. 12/038,613.
Final Office Action dated Apr. 2, 2010 in U.S. Appl. No. 12/038,613.
Request for Continued Examination filed Jul. 19, 2010 in U.S. Appl. No. 12/038,613.
Amendment accompanying Request for Continued Examination filed Jul. 19, 2010 in U.S. Appl. No. 12/038,613.

(56) References Cited

OTHER PUBLICATIONS

Office Action dated Nov. 20, 2012 in U.S. Appl. No. 12/038,613.
Response to Office Action filed Feb. 20, 2013 in U.S. Appl. No. 12/038,613.
Interview Summary dated Feb. 20, 2013 in U.S. Appl. No. 12/038,613.
Notice of Allowance dated Apr. 25, 2013 in U.S. Appl. No. 12/038,613.
Office Action dated Jun. 8, 2009 in U.S. Appl. No. 12/038,629.
Response to Office Action filed Jul. 8, 2009 in U.S. Appl. No. 12/038,629.
Office Action dated Sep. 17, 2009 in U.S. Appl. No. 12/038,629.
Response to Office Action filed Dec. 17, 2009 in U.S. Appl. No. 12/038,629.
Interview Summary dated Dec. 23, 2009 in U.S. Appl. No. 12/038,629.
Final Office Action dated Apr. 1, 2010 in U.S. Appl. No. 12/038,629.
Request for Continued Examination filed Jul. 19, 2010 in U.S. Appl. No. 12/038,629.
Amendment accompanying Request for Continued Examination filed Jul. 19, 2010 in U.S. Appl. No. 12/038,629.
Office Action dated Nov. 26, 2012 in U.S. Appl. No. 12/038,629.
Interview Summary dated Feb. 20, 2013 in U.S. Appl. No. 12/038,629.
Response to Office Action filed Feb. 26, 2013 in U.S. Appl. No. 12/038,629.
Notice of Allowance dated Apr. 24, 2013 in U.S. Appl. No. 12/038,629.
Supplementary European Search Report dated Mar. 7, 2012 in European Patent Application No. 08 781 335.8.
Response to Supplementary European Search Report filed Oct. 5, 2012 in European Patent Application No. 08 781 335.8.
Office Action dated Oct. 7, 2014 in European Patent Application No. 08 781 335.8.
Response to Office Action dated Feb. 17, 2015 in European Patent Application No. 08 781 335.8.

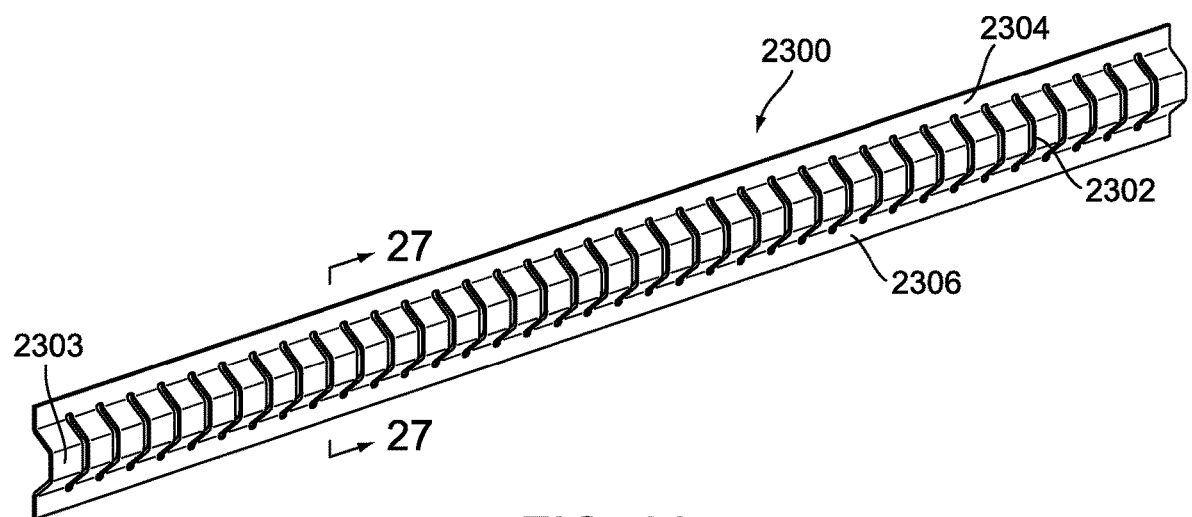
FIG. 26
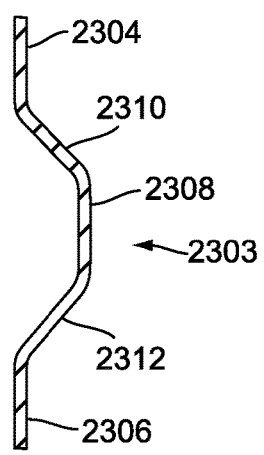 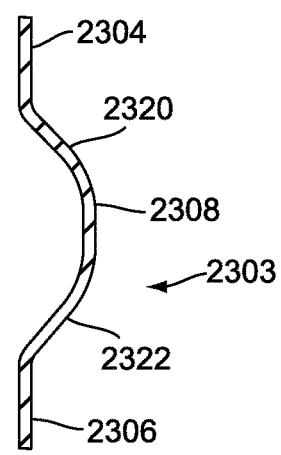
FIG. 27  FIG. 28

DISK FUSION IMPLANT

CROSS REFERENCE TO RELATED APPLICATIONS

This application is a continuation of U.S. Pat. No. 10,039,647, issued Aug. 7, 2018 (U.S. patent application Ser. No. 14/191,954, filed Feb. 27, 2014), which is a continuation of U.S. Pat. No. 8,696,753, issued Apr. 15, 2014 (U.S. patent application Ser. No. 13/463,041, filed May 3, 2012), which is a continuation of U.S. Pat. No. 8,197,548, issued Jun. 12, 2012 (U.S. patent application Ser. No. 12/118,503, filed May 9, 2008), which is a continuation-in-part of U.S. Pat. No. 7,922,767, issued Apr. 12, 2011 (U.S. patent application Ser. No. 11/774,584, filed Jul. 7, 2007), all of which are herein incorporated by reference in their entirety.

BACKGROUND

1. Field

The present invention relates generally to implantable prostheses and in particular to a spinal implant strip including a selectively applied bone growth promoting agent.

2. Description of Related Art

Spinal fusion implants have been previously proposed. In some cases, spinal fusion implants are embedded between adjacent vertebrae, partially or fully replacing the tissue disposed between the vertebrae.

One type of spinal fusion implant is the threaded spinal implant (commonly referred to as a spinal cage). This type of prosthesis is disclosed in Michelson (U.S. Pat. No. 6,264,656), the entirety of which is incorporated by reference. The threaded spinal implant is inserted between two adjacent vertebrae and is incorporated into the fusion of the bone along this portion of the spine.

Brantigan (U.S. Pat. No. 4,834,757) discloses plugs, used as spinal fusion implants, the entirety of which is incorporated by reference. The plugs are rectangular with tapered front ends and tool receiving rear ends. Generally, the plugs may be used in a similar manner to the spinal cages of Michelson. As with the spinal cages, the plugs may be inserted between adjacent vertebrae. The plugs may include nubs that behave like teeth, countering any tendency for the plugs to slip between the vertebrae.

Generally, the spinal fusion implants disclosed require invasive surgery for implantation. Furthermore, these spinal fusion implants rigidly fix two adjacent bones together and do not allow for any motion. There is a need in the art for a type of spinal fusion implant that may be implanted through a minimally invasive procedure. There is also a need for fusion implants that can potentially accommodate motion.

SUMMARY

Modifications for an implant strip for implantation is disclosed. In one aspect, the invention provides a spinal prosthesis, comprising: an implant strip configured for insertion between two vertebrae; the implant strip comprising a first portion having a first axial height and a second portion having a second axial height; and where the first axial height is greater than the second axial height.

In another aspect, the implant strip includes an edge that has a coiled shape selected from the group consisting essentially of a wedge shape, a convex shape, and a concave shape.

In another aspect, the first portion is associated with a crest of the implant strip.

In another aspect, the second portion is associated with a trough of the implant strip.

In another aspect, the second portion is a first end of the implant strip associated with an inner coil.

In another aspect, the first portion is a second end of the implant strip associated with an outer coil.

In another aspect, the first portion is a first end of the implant strip associated with an inner coil.

In another aspect, the second portion is second end portion of the implant strip associated with an outer coil.

In another aspect, the invention provides a spinal prosthesis, comprising: an implant strip configured for insertion between two vertebrae; the implant strip forming a first coil and a second coil; a separating portion disposed the first coil and the second coil; and where the separating portion contacts the first coil and the second coil.

In another aspect, the separating portion comprises a plurality of protrusions on a first surface of the implant strip.

In another aspect, the protrusions are associated with corresponding divots on an opposing second surface of the implant strip.

In another aspect, an opposing second surface of the implant strip is substantially smooth.

In another aspect, the separating portion is a polymer.

In another aspect, the thickness of the polymer varies over the length of the implant strip.

In another aspect, the invention provides a spinal prosthesis, comprising: an implant strip configured for insertion between two vertebrae; the implant strip comprising an edge; and where the edge includes a plurality of teeth.

In another aspect, the edge is an upper edge.

In another aspect, the edge is a lower edge.

In another aspect, a plurality of teeth is disposed on an upper edge and a lower edge.

In another aspect, the teeth have a configuration selected from the group consisting essentially of a saw-toothed shape, a rounded shape, a substantially dull shape, a substantially sharp shape, irregularly spaced teeth, and/or regularly spaced teeth.

In another aspect, the invention provides a spinal prosthesis, comprising: a dual implant strip configured for insertion between two vertebrae, the dual implant strip further comprising a first implant strip and a second implant strip; and a spacer portion is disposed between the first implant strip and the second implant strip and wherein the spacer portion is configured to attach the first implant strip to the second implant strip.

In another aspect, the spacer portion is made of a material different than a material of the first implant strip.

In another aspect, the invention provides a spinal prosthesis, comprising: a layered implant strip configured for insertion between two vertebrae, the layered implant strip further comprising a plurality of implant strips and a plurality of spacer portions; and where a spacer portion from the plurality of spacer portions is disposed between each pair of adjacent implant strips from the plurality of implant strips.

In another aspect, the invention provides a spinal prosthesis, comprising: an implant strip including a first shape and a second shape and wherein the first shape is different than the second shape; the implant strip having the first shape prior to insertion; and where the implant strip transforms from the first shape to the second shape following the application of a signal.

In another aspect, the signal is selected from the group consisting essentially of heat signals, chemical signals, mechanical signals, and electrical signals.

In another aspect, the invention provides a spinal prosthesis configured for insertion between two adjacent vertebrae, a first vertebrae and a second vertebrae, comprising: an implant strip including a lateral dimension extending from a first lateral side portion to a second lateral portion, and wherein the implant strip includes a longitudinal dimension extending down the length of the implant strip; and where the first lateral side of the implant strip is configured to engage the first vertebrae and wherein the second lateral side of the implant strip is configured to engage the second vertebrae; the implant strip having a pre-formed shape comprising a first longitudinal portion of the implant strip forming a first inner coil and a second longitudinal portion of the implant strip forming a second outer coil; and where the implant strip has the pre-formed shape prior to implantation.

In another aspect, the implant strip includes n coils and wherein n can be any real number greater than 1.

Other systems, methods, features, and advantages of the invention will be, or will become, apparent to one of ordinary skill in the art upon examination of the following figures and detailed description. It is intended that all such additional systems, methods, features and advantages be included within this description and this summary, be within the scope of the invention, and be protected by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like reference numerals designate corresponding parts throughout the different views.

FIG. 5-1 is a cross sectional view of a preferred embodiment of an implant strip with a bone growth promoting agent applied to the surface;

FIG. 5-2 is a cross sectional view of a preferred embodiment of an implant strip with a bone growth promoting agent that is selectively applied to the surface;

FIG. 26 is an isometric view of a preferred embodiment of an implant strip with slots;

FIG. 27 is a cross sectional view of a preferred embodiment of an implant strip with slots;

FIG. 28 is a cross sectional view of a preferred embodiment of an implant strip with slots;

DETAILED DESCRIPTION

Figure 1:
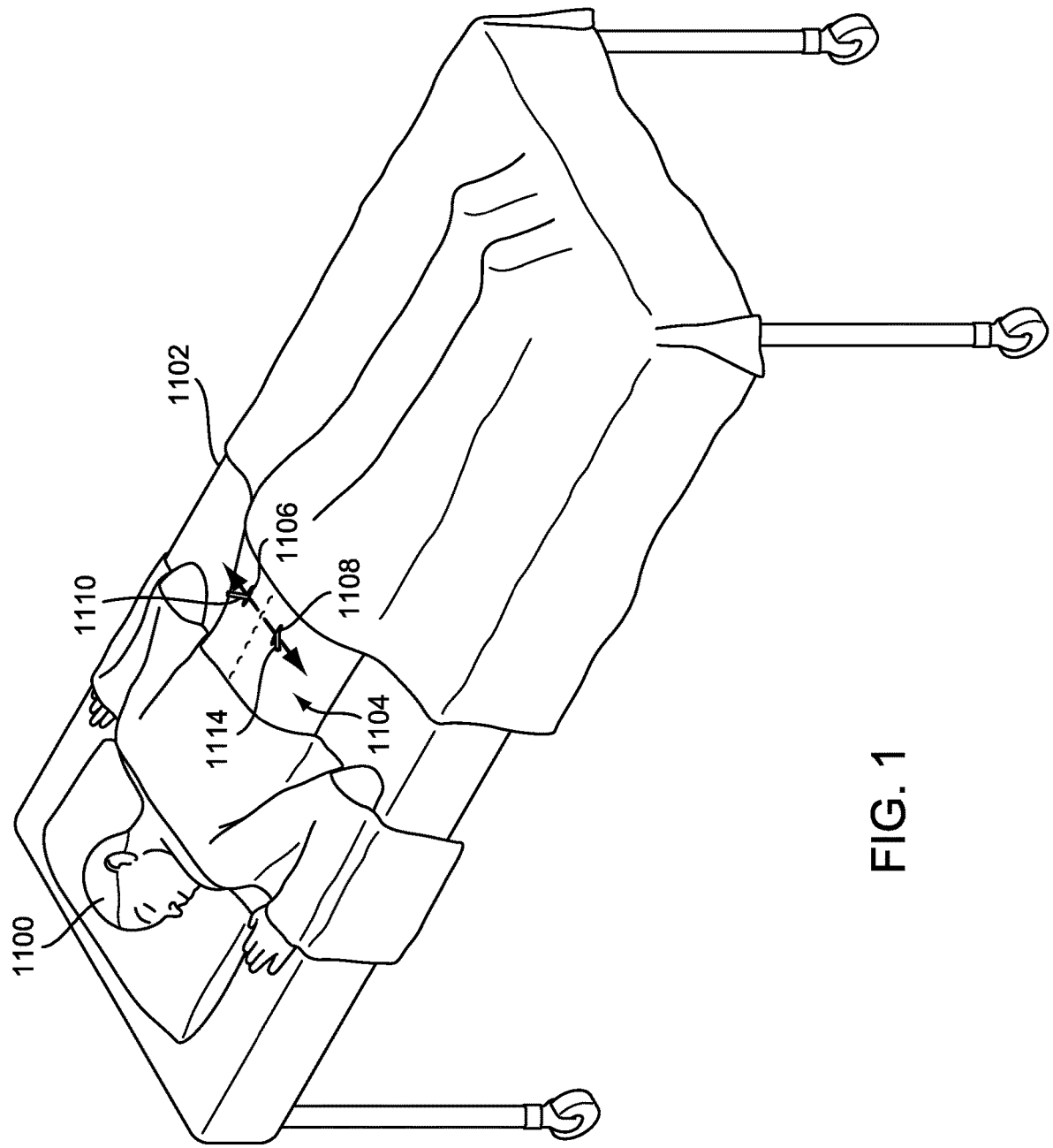
FIG. 1 is an isometric view of a preferred embodiment of a patient undergoing surgery.

FIG. 1 is an isometric view of a preferred embodiment of patient 1100 on operating table 1102. In this embodiment, patient 1100 is experiencing a surgical procedure to insert a spinal prosthesis. In particular, back 1104 of patient 1100 preferably includes first incision 1106 and second incision 1108. In a preferred embodiment, first incision 1106 includes first tube 1110 and second incision 1108 includes second tube 1114. Preferably, first incision 1106 and second incision 1108 are both less than one inch long. It should be understood that the placement of incisions 1106 and 1108 may be moved further together or closer apart and the location of incisions 1106 and 1108 in the current embodiment is only meant to be exemplary.

Figure 2:
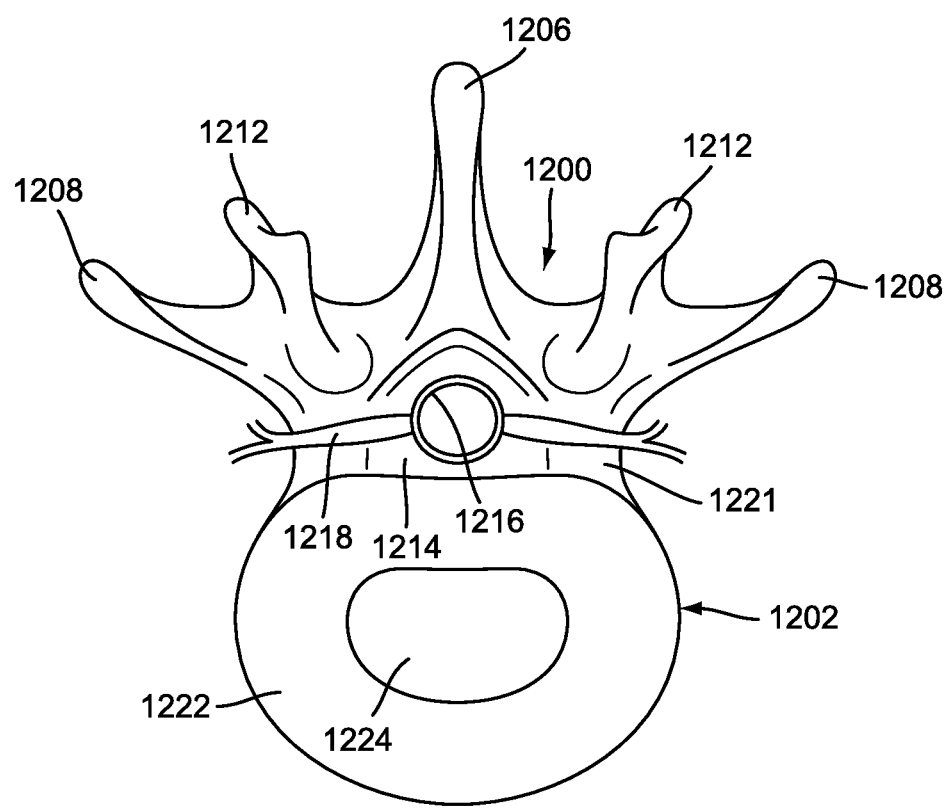
FIG. 2 is a plan view of a preferred embodiment of an intervertebral disc.

Preferably, first tube 1110 and second tube 1114 may be inserted into an intervertebral disc disposed between two adjacent vertebrae. For the purposes of this application, "disc" and "disk" have the same meaning and may be used interchangeably. FIG. 2 is a plan view of a single vertebra, shown generally at 1200, and an associated intervertebral disc 1202. (The anatomy shown in FIG. 2 is generally that of a lumbar vertebra, although the anatomy of thoracic, lumbar, and cervical vertebrae is similar; therefore, FIG. 2 can be considered to illustrate the basic principles of thoracic, lumbar, and cervical vertebral anatomy.) The spinous process 1206 of the vertebra 1200 extends dorsally and can typically be palpated and felt through the skin of the back. Also in the dorsally-extending portion of the vertebra 1200 are two transverse processes 1208 and two mammillary processes and facet joints 1212. A spinal canal 1214 (i.e., an opening) is provided in the vertebra 1200. The spinal cord and nerves 1216 extend through the spinal canal 1214 such that the spinal cord 1216 receives the full protection of the bony, dorsally-located spinous, transverse, and mammillary processes and facet joints 1206, 1208, 1212. The vertebral body also protects the spinal cord and nerves 1216 ventrally. Periodically, nerves 1218 branch out from the spinal cord 1216 to innervate various areas of the body. The forward or ventral edge of the vertebral foramen 1221 is defined by the vertebral body (not shown in FIG. 2), a bony, generally elliptical shelf in front of which the intervertebral disc 1202 rests. FIG. 2 also illustrates the basic structure of the intervertebral disc 1202, including the annulus fibrosis 1222 and the nucleus pulposus 1224.

Figure 3:
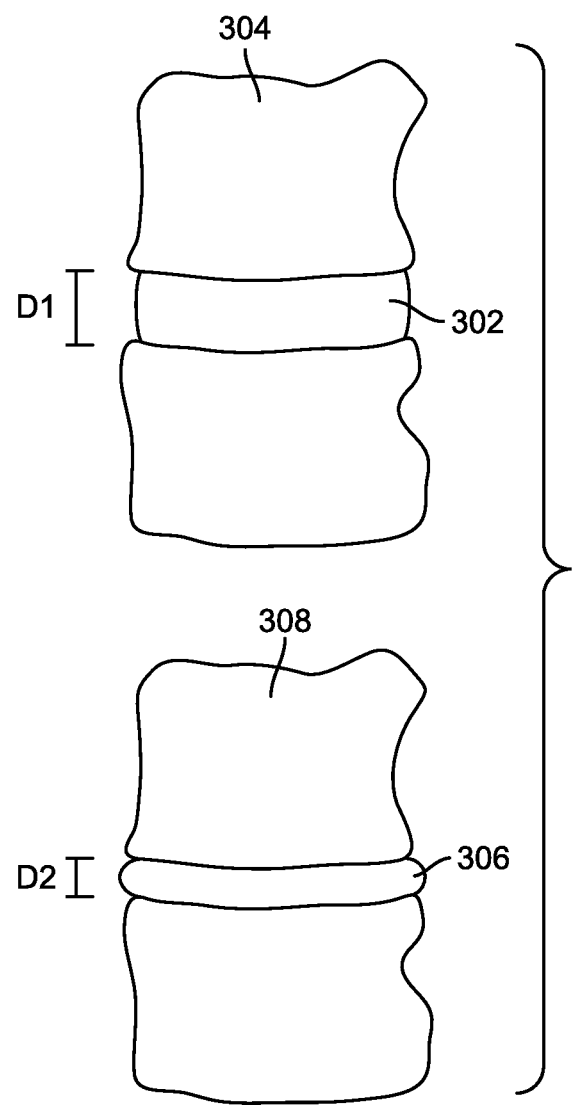
FIG. 3 is a schematic view of a preferred embodiment of a healthy intervertebral disc and an intervertebral disc that has degenerated.

In some cases, an intervertebral disc 1202 may degenerate over time, requiring the need for a spinal disc implant. FIG. 3 illustrates a preferred embodiment of degeneration. In this embodiment, healthy intervertebral disc 302 is disposed between vertebrae 304. In this case, vertebrae 304 are separated by a distance D1 because of support provided by disc 302. Also shown in FIG. 3 is unhealthy intervertebral disc 306, which is disposed between vertebrae 308. In this case, vertebrae 308 are separated by a distance D2 that is much smaller than distance D1 because of the degeneration of disc 306.

If an intervertebral disc has failed or degenerated, a typical correction is a surgical procedure to remove some or all of the intervertebral disc. Following this, a spinal prosthesis may be inserted in order to facilitate fusion of the vertebrae adjacent to the failed intervertebral disc. In a preferred embodiment, surgery may be performed in a manner that limits the size of the incisions needed to insert a prosthesis. Preferably, a spinal prosthesis includes provisions for easy insertion via a small incision in the back.

In some cases, a vertebral body could also be fully or partially replaced using a spinal prosthesis. The following detailed description refers to the replacement of an intervertebral disc, however in other embodiments these same principles could be applied to a spinal prosthesis configured to replace a vertebral body.

Figure 4:
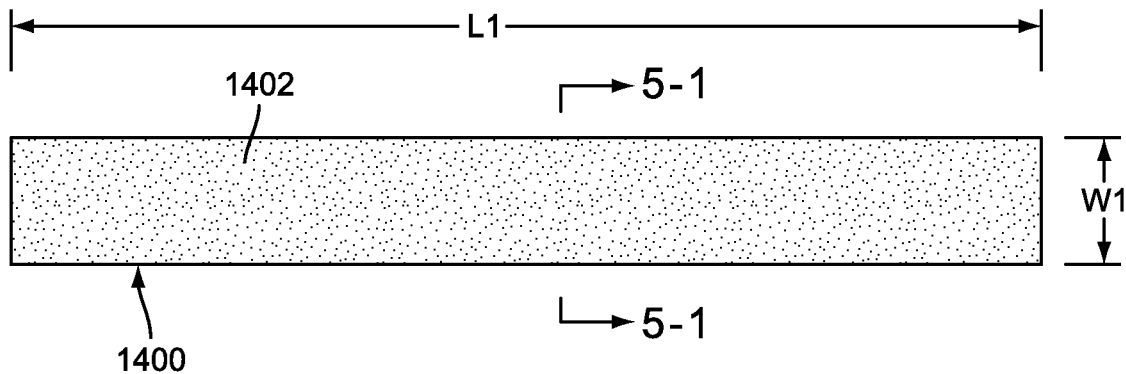
FIG. 4 is a plan view of a preferred embodiment of an implant strip.
Figures 1, 5:
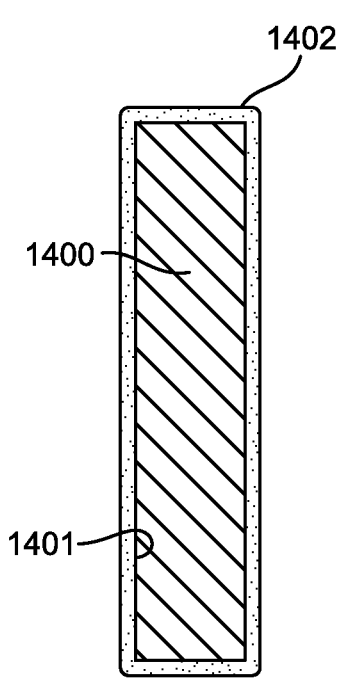
Figures 2, 5:
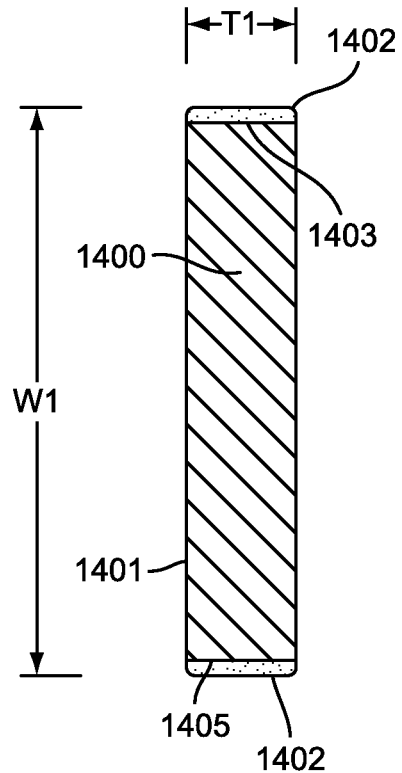

FIGS. 4 and 5 illustrate a preferred embodiment of implant strip 1400. Generally, implant strip 1400 may be a long thin strip. Preferably, implant strip 1400 has a length L1 much greater than a width W1. Additionally, the thickness T1 of implant strip 1400 is preferably small compared to both the length and the width of implant strip 1400. In some embodiments, length L1 may be between 1 cm and 100 m. In some embodiments, width W1 may be between 2 mm and 20 cm. In some embodiments, thickness T1 may be between 0.01 mm and 3 mm. It should be understood that if a vertebral body is being replaced, the thickness of implant strip 1400 could be much larger than the values discussed here.

As implant strip 1400 preferably has a relatively small profile, it may be inserted into smaller incisions, such as those shown in FIG. 1. However, to provide adequate support to the adjacent vertebrae, implant strip 1400 may preferably be packed tightly into intervertebral disc 1202. In some embodiments, the packing of implant strip 1400 may be tight or loose depending upon mechanical properties of implant strip 1400. For this reason, implant strip 1400 preferably includes provisions for conforming to a packed shape once it has been inserted into intervertebral disc 1202.

Generally, implant strip 1400 may be constructed of a material including metal. In some embodiments, implant strip 1400 may be a shape memory alloy. In some embodiments, implant strip 1400 may be made of a titanium alloy. In other embodiments, implant strip 1400 may comprise a combination of one or more materials including, but not limited to, cobalt chrome (CoCr), stainless steel, Nitinol, polymers, biological matrices, ceramics, or any biocompatible material. In a preferred embodiment, implant strip 1400 may be made of a material including titanium.

In some cases, a stainless steel alloy may be used as a coiling spring. This arrangement is useful because such alloys low fatigue and high fatigue resistance. Additionally, these alloys may have a high return force. Additionally, using a stainless steel alloy allows for increased corrosion resistance.

Preferably, implant strip 1400 may include provisions for changing shape. In some embodiments, implant strip 1400 may be manufactured at an elevated temperature with a first shape. Following this, implant strip 1400 may be cooled and formed into a second shape. Finally, as implant strip is placed in temperature ranges of 90-100 degrees Fahrenheit, it may revert back to the first shape. In a preferred embodiment, the first shape is a spiral coil and the second shape is a long rectangular strip.

In some embodiments, implant strip 1400 may include provisions for promoting bone growth, once it has been inserted into the intervertebral disc region. In some embodiments, implant strip 1400 may include a bone growth promoting agent. In a preferred embodiment, implant strip 1400 preferably includes bone growth promoting agent 1402 disposed along the entirety of its length. FIG. 5-1 is a cross sectional view of implant strip 1400 with bone growth promoting agent 1402 disposed along its entire outer surface 1401.

In some embodiments, bone growth promoting agent 1402 may be selectively applied to one or more portions of implant strip 1400 or may not be applied at all. Preferably, as shown in FIG. 5-2, bone growth promoting agent 1402 may be applied to top surface 1403 of outer surface 1401. Likewise, bone growth promoting agent 1402 may also be applied to bottom surface 1405 of outer surface 1401. Generally, any type of bone growth promoting agent may be applied and in any pattern. Methods for selectively applying bone growth promoting agents have been previously disclosed in U.S. Patent Publication Number US 2008/0269893 (U.S. patent application Ser. No. 11/740,181, filed on Apr. 25, 2007, entitled "Prosthesis with a Selectively Applied Bone Growth Promoting Agent"), the entirety of which is hereby incorporated by reference.

Figure 6:
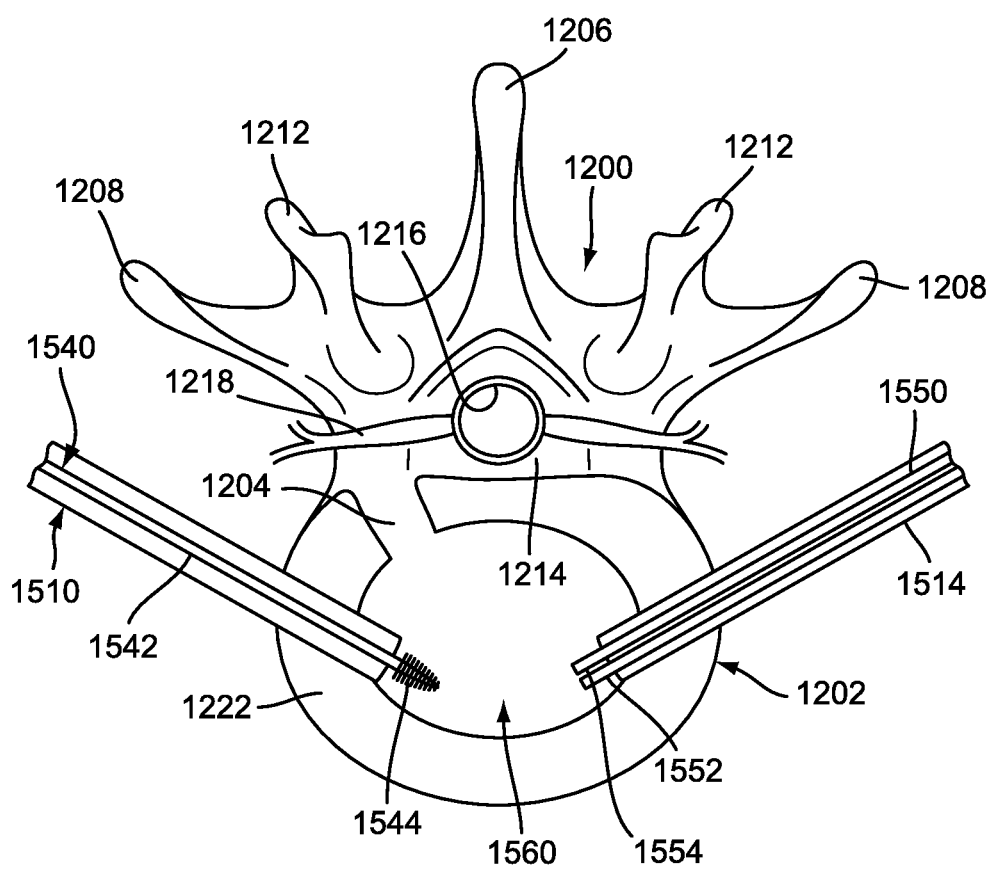
FIG. 6 is a plan view of a preferred embodiment of an intervertebral disc with a surgical tool and a dual catheter inserted.
Figure 7:
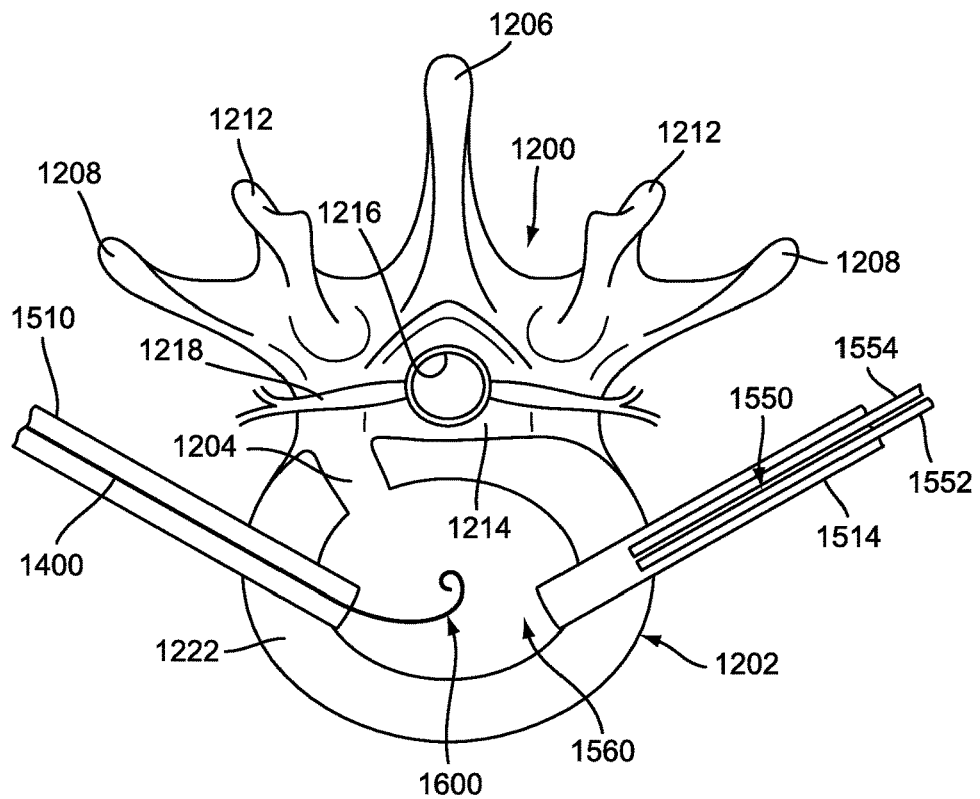
FIG. 7 is a plan view of a preferred embodiment of an intervertebral disc with an implant strip being inserted.
Figure 8:
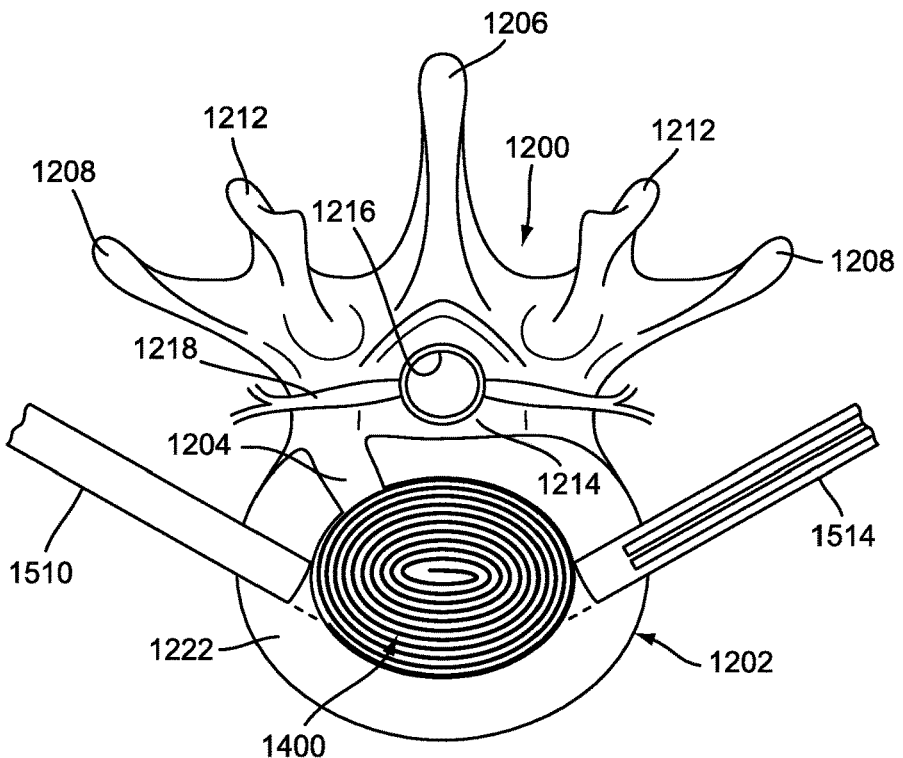
FIG. 8 is a plan view of a preferred embodiment of an implant strip fully inserted.

Details of a preferred embodiment of a surgical procedure used to insert a spinal prosthesis of some kind are best understood with respect to FIGS. 6-8. The following embodiment comprises steps for inserting a spinal prosthesis using two tubes, however it should be understood that in other embodiments, a single tube may be used for discectomy and/or implantation. In this case, any parallel steps involving the use of two tubes simultaneously could be performed sequentially with a single tube. In particular, steps using a camera and/or light inserted through one tube and a spinal tool through a second tube may be accomplished by using a single tube incorporating a light and/or camera at the periphery of the tube or just outside of the tube.

In a first step, first tube 1510 and second tube 1514 may be inserted into intervertebral disc 1202. Generally, one tube may be used for a surgical tool, while the second tube may be simultaneously used to insert a fiber optic camera into one of the incisions to give the surgeon a clear view of the intervertebral disc region. In some embodiments, first tube 1510 and second tube 1514 may be cannulae. The cross sectional shape of tubes 1510 and 1514 may be any shape, including oval-like, circular or otherwise round, as well as hexagonal or any polygonal shape.

Following the insertion of first tube 1510 and second tube 1514, a series of instruments may be used to remove portions of intervertebral disc 1202 and score the endplates. In some embodiments, first surgical device 1540 may be inserted into first tube 1510. First surgical device 1540 may be a brush, burr, rasp, or a shaver. In a preferred embodiment, first surgical device 1540 may include flexible shaft 1542 and wire brush tip 1544. Preferably, wire brush tip 1544 spins, removing portions of intervertebral disc 1202.

In some embodiments, dual catheter 1550 may be inserted into second tube 1514. Preferably, dual catheter 1550 may include first channel 1552 and second channel 1554. In some embodiments, first channel 1552 may include a fiber optic camera. With this configuration, the surgery may be visualized by the surgeon using the fiber optic camera. Additionally, second channel 1554 may be configured to inject water and/or provide a vacuum for removing debris. With this configuration, second channel 1554 may be used to clean out cavity 1560, which is created as a portion of intervertebral disc 1202 is removed. Once the necessary portions of intervertebral disc 1202 have been removed, first surgical device 1540 may be removed from first tube 1510.

Referring to FIGS. 7-8, implant strip 1400 may be inserted into cavity 1560 once a portion of intervertebral disc 1202 has been removed. As previously discussed, implant strip 1400 preferably has a material structure that allows it to change shape following insertion into cavity 1560. In a preferred embodiment, implant strip 1400 is configured to coil as it is exposed to temperatures between 90 and 100 degree Fahrenheit. In other embodiments, implant strip 1400 could coil due to non-temperature dependent memory, such as occurs with a measuring tape. This could be achieved using a titanium implant strip, for example.

In this embodiment, first portion 1600 of implant strip 1400 has started to coil as it is inserted into cavity 1560. Preferably, as implant strip 1400 is further inserted through first tube 1510, the portion disposed within cavity 1560 may deform and coil as well. In a preferred embodiment, implant strip 1400 may be inserted in a manner that allows implant strip 1400 to coil around itself completely, as seen in FIG. 8.

Generally, implant strip 1400 may be configured to fill cavity 1560 of intervertebral disc 1202 completely. For illustrative purposes, implant strip 1400 is shown here to be coiled with large gaps between adjacent portions. However, in some embodiments, implant strip 1400 may coil tightly so that no gaps are seen. In a preferred embodiment, implant strip 1400 may coil loosely to provide space or gaps between adjacent, radially spaced coils. This arrangement may help to facilitate bone growth to occur between the coils.

In an alternative embodiment, multiple implant strips may be used. Preferably, each implant strip may include a coiled shape, similar to the shape of the previous embodiment. In some embodiments, each of the implant strips may be disposed against one another. In some embodiments, each of the implant strips may be associated with different heights in order to create lordosis.

Figure 9:
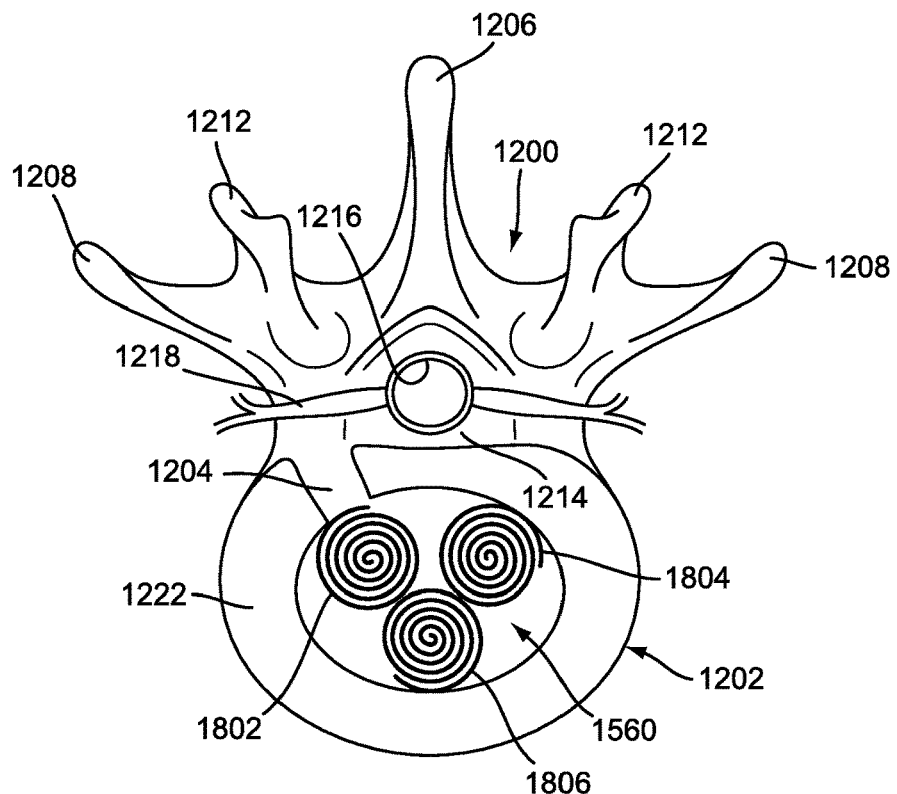
FIG. 9 is a plan view of a preferred embodiment of an intervertebral disc including three implant strips.

FIG. 9 is a preferred embodiment including multiple implant strips inserted within cavity 1560. In this embodiment, first implant strip 1802, second implant strip 1804, and third implant strip 1806 have been inserted into cavity 1560. Preferably, each of the implant strips 1802, 1804, and 1806 may be inserted in an identical manner to the method used to insert the implant strip of the previous embodiment. Generally, any number of implant strips may be inserted into cavity 1560.

Preferably, each of the implant strips 1802, 1804, and 1806 may be constructed of a shape memory alloy. In some embodiments, the shape memory alloy may be a nickel titanium alloy. In other embodiments, implant strips 1802, 1804, and 1806 may comprise a combination of one or more materials including, but not limited to, cobalt chrome (CoCr), stainless steel, Nitinol, polymers, biological matrices, ceramics, or any biocompatible material. In a preferred embodiment, implant strips 1802, 1804, and 1806 may be made of a material including titanium.

In other embodiments, the structure of an implant strip may be modified. In some embodiments, an implant strip may include a slightly different shape. In other embodiments, an additional material may be used in conjunction with the shape memory alloy of the previous embodiments.

Figure 10:
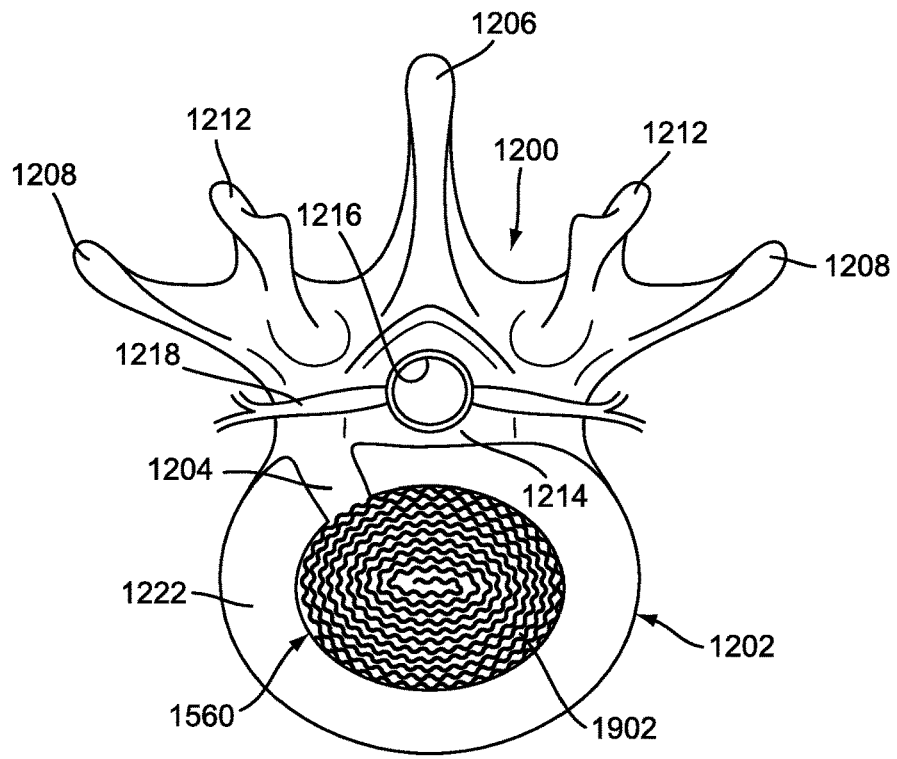
FIG. 10 is a plan view of a preferred embodiment of an intervertebral disc with a corrugated implant strip inserted.

FIG. 10 is a preferred embodiment of corrugated implant strip 1902, which has been inserted into cavity 1560. Preferably corrugated implant strip 1902 includes small bends along its length. Preferably, corrugated implant strip 1902 may be inserted into cavity 1560 in an identical manner to the method used to insert the previously discussed implant strips. As with the previous embodiments, it should be understood that a bone growth promoting agent may be applied to corrugated implant strip 1902. This arrangement allows for greater mechanical strength as well as for facilitating increased bone growth into implant strip 1902. By providing increased surface area, this arrangement may facilitate greater bone growth and more rapid bone healing.

Preferably, corrugated implant strip 1902 may be constructed of a shape memory material. In some embodiments, the shape memory alloy may be a nickel titanium alloy. In a preferred embodiment, corrugated implant strip 1902 may be made of a material including titanium. Generally, corrugated implant strip 1902 may be made of any of the materials discussed with respect to the previous embodiments of implant strips, including cobalt chrome (CoCr), stainless steel, Nitinol, polymers, biological matrices, ceramics or any biocompatible material.

Preferably, an implant device includes provisions for allowing for different kinds of motion that may occur in a spine.

In some embodiments, an implant device may include provisions to accommodate deflections in the axial direction. This may be a useful feature as axial forces may be applied to the implant strip by the adjacent vertebrae during normal activities such as walking, running, and bending of the spinal column. In other words, the implant strip may be configured to endure axial loads that are usually applied to spinal discs. Additionally, the implant device may be configured to accommodate bending, lateral (including shear forces), and twisting forces.

FIGS. 11-14 are intended to illustrate a generic embodiment of implant device 2200. Generally, implant device 2200 may be any kind of device configured for implantation into the human body. In some cases, implant device 2200 may be configured to be implanted between vertebrae, functioning as a full or partial disc replacement device. In a preferred embodiment, implant device 2200 may be an implant strip.

Figure 11:
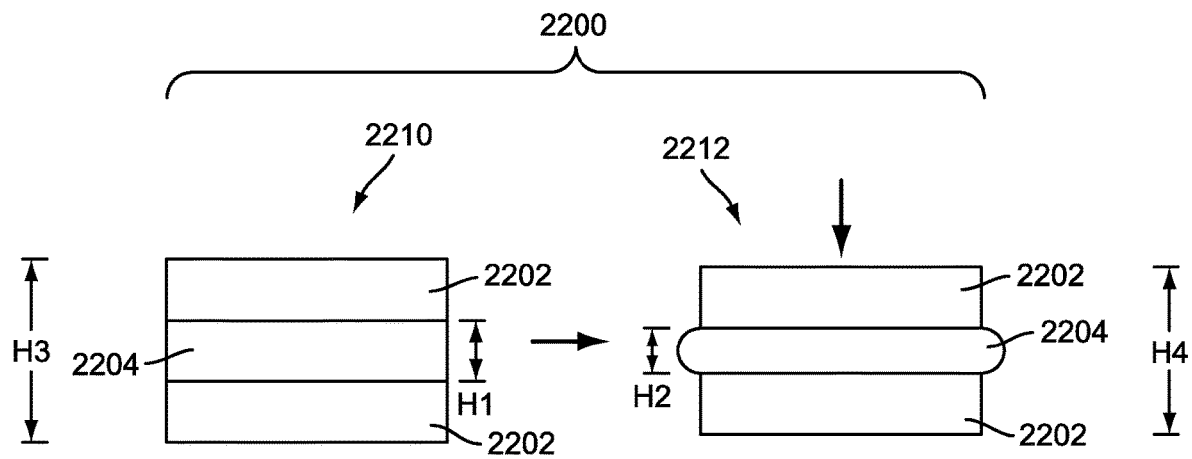
FIG. 11 is a schematic view of a preferred embodiment of an implant device in a pre-deflection state and a post-deflection state.

FIG. 11 is intended to illustrate a general embodiment of implant device 2200 in a pre-deflection state 2210 and a post-deflection state 2212. In this embodiment, implant device 2200 includes first portion 2202 and second portion 2204. Preferably, first portion 2202 is relatively rigid compared to second portion 2204. In other words, second portion 2204 is configured to deflect under axial forces before first portion 2202 would deflect. As shown in FIG. 11, second portion 2204 has a first height H1 in a pre-deflection state 2210 and a second height H2 in a post-deflection state 2212. First height H1 is preferably greater than second height H2. Additionally, first portion 2202 and second portion 2204 have a third combined height H3, in pre-deflection state 2210 and a fourth combined height H4 in post-deflection state 2212. Third combined height H3 is preferably greater that fourth combined height H4. This preferred arrangement allows for some deflection of implant device 2200 without causing fatigue or failure.

Figure 12:
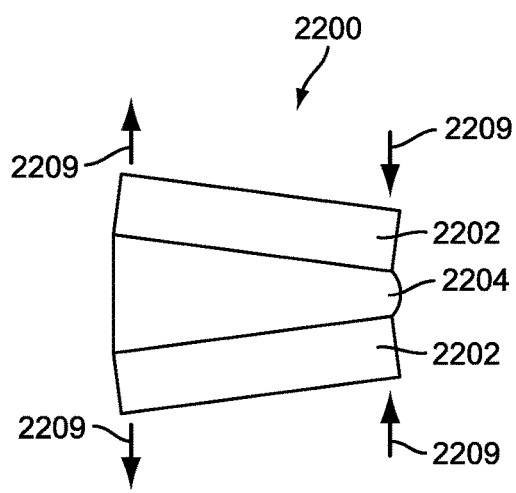
FIG. 12 is a schematic view of a preferred embodiment of an implant device undergoing bending.

In addition to deflection in the axial direction, a spinal implant device may also be configured to undergo bending, lateral and twisting motions. Implant device 2200 is seen in FIG. 12 to undergo a bending motion due to bending forces 2209. As bending forces 2209 are applied to first portion 2202, second portion 2204 may bend. This preferred arrangement allows for some bending of implant device 2200 without causing fatigue or failure.

Figure 13:
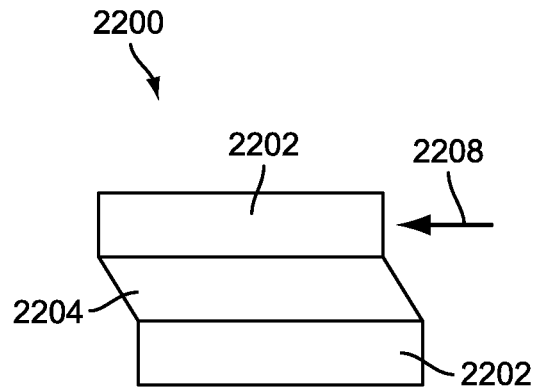
FIG. 13 is a schematic view of a preferred embodiment of an implant device undergoing translation.

Implant device 2200 is seen in FIG. 13 undergoing a lateral motion due to a lateral force 2208. As lateral force 2208 is applied to first portion 2202, second portion 2204 may be deflected laterally. This preferred arrangement allows for some lateral deflection of implant device 2200 without causing fatigue or failure.

Figure 14:
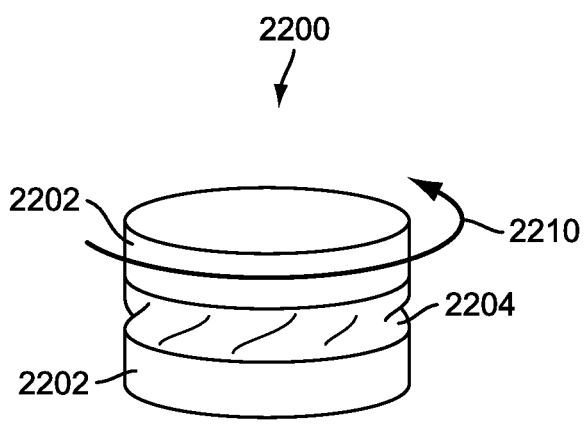
FIG. 14 is a schematic view of a preferred embodiment of an implant device undergoing twisting.

Referring to FIG. 14, implant device 2200 is seen in undergoing a twisting motion due to a rotational force 2210. As rotational force 2210 is applied to first portion 2202, second portion 2204 may be twisted. This preferred arrangement allows for some twisting of implant device 2200 without causing fatigue or failure.

In each of these cases, first implant devices 2200 is provided with restoring forces via second portion 2204. Additionally, although these different types of deflections (due to compressive, bending, twisting and lateral forces) have been shown separately, it should be understood that implant device 2200 may be configured to undergo any combination of or all of these various types of deformations simultaneously.

First portion 2202 may be made of any material, including both shape memory alloys and spring steel, as well as other types of materials, including previously discussed materials for implant strip 1400. Second portion 2204 may be made of any material that may be less rigid than first portion 2202. In addition, second portion 2204 may be designed to deflect and/or deform under various forces. Examples of such materials include, but are not limited to, elastomers, soft metals, plastics, polymers, wire meshes (made from materials such as Dacron or ceramics), as well as other types of materials.

Additionally, in some embodiments, first portion 2202 and second portion 2204 could be made of the same material. However, the rigidity of second portion 2204 could be modified by changing the structural properties of second portion 2204. This configuration may be achieved by inserting holes or slots or modifying the structure of second portion 2204 in other ways. With these types of modifications, first portion 2202 may be more rigid than second portion 2204 even though they are made of the same material.

Preferably, the degree of deflection of implant device 2200 may vary. During the initial implantation, implant device 2200 may deflect or compress until the height of the implant device is about eighty percent of the initial height of the implant strip prior to implantation. This initial deflection is primarily due to normal stresses applied by the adjacent vertebrae when the spinal column is at rest. During motion, however, implant device 2200 may continue to deflect due to increased axial loads from the adjacent vertebrae. The degree of deflection may be between 15 and 25 percent of the initial height of implant device 2200. It should be understood, however, that the degree of deflection is not limited and may vary according to properties of the various materials that are used. In some cases, the degree of deflection could be much larger than 25 percent or much less that 15 percent. By carefully selecting the material, size, design as well as other structural features of second portion 2204, the deflection of implant device 2200 can be better controlled. The following embodiments illustrate ways in which the deflection of implant device 2200 can be achieved using different materials and structural features for second portion 2204.

Figure 15:
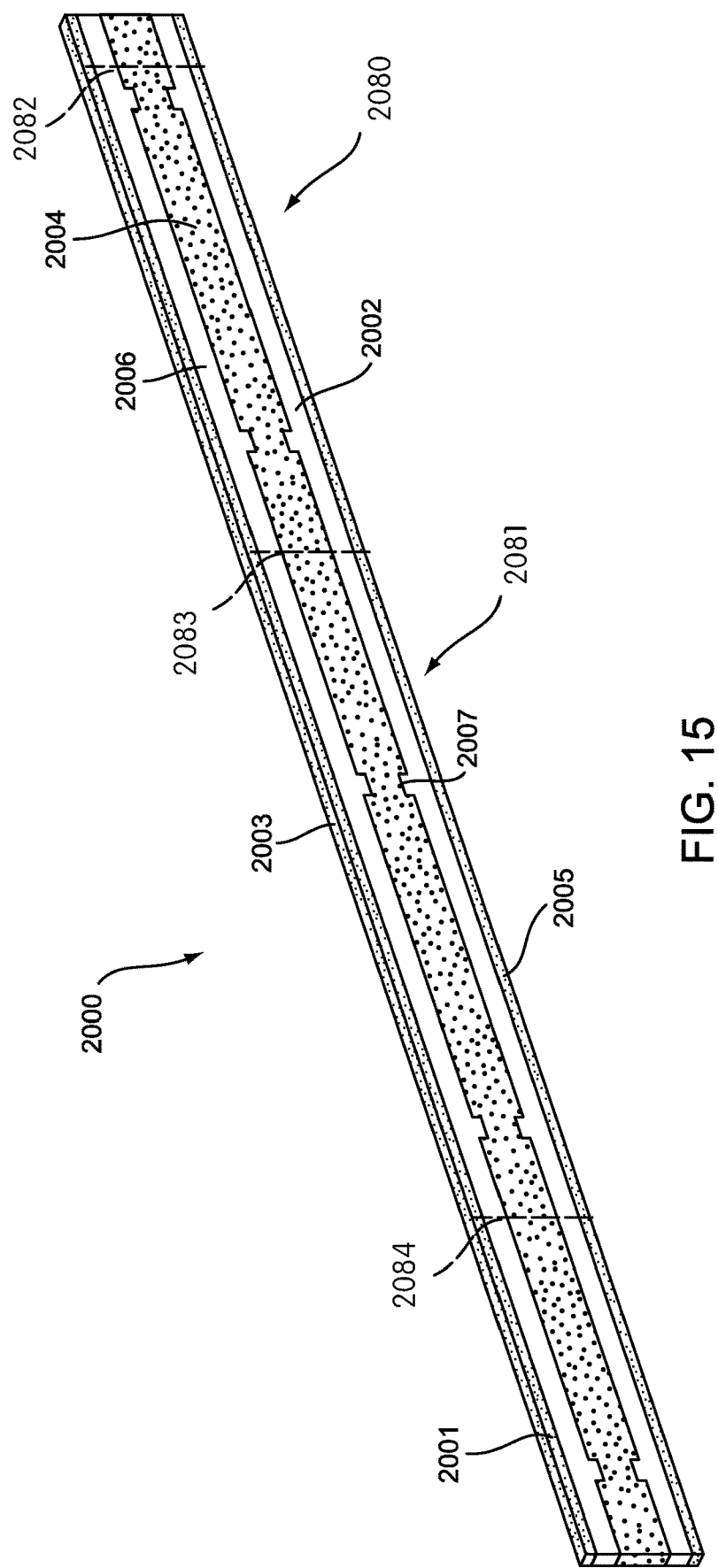
FIG. 15 is an isometric view of a preferred embodiment of an implant strip.

FIG. 15 is an isometric view of a preferred embodiment of implant strip 2000. In some embodiments, implant strip 2000 may extend in a lateral direction from a first lateral side portion 2002 to a second lateral side portion 2006. Preferably, first lateral side portion 2002 and second lateral side portion 2006 may be constructed of a similar material to the implant strips of the previous embodiments. In particular, side portions 2002 and 2006 may be made of a substantially rigid material that does not deflect much under axial loads.

In some embodiments, elastomer strip 2004 may be disposed between first lateral side portion 2002 and second lateral side portion 2006. Elastomer strip 2004 is preferably made of a flexible material. In some embodiments, elastomer strip 2004 may be joined to first lateral side portion 2002 and second lateral side portion 2006. In some embodiments, elastomer strip 2004 may encase perforated edges, teeth or roughed edges of first lateral side portion 2002 and second lateral side portion 2006 in order to ensure a positive mechanical connection. In this preferred embodiment, first lateral side portion 2002 and second lateral side portion 2206 may be associated with teeth 2007. Using this configuration, teeth 2007 provide a point of attachment for elastomer strip 2004 to first lateral side portion 2002 and second lateral side portion 2006. In other embodiments, other provisions may be used to fixedly attach elastomer strip 2004 to first lateral side portion 2002 and second lateral side portion 2006.

In some embodiments, implant strip 2000 may include a bone growth promoting agent. In this embodiment, top portion 2003 and bottom portion 2005 are preferably coated with a bone growth promoting agent 2001. Generally, any type of bone growth promoting agent may be used. Additionally, any type of pattern for a bone growth promoting agent may be used. Various bone growth promoting agents and patterns have been previously referenced. Using this configuration, implant strip 2000 may be configured to stimulate increased bone growth at adjacent vertebrae where implant strip 2000 is implanted. In some embodiments, such a configuration may be used in a manner similar to a spinal cage, which provides a means of fusing two vertebral bodies together.

Figure 16:
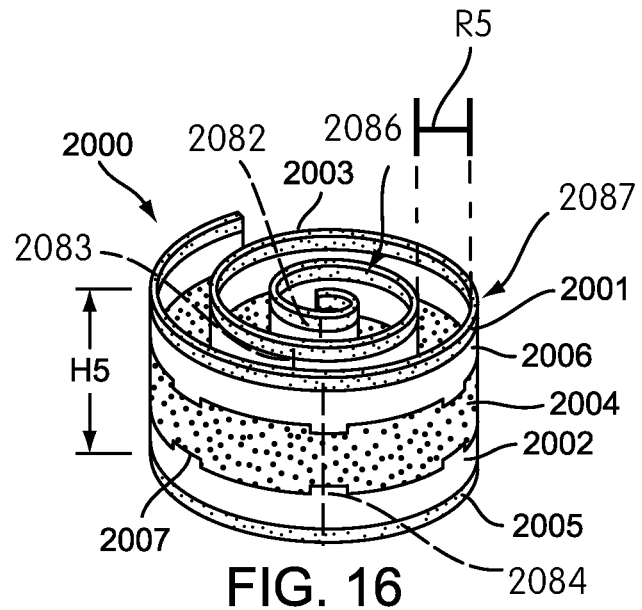
FIG. 16 is an isometric view of a preferred embodiment of an implant strip that has coiled.
Figure 17:
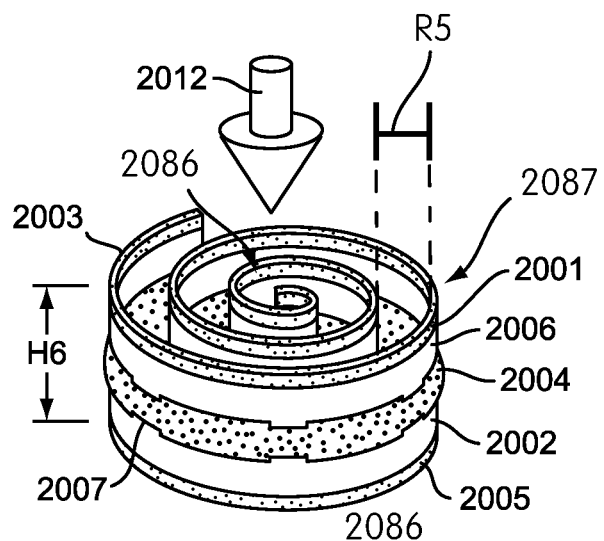
FIG. 17 is an isometric view of a preferred embodiment of a coiled implant strip under axial force.

FIGS. 16 and 17 are a preferred embodiment of implant strip 2000 after it has been coiled. Initially, implant strip 2000 has an axial height H5. As axial force 2012 is applied to flexible implant strip 2000, elastomer strip 2004 may deflect in the axial direction, allowing first lateral side portion 2002 and a second lateral side portion 2006 to squeeze together. In this embodiment, flexible implant strip 2000 has a height H6 that is less than height H5 following axial deflection. Generally, elastomer strip 2004 has deformed and may slightly bulge outwards. This preferred arrangement allows implant strip 2000 to deflect under axial forces applied by adjacent vertebrae following implantation, which provides a similar function to a spinal disc. Also, using this configuration flexible implant strip 2000 may be configured as a flexible spiral coil that may not escape containment. Preferably, using this arrangement, the adjacent vertebrae may engage lateral side portions 2002 and 2006 of implant strip 2000 to lock it into place.

Referring to FIGS. 15-17, implant strip 2000 preferably is configured to be coiled in a manner that prevents contact between adjacent coils. In this embodiment, implant strip 2000 may include first longitudinal portion 2080 and second longitudinal portion 2081 extending in a longitudinal direction down the length of implant strip 2000, as seen in FIG. 15. First longitudinal portion 2080 extends from first boundary 2082 to second boundary 2083. Second longitudinal portion 2081 extends from second boundary 2083 to third boundary 2084. Generally, the lengths of each longitudinal portion 2080 and 2081 are approximately equal to one 360 degree turn of a coil when implant strip 2000 is in a coiled state. In this embodiment, longitudinal portions 2080 and 2081 are adjacent to one another, however in other embodiments longitudinal portions 2080 and 2081 may not be adjacent to one another.

Preferably, first longitudinal portion 2080 is configured to form a first inner coil 2086, as seen in FIGS. 15-17, as implant strip 2000 forms a coiled shape. Likewise, second longitudinal portion 2081 is configured to form a second outer coil 2087. In a preferred embodiment, second outer coil 2087 is spaced radially outward from first inner coil 2086. In some embodiments, first inner coil 2086 and second outer coil 2087 are spaced apart by a radial distance R5 when first lateral side portion 2002 and second lateral side portion 2006 are not in motion (see FIG. 16). Generally, distance R5 may have any value and may vary from one embodiment to another. Using this preferred arrangement, first inner coil 2086 and second outer coil 2087 are spaced to prevent contact with one another. Preferably, first inner coil 2086 and second outer coil 2087 are also spaced apart when first lateral side portion 2002 and second lateral side portion 2006 are in motion, such as when implant strip 2000 is in a compressed or axially deflected state (see FIG. 17). This arrangement helps to reduce or substantially eliminate particulate debris that may result from the rubbing of various portions together over the lifetime of implant strip 1400.

Preferably, provisions for preventing contact between portions of an implant strip may be provided in other embodiments as well. The principles discussed here may be generally applied to any type of implant strip including a first longitudinal portion and a second longitudinal portion. In some embodiments, these implant strips may or may not include deforming portions.

In other embodiments, an implant strip may include different provisions for allowing deflection of the implant strip in the axial direction. In some embodiments, an implant strip may include perforated portions with large gaps or holes that reduce rigidity and thereby allow for some deflection of the implant strip. It should be understood that throughout these embodiments, illustrated in FIGS. 18-34, the various implant strips include portions of differing rigidity. Furthermore, in each of these embodiments, the portions of differing rigidity are joined together.

FIGS. 18-25 are preferred embodiments of sections of spinal implant strips that are configured for various types of deflection, including axial deflection. The spinal implant strips are also capable of accommodating other types of deflection, including bending, twisting, and lateral shear. Throughout these embodiments, it should be understood that the implant strips may be made of any material configured to coil or deflect in the circumferential direction. In some embodiments, these sections of implant strips may be made of a single material or comprise a combination of one or more materials including, but not limited to, cobalt chrome (CoCr), stainless steel, Nitinol, polymers, biological matrices, ceramics or any biocompatible material. In a preferred embodiment, these sections of implant strips may be made of a material including titanium.

Figure 18:
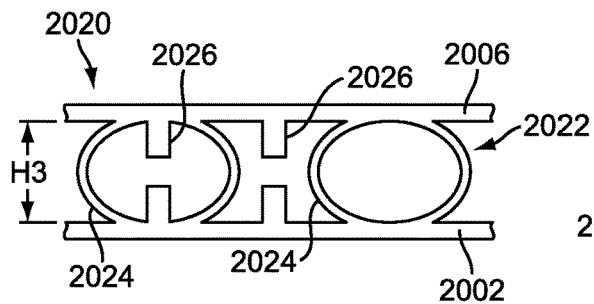
FIG. 18 is a plan view of a preferred embodiment of a section of an implant strip configured for axial deflection.

FIG. 18 is a preferred embodiment of a portion of first implant strip 2020 prior to deflection. First implant strip 2020 preferably includes lower edge 2002 and upper edge 2006. Lower edge 2002 and upper edge 2006 are preferably thin strips that form an outer periphery for first implant strip 2020.

Additionally, first implant strip 2020 may include first deflecting portions 2024 that are disposed between lower edge 2002 and upper edge 2006. Preferably, lower edge 2002 and upper edge 2006 are joined to first deflecting portions 2024. For purposes of clarity, only a section of first implant strip 2020 is shown here, however it should be understood that first deflecting portions 2024 are preferably disposed along the entire length of first implant strip 2020. Generally, the spacing and number of first deflecting portions 2024 may be varied in order to change the deflection properties of first implant strip 2020.

In this embodiment, first deflecting portions 2024 may be elliptically shaped prior to deflection. In other embodiments, the shape of first deflecting portions 2024 may vary. Examples of other shapes that may be used include, but are not limited to, circles, diamonds, as well as any polygonal shape. Additionally, in other embodiments, the thickness associated with first deflecting portions 2024 could be changed. By varying these properties of first deflecting portions 2024, the deflection properties of first implant strip 2020 may be modified.

In some embodiments, first implant strip 2020 may also include motion limiting features that prevent excessive deflection in the axial direction. In this embodiment, first implant strip 2020 may include motion limiting tabs 2026. Preferably, motion limiting tabs 2026 may be disposed between edges 2002 and 2006. Furthermore, motion limiting tabs 2026 may be disposed within deflecting portions 2024 and/or adjacent to deflecting portions 2024.

Preferably, deflecting portions 2024 and motion limiting tabs 2026 may be formed by cutting or removing portions of first implant strip 2020, which creates gaps within interior space 2022. This cutting may be done using techniques known in the art, such as stamping, punching, laser fusion and/or water drilling, or any combination of techniques. In other embodiments, first implant strip 2020, including deflecting portions 2024 and tabs 2026 may be formed using a die of some kind. These techniques are preferably used to create smooth edges in order to prevent burrs. Using this configuration, scar tissue due to burrs may be substantially reduced following implantation of first implant strip 2020. In other embodiments, however, techniques used that leave burrs intact may be used so that the remaining burrs may facilitate in-growth of bone.

Figure 19:
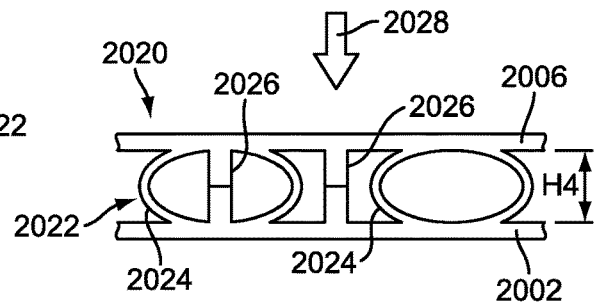
FIG. 19 is a plan view of a preferred embodiment of a section of an implant strip under axial load.
Figure 20:
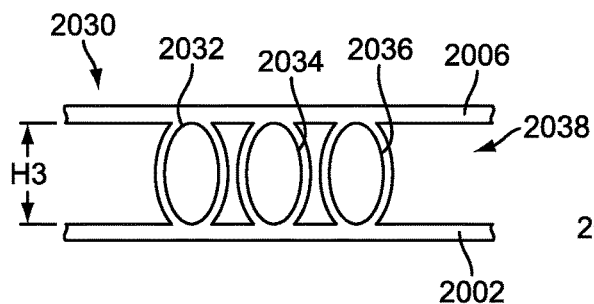
FIG. 20 is a plan view of a preferred embodiment of a section of an implant strip configured for axial deflection.
Figure 21:
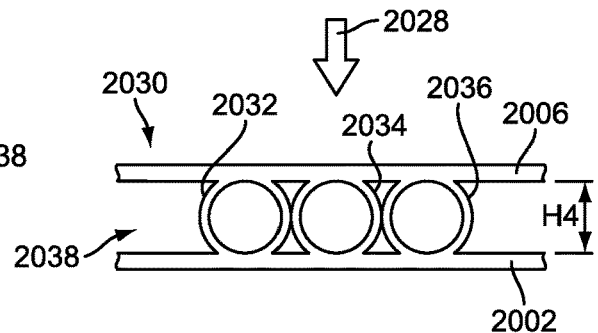
FIG. 21 is a plan view of a preferred embodiment of a section of an implant strip under axial load.

Following the insertion of first implant strip 2020 between two adjacent vertebrae, an axial force may be experienced as the vertebrae are compressed during motion of the spinal column. Referring to FIG. 19, first deflecting portions 2024 may be compressed under axial force 2028. As first deflecting portions 2024 compress, lower edge 2002 and upper edge 2006 move closer together. As previously discussed, excessive axial deflection may be prevented using motion limiting tabs 2026. Preferably, tabs 2026 are substantially rigid and therefore will not deflect or deform under axial force 2028. Therefore, as tabs 2026 make contact, the compression of first deflecting portions 2024 may cease. In this embodiment, the height of implant strip 2020 has been modified from an original height H3 to a modified height H4 that is less than H3. Once axial force 2028 has been removed or reduced, implant strip 2020 may expand in the axial direction as deflecting portions 2024 uncompress. Using tabs 2026 helps to prevent fatigue failure of deflecting portions 2024 by limiting the range of motion.

Referring to FIGS. 20-25, an implant strip may include different types of deflecting portions. Additionally, an implant strip may or may not include motion limiting tabs. In a second embodiment, seen in FIGS. 20-21, second implant strip 2030 includes first deflecting ellipse 2032, second deflecting ellipse 2034 and third deflecting ellipse 2036 disposed between edges 2002 and 2006 and within interior space 2038. Preferably, ellipses 2032, 2034, and 2036 are joined to edges 2002 and 2006. As axial force 2028 is applied, deflecting ellipses 2032, 2034 and 2036 are compressed until they obtain a substantially circular shape. At this point, ellipses 2032, 2034, and 2036 are disposed against one another, which may prevent any further deflection or deformation in the axial direction.

Figure 22:
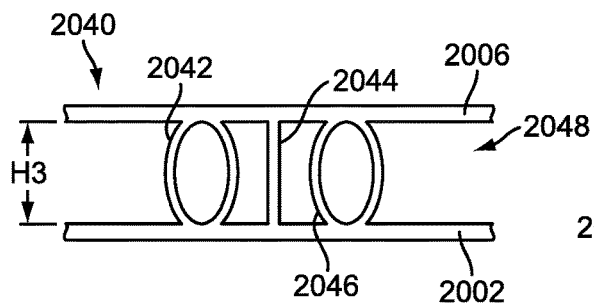
FIG. 22 is a plan view of a preferred embodiment of a section of an implant strip configured for axial deflection.
Figure 23:
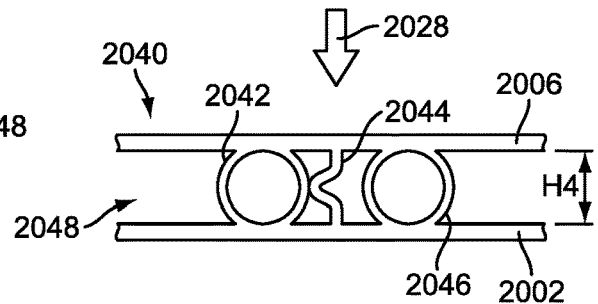
FIG. 23 is a plan view of a preferred embodiment of a section of an implant strip under axial load.

In a third embodiment, shown in FIGS. 22-23, third implant strip 2040 includes fourth deflecting ellipse 2042 and fifth deflecting ellipse 2046 disposed between edges 2002 and 2006 and within interior space 2048. Preferably, ellipses 2042 and 2046 are joined to edges 2002 and 2006. In addition, third implant strip 2040 preferably includes cross bar 2044 that is disposed between fourth deflecting ellipse 2042 and fifth deflecting ellipse 2046. Cross bar 2044 preferably connects to both lower edge 2002 and upper edge 2006. In a preferred embodiment, deflecting ellipses 2042 and 2046 as well as cross bar 2044 may all deflect under axial force 2028. In particular, cross bar 2044 may experience column deflection. Preferably, cross bar 2044 only partially deflects, which limits the axial motion of lower edge 2002 and upper edge 2006.

Figure 24:
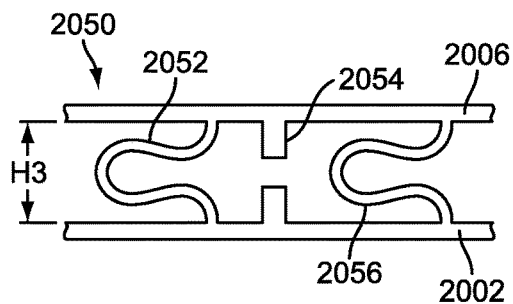
FIG. 24 is a plan view of a preferred embodiment of a section of an implant strip configured for axial deflection.
Figure 25:
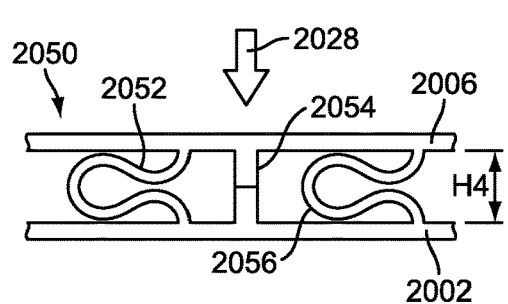
FIG. 25 is a plan view of a preferred embodiment of a section of an implant strip under axial load.

In a fourth embodiment, seen in FIGS. 24-25, fourth implant strip 2050 includes first curved portion 2052 and second curved portion 2056. Preferably, curved portions 2052 and 2056 are joined to edges 2002 and 2006. Fourth implant strip 2050 also preferably includes motion limiting tabs 2054. As axial force 2028 is applied to fourth implant strip 2050, curved portions 2052 and 2056 may deflect in the axial direction. Preferably, as tabs 2054 make contact, the deflection of lower edge 2002 towards upper edge 2006 may cease. Additionally, curved portions 2052 and 2056 may contact edges 2002 and 2006, preventing further deflection.

FIGS. 26-28 illustrate another preferred embodiment of implant strip 2300 that is configured for axial deflection. Implant strip 2300 includes upper side 2304 and lower side 2306 that extend vertically. Protruding portion 2303 preferably extends outwards from, and is preferably joined with, upper side 2304 and lower side 2306. In particular, protruding portion 2303 includes first sloped portion 2310 and second sloped portion 2312 as well as flat portion 2308. Using this preferred arrangement, implant strip 2300 may be configured for slight deflections in the axial direction, as some slight compression of implant strip 2300 may occur at protruding portion 2303. In particular, as axial loads are applied to implant strip 2300, the angle of first sloped portion 2310 and second sloped portion 2312 with respect to upper side 2304 and lower side 2306 may vary.

FIG. 28 illustrates an alternative embodiment of a cross sectional view of protruding portion 2303. In the embodiment shown in FIG. 27, first sloped portion 2310 and second sloped portion 2312 are straight portions. Alternatively, protruding portion 2303 could include first curved portion 2320 and second curved portion 2322. Using an alternative shape for protruding portion 2303 allows for changes in the deflecting properties of implant strip 2300. In other embodiments, the shape of protruding portion 2303 could be further modified to change the deflecting properties of implant strip 2300.

Implant strip 2300 also preferably includes slots 2302. In this embodiment, slots 2302 extend from upper side 2304 to lower side 2306 of implant strip 2300. Slots 2302 preferably extend through protruding portion 2303. The addition of slots 2302 to implant strip 2300 generally decreases the rigidity of protruding portion 2303. Using this configuration, slots 2302 may provide increased deflection of protruding portion 2303.

Figure 29:
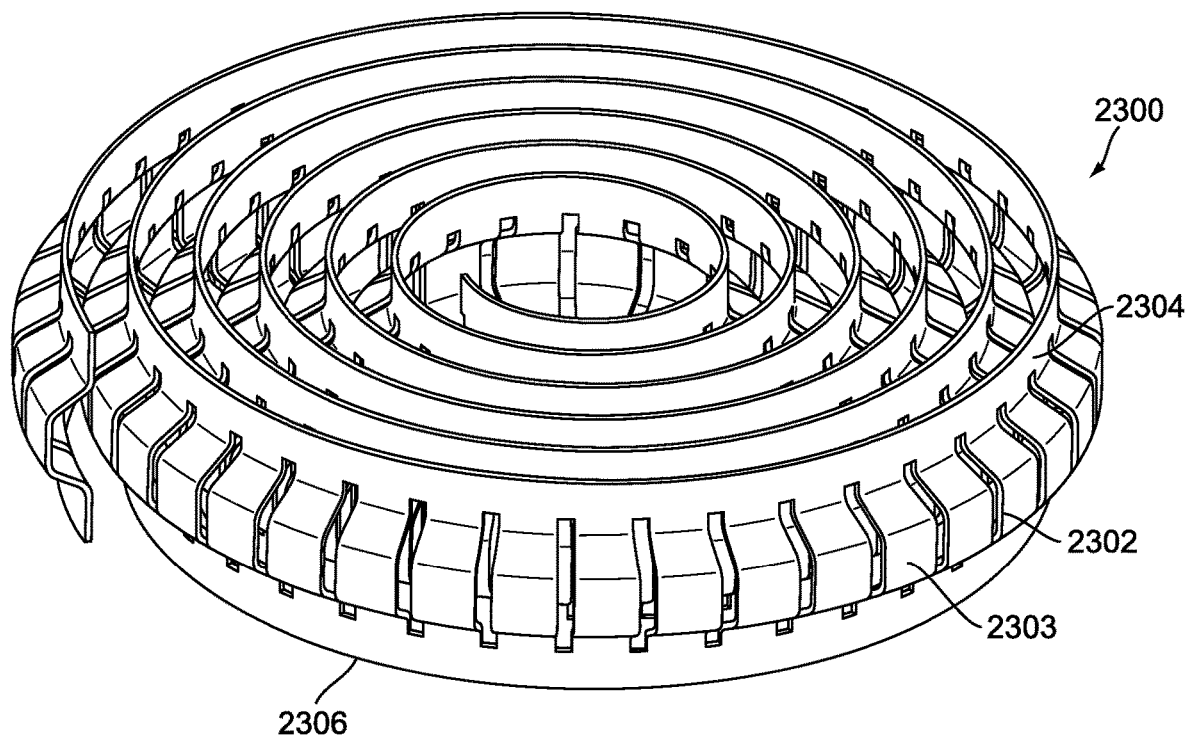
FIG. 29 is an isometric view of a preferred embodiment of a coiled implant strip with slots.
Figure 30:
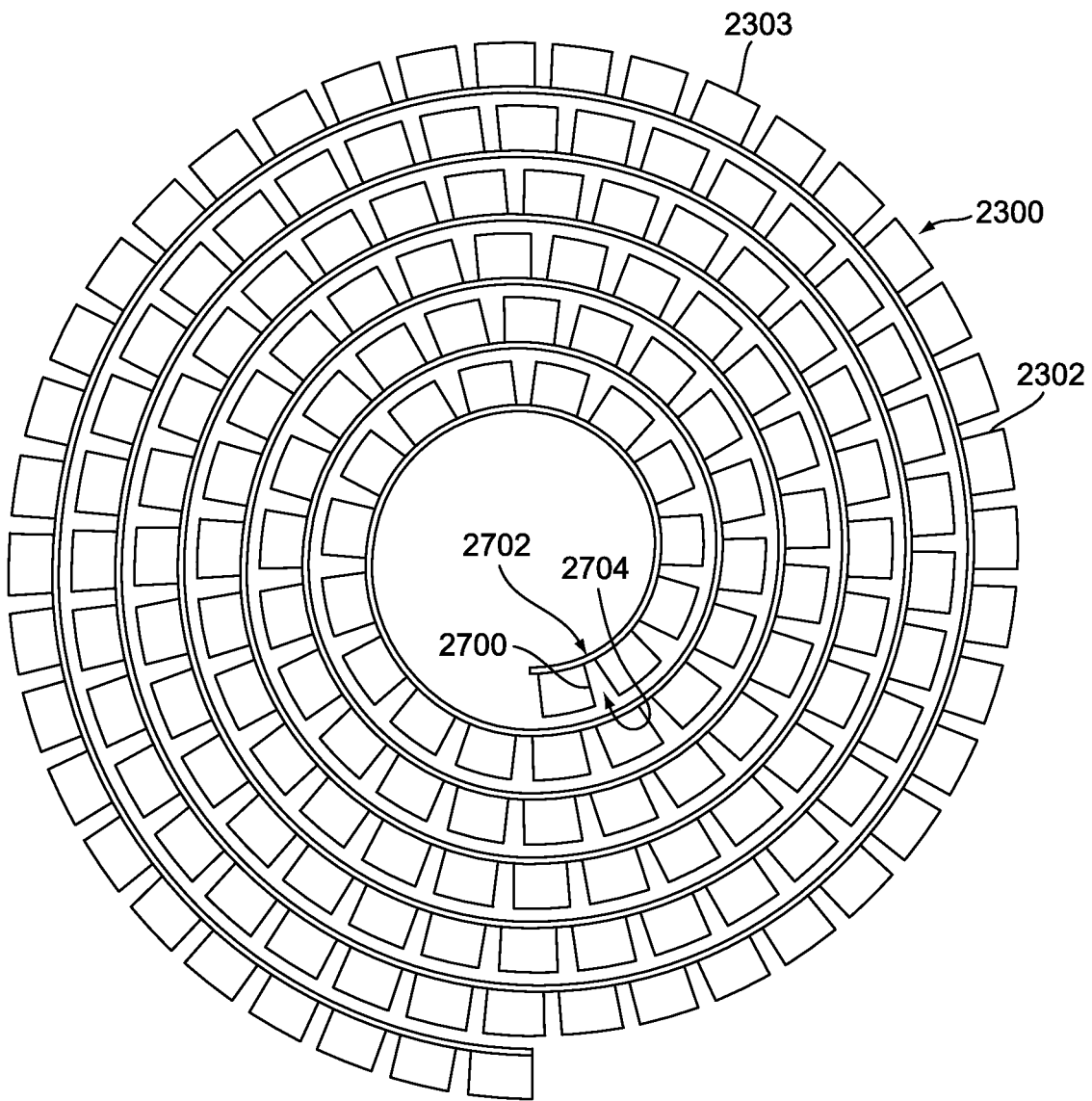
FIG. 30 is a top view of a preferred embodiment of a coiled implant strip with slots.

FIGS. 29 and 30 are a preferred embodiment of implant strip 2300 following implantation. As implant strip 2300 is coiled, implant strip 2300 is configured to deflect in the circumferential direction. In a preferred embodiment, the deflection primarily occurs at slots 2302. FIG. 30 illustrates the widening of slots 2302 during coiling. For example, first slot 2700 of implant strip 2300 is wider at first end 2704 than second end 2702.

Figure 31:
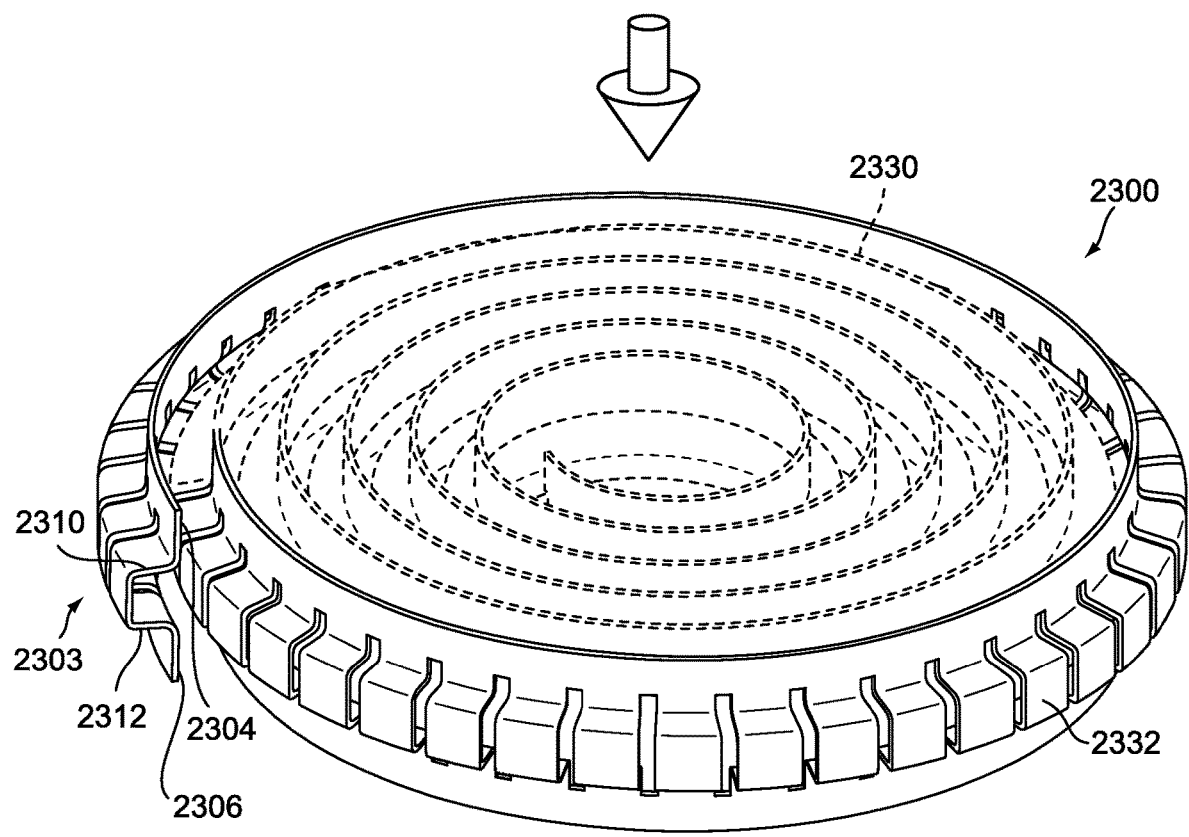
FIG. 31 is an isometric view of a preferred embodiment of an implant strip undergoing axial deflection.

FIG. 31 is a preferred embodiment of outer ring 2332 of implant strip 2300 undergoing axial deflection. For purposes of clarity, inner rings 2330 of implant strip 2300 are shown in phantom. As an axial force is applied, protruding portion 2303 deflects. In particular, the angle between upper side 2304 and first sloped portion 2310 and the angle between lower side 2306 and second sloped portion 2312 may change as upper side 2304 and lower side 2306 are squeezed together.

In some embodiments, the number, shape, and size of slots associated with an implant strip may vary. By changing the number, shape, orientation, and/or size of slots of an implant strip, the axial loading characteristics of the implant strip may be controlled. Increasing the number of slots may increase the degree of axial deflection, as the rigidity of protruding portion 2303 is reduced with an increasing number of slots. Likewise, decreasing the number of slots may decrease the degree of axial deflection, as the rigidity of protruding portion 2303 is increased with a decreased number of slots.

Additionally, changing the number of slots may also increase the flexibility of the implant strip in the circumferential direction. Increasing the number of slots may generally increase the amount of deflection in the circumferential direction. Likewise, decreasing the number of slots may generally decrease the amount of deflection in the circumferential direction.

Figure 32:
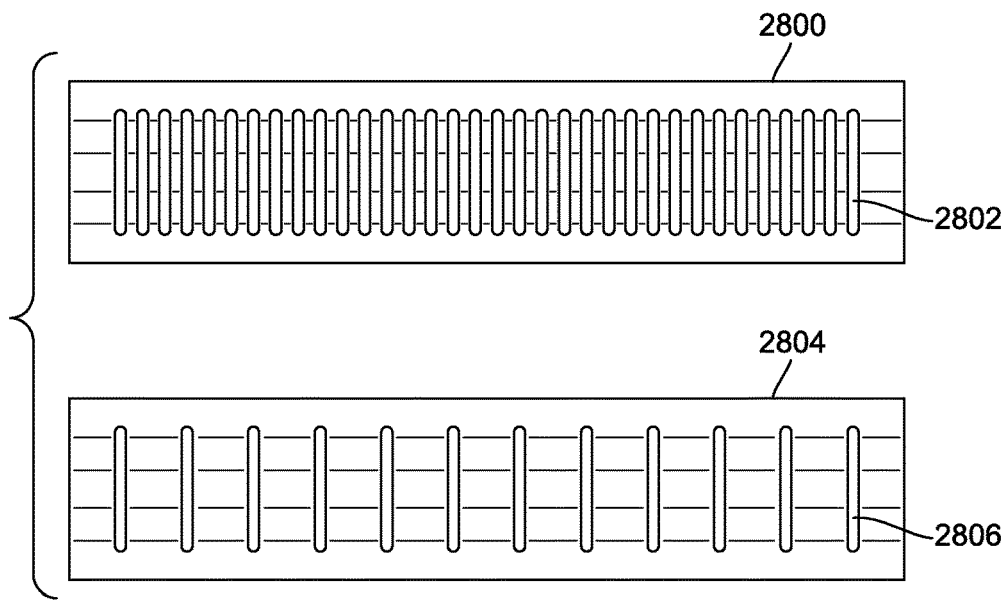
FIG. 32 is a plan view of two preferred embodiments of implant strips with slots with a differing number of slots.

FIG. 32 is a preferred embodiment of first implant strip 2800 and second implant strip 2804. First implant strip 2800 includes first slots 2802 and second implant strip 2804 includes second slots 2806. Preferably, the number of slots comprising first slots 2802 is greater than the number of slots comprising second slots 2806.

Figure 33:
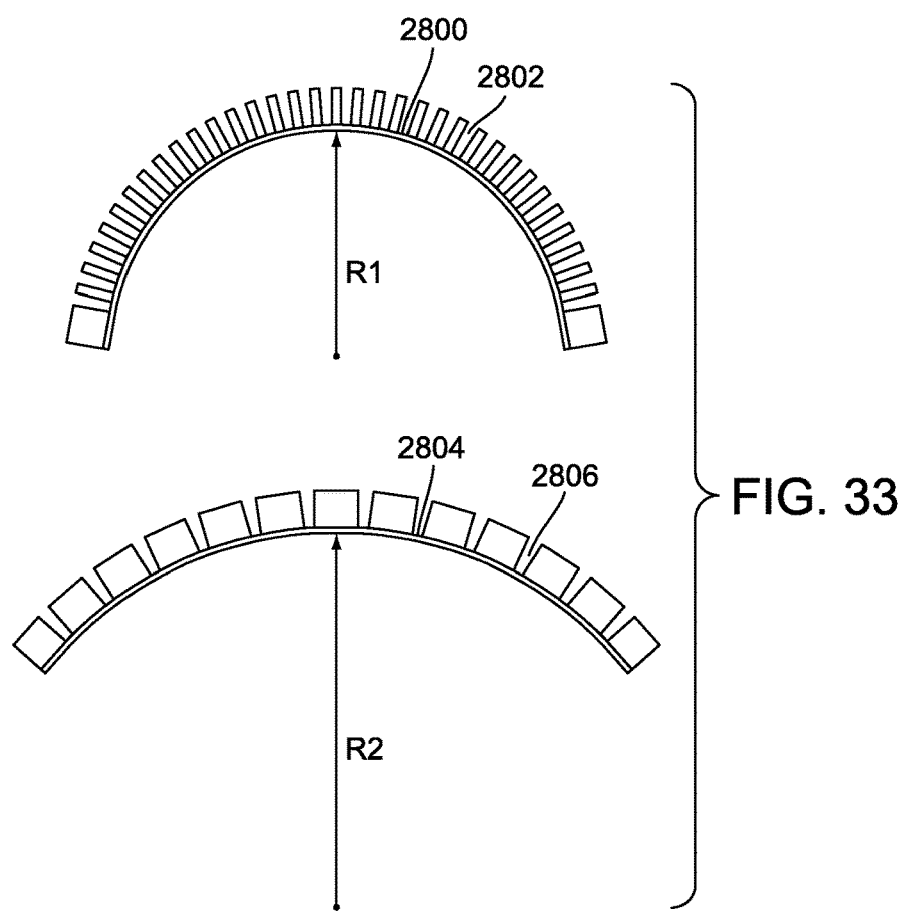
FIG. 33 is a plan view of two preferred embodiments of implant strips with slots undergoing circumferential deflection.

Referring to FIG. 33, first implant strip 2800 and second implant strip 2804 have different deflection characteristics since first implant strip 2800 has a greater number of slots than second implant strip 2804. In this embodiment, first implant strip 2800 can deflect or curve more in the circumferential direction than second implant strip 2804. In particular, first implant strip 2800 has a first radius of curvature R1 than is smaller than a second radius of curvature R2 associated with second implant strip 2804.

By varying the radius of curvature of an implant strip in this manner, the tightness of coiling associated with an implant strip may be varied. Generally, a tighter coil provides more surface area over which to receive axial loads from adjacent vertebrae and thereby increases the strength of the implant strip in the axial direction.

In the previous embodiment, slots of different widths are used to modifying the deflecting properties of an implant strip. In other embodiments, the spacing between slots could vary. In still other embodiments, the orientation of the slots may vary as well. Additionally, in some embodiments, the slots could have different shapes such as oval, round, hexagonal or any type of polygon or irregular shape. These various shapes can be used singularly or in any desired combination.

Figure 34:
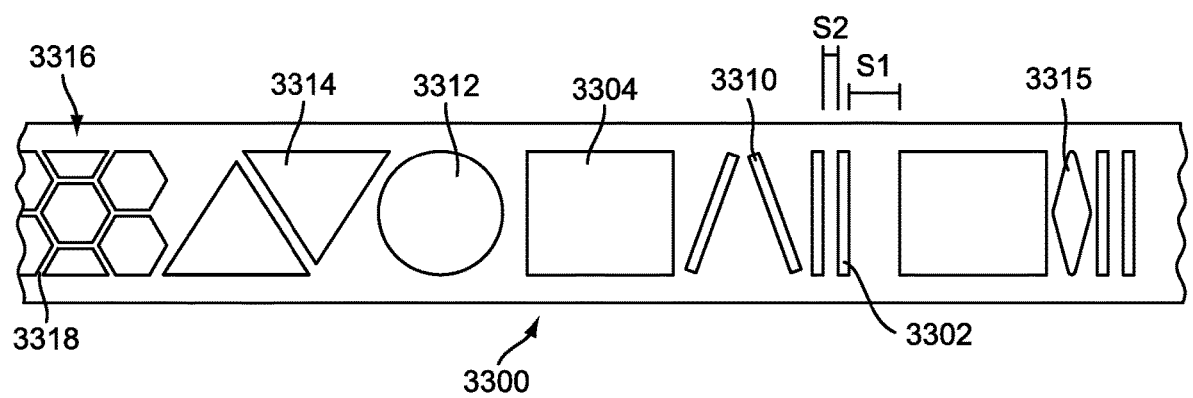
FIG. 34 is a plan view of a preferred embodiment of an implant strip with different slots.

In another embodiment, shown in FIG. 34, a portion of implant strip 3300 includes a variety of punched out shapes configured to change the deflecting characteristics of implant strip 3300. In some embodiments, implant strip 3300 may include thin slots 3302 and wide slots 3304. In this embodiment, the spacing between slots varies from spacing S1 to spacing S2. In this exemplary embodiment, spacing S1 is much larger than spacing S2. In other embodiments, the spacing between slots could be any length, and could vary over implant strip 3300.

In some cases, the orientation of slots could be modified. In some embodiments, implant strip 3300 may include angled slots 3310. Generally, angled slots 3310 may be oriented in any direction, including, in other embodiments, perpendicular to thin slots 3302.

Additional shapes for cutouts are also illustrated in FIG. 34. In some embodiments, implant strip 3300 may include circular cutouts 3312, triangular cutouts 3314, or diamond cutouts 3315. Furthermore, in some cases, the various shapes could be repeating or non-repeating, including various geometric patterns such as honeycomb-like cutouts 3316. In this case, the remaining portions of implant strip 3300 may be configured as lattice 3318.

The various shapes and patterns illustrated in FIG. 34 are only meant to be exemplary. In some embodiments, a single size, shape and spacing for cutouts or slots may be used. In other embodiments, a variety of different shapes for cutouts or slots including regular or irregular spacing between shapes may be used. By using slots or cutouts of varying widths, sizes, orientations and various spacing between slots or cutouts, the deflection properties and the coiling properties of implant strip 3300 may be tuned.

Preferably, implant strips may be configured to permanently deflect in some situations. Generally, vertebrae are not completely symmetric and therefore the spacing between two adjacent vertebrae may vary. Using an implant strip that is configured to partially permanently deflect at some portions allows for a more natural fit of the implant strip.

Figure 35:
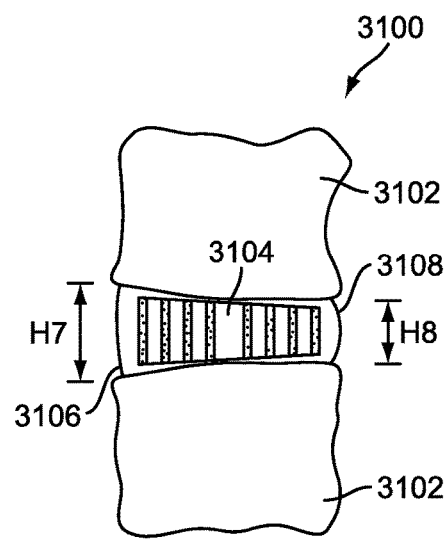
FIG. 35 is a schematic view of a preferred embodiment of an implant strip partially permanently deflecting.

FIG. 35 is a schematic view of a preferred embodiment of a portion of spinal column 3100, including vertebrae 3102. Implant strip 3104 has been inserted between vertebrae 3102 to replace a spinal disc. In this embodiment, the spacing between vertebrae 3102 varies. In particular, at front side 3106 of spinal column 3100, vertebrae 3102 are separated by a height H7 while at rear side 3108 of spinal column 3100, vertebrae 3102 are separated by a height H8 that is less than height H7. Preferably, implant strip 3104 has partially permanently deflected at rear side 3108, allowing for a natural fit. It should be understood that implant strip 3104 has only partially permanently deflected at rear side 3108. Generally, implant strip 3104 is configured to continue axial deflection under increased axial loads at front side 3106 and rear side 3108.

Using the configuration described here, the shape of implant strip 3104 is preferably automatically customized. In some regions between adjacent vertebrae, such as the narrow region discussed above, the implant strip may plastically deform to adjust to natural contours of the adjacent vertebrae. In other regions, such as the wider region discussed above, the implant strip may remain extended or minimally deflected to fully fill in the spaces between vertebrae. In this manner, the implant strip preferably performs a similar function to a spinal disc.

Preferably, an implant strip may include provisions for facilitating coiling of the implant strip during implantation into a spine. In a preferred embodiment, a curved tube may be used to facilitate coiling of an implant strip. The following embodiment is intended to illustrate a provision for facilitating coiling of any type of implant strip. It should be understood that the following procedure may be used to facilitate the implantation of any of the various implant strips discussed earlier as well as other possible implant strips.

Figure 36:
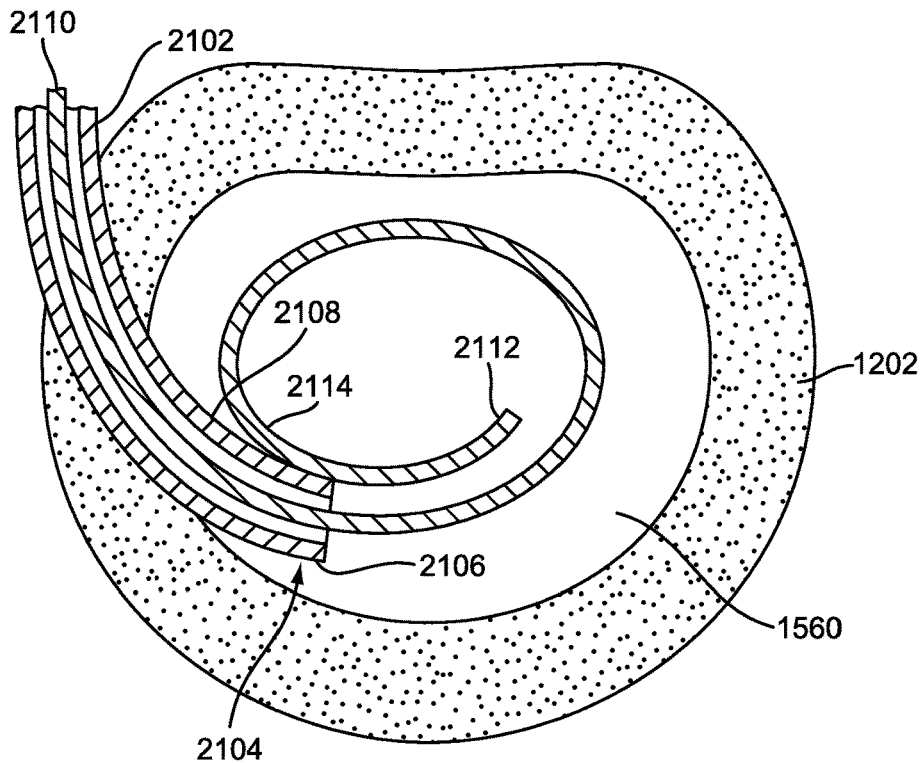
FIG. 36 is a plan view of a preferred embodiment of a delivery device used for facilitating coiling of an implant strip.

FIG. 36 is a preferred embodiment of implant strip 2110 being inserted into cavity 1560 of intervertebral disc 1202. In this embodiment, the insertion of implant strip 2110 is facilitated by delivery device 2102. Delivery device 2102 may be a catheter or similar tube configured for receiving implant strip 2110. Preferably, distal end 2104 of delivery device 2102 is disposed just inside of cavity 1560 and includes curved deforming tip 2106.

As implant strip 2110 is inserted, curved deforming tip 2106 helps facilitate some bending of implant strip 2110 in the circumferential direction. As insertion of implant strip 2110 continues, intermediate portion 2114 of implant strip 2110 is further coiled by inner curved portion 2108 of delivery device 2102. This arrangement further facilitates the coiling of distal end 2112 of implant strip 2110 towards the center of cavity 1560. Using delivery device 2102 allows for increased control of coiling of implant strip 2110 during implantation.

In some embodiments, a spinal implant strip may be used to repair a herniated intervertebral disc. This may be achieved by using similar techniques for removing the herniated portion of the disc. Following this, a spinal implant strip may be inserted into the removed portion of the disc.

Figure 37:
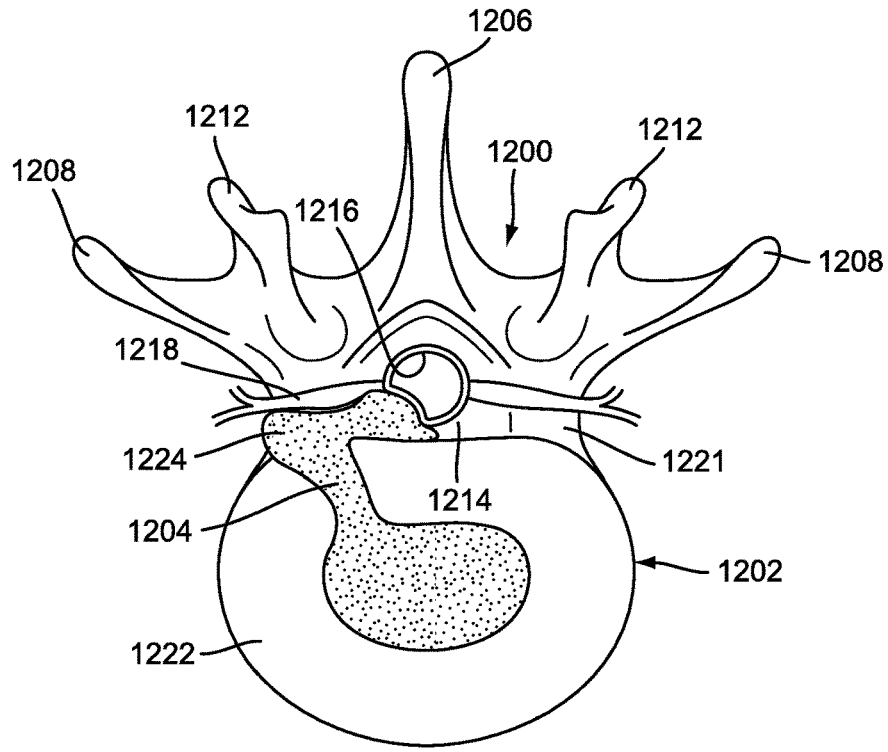
FIG. 37 is a top down view of a preferred embodiment of a herniated intervertebral disc.

FIG. 37 is a plan view similar to that of FIG. 2, illustrating a herniated or traumatized intervertebral disc 1202. As shown, the nucleus pulposus 1224 is protruding from the intervertebral disc 1202 through a cut or flaw 1204 in the intervertebral disc 1202. The protruding nucleus pulposus 1224 impinges on one of the exiting nerves 1218 as well as the spinal cord 1216 or cauda equina.

Figure 38:
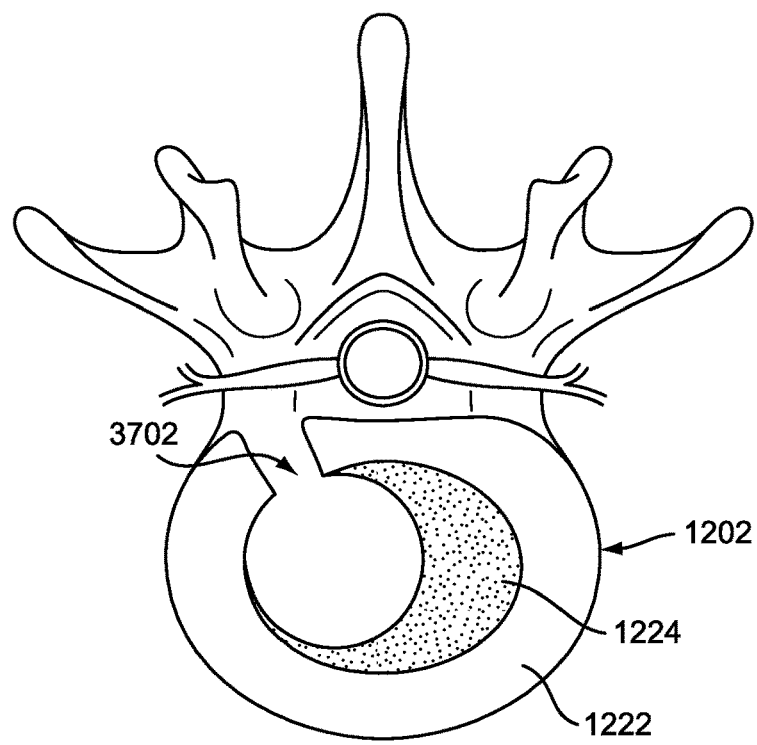
FIG. 38 is a top down view of a preferred embodiment of a herniated disc after partial discectomy.

In cases where an intervertebral disc is herniated, such as is shown here, portions of nucleus pulposus 1224 may be removed, as seen in FIG. 38. This may be achieved using standard surgical techniques or techniques similar to those discussed in the previous embodiments illustrated in FIGS. 6-8. In some cases, a partial discectomy may be also performed through a single tube or double tube. At this point, recess 3702 is left open within disc annulus 1222.

Figure 39:
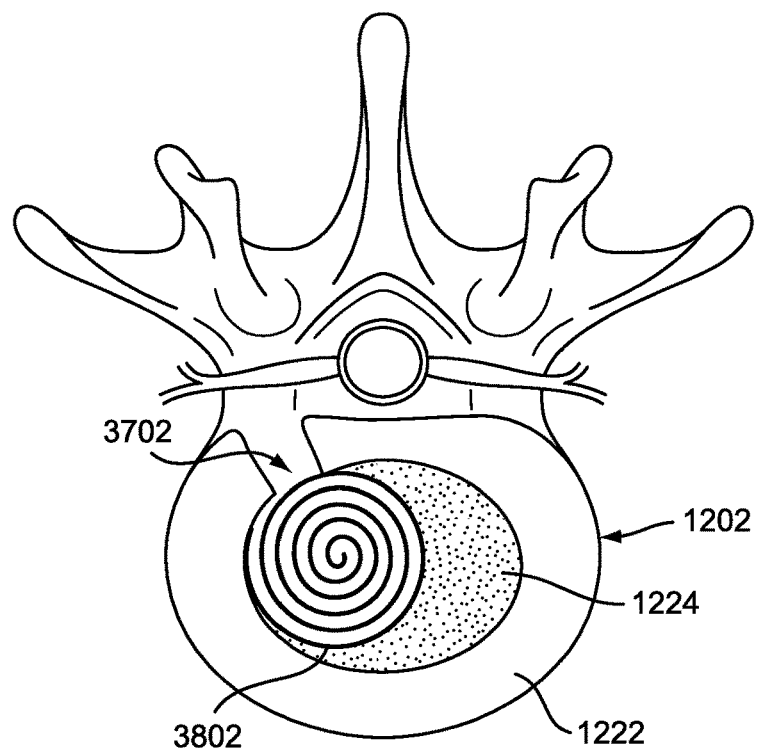
FIG. 39 is a top down view of a preferred embodiment of a herniated disc with an implant strip inserted.

Preferably, implant strip 3802 may be inserted into recess 3702 to repair intervertebral disc 1202, as seen in FIG. 39. This may be accomplished using similar techniques to those previously discussed for implanting a spinal strip illustrated in FIGS. 6-8. As noted in the embodiment shown in FIGS.

6-8, implant strip 3802 may be inserted using a single tube or double tube technique. Using this preferred arrangement, implant strip 3802 may be configured to replicate the mechanical properties of nucleus 1224.

Using the various arrangements for a spinal implant strip discussed in this detailed description provide for improved utility over prior designs. Each of these designs is versatile since various types of implant strips may be used for replacing various kinds of spinal discs. Also, each of these arrangements provides for a single piece device that does not experience the wear or generate particulate debris that may be associated with multi-piece designs. Finally, using the materials and designs discussed in this detailed description, the implant strips are preferably configured to either remain rigid or maintain a general spring-like state without undergoing any fatigue or mechanical failure.

Embodiments of the present invention can provide for continuity of the spine. The term "continuity of the spine" generally refers to the concept of providing an actual mechanical bridge between two distinct vertebral bodies. In some embodiments, this implant device provides for a mechanical bridge, while also allowing motion between the two distinct vertebral bodies. This arrangement can approximate the natural biomechanics of the spine.

By applying principles or features of the present invention, a surgeon can implant a device to restore the original anatomical height of the disk, thereby restoring normal forces across the spine. The surgeon can also select an implant device that can provide decompression of the nerves in the vertebral foramen and canals. This implant device can provide a post-implantation height greater than or less than the original anatomical height of the disk. This implant device can also provide a post-implantation configuration that optimizes the relative position between two vertebrae. In some cases, this post-implantation configuration can be used to correct scoliosis or spondylolisthesis.

In some embodiments, a spinal implant strip may include provisions for embedding into adjacent vertebrae. A spinal implant strip with provisions for attaching to adjacent vertebrae may be useful in disc replacement procedures as well as disc fusion procedures. In other embodiments, an implant strip may include teeth on a periphery of the implant strip to assist in anchoring an implant strip to adjacent vertebrae. In some cases, teeth on a periphery of an implant strip may facilitate bone growth into the implant strip following implantation. By increasing the surface area on a periphery of an implant strip, teeth may facilitate bone growth into the implant strip.

FIGS. 40-43 are preferred embodiments of spinal implant strips with teeth disposed on a periphery of the implant strips. For the purpose of clarity, the implant strips are illustrated schematically. Typically, an implant strip will have a much greater length than the implant strips illustrated in these Figures. Preferably, the implant strips in these embodiments may be inserted in an identical manner to the methods used to insert the previously discussed implant strips of the previous embodiments.

Generally, teeth may be disposed on any portion of a periphery of an implant strip. In some embodiments, an implant strip may include teeth on a lower edge. In some cases, teeth may be disposed on a portion of a lower edge. In other cases, teeth may be disposed on an entirety of a lower edge. In other embodiments, an implant strip may include teeth on an upper edge. In a preferred embodiment, an implant strip may include teeth on an entirety of both a lower edge and an upper edge. Additionally, teeth may be disposed along an entirety of the length of an implant strip, or just a portion of an implant strip. By using different configurations of teeth along an implant strip, an implant strip can be embedded in various ways between two adjacent vertebrae.

Throughout the remainder of this detailed description and in the claims, the terms "upper edge" and "lower edge" generally refer to edges of an implant strip that extend in a longitudinal direction between a first end and a second end of the strip. In particular, the upper edge is configured to contact a vertebrae disposed above a coiled implant strip, while the lower edge is configured to contact a vertebrae disposed below a coiled implant strip.

Figure 40:
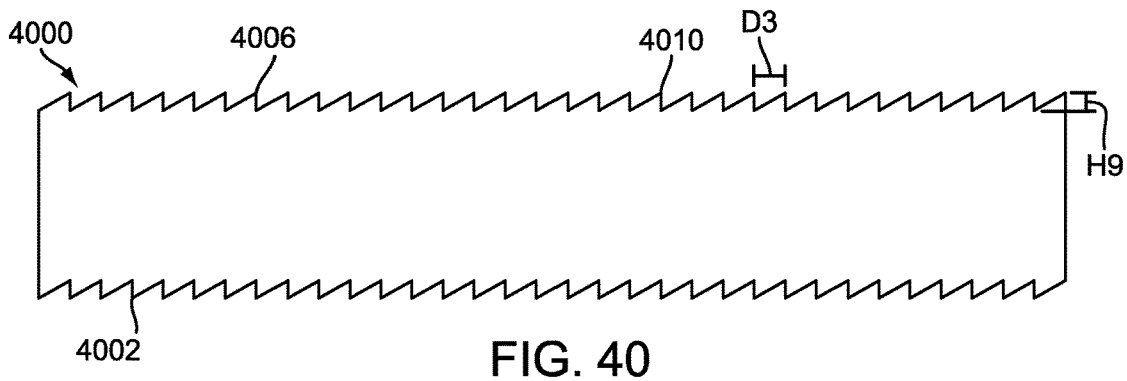
FIG. 40 is a plan view of a preferred embodiment of an implant strip with teeth disposed in a saw tooth pattern on an upper and lower edge.
Figure 41:
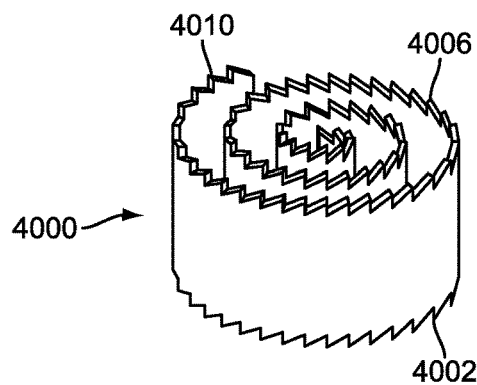
FIG. 41 is an isometric view of a preferred embodiment of an implant strip coiled with a saw tooth pattern on an upper and lower edge.

FIGS. 40-41 illustrate an exemplary embodiment of implant strip 4000. In these embodiments, implant strip 4000 includes lower edge 4002 and upper edge 4006. Lower edge 4002 and upper edge 4006 form a portion of a periphery of implant strip 4000. In this embodiment, lower edge 4002 and upper edge 4006 are configured with teeth 4010 disposed in a downward and upward direction, respectively.

Typically, teeth may be configured in any shape and size. For example, in some cases, teeth may have an approximately symmetrical shape. In other cases, teeth may have a saw tooth orientation. In still other cases, teeth may be rounded.

Various configurations of teeth may be included on an implant strip. In some embodiments, teeth may conform to a repeating pattern. In some cases, for example, smaller teeth may be interspersed between larger teeth. In other embodiments, teeth may be identical in size and shape. In other embodiments, teeth may be disposed in different shapes and sizes on a periphery of an implant strip without a recognizable pattern in an attempt to customize an implant strip to the anatomical shape of vertebrae adjacent to the insertion site. In still other embodiments, teeth may be configured in multiple patterns on a periphery of an implant strip. For example, teeth disposed on an upper edge of an implant strip may be identical, while teeth disposed on a lower edge may be a repeating pattern of smaller teeth interspersed between larger teeth.

In addition to teeth, embodiments of an implant strip may be configured with other provisions to encourage bone growth into the implant strip. These provisions may be applied to any desired portion of the implant strip. Generally, in any of the embodiments discussed in this detailed description, a combination of macroscopic holes and microscopic holes or other bone growth promoting surface treatments can be used. By using a combination of both features, bone growth can be encouraged at the surface of the implant strip so that the implant strip, on a surface level, integrates with the bone; and by using macroscopic holes, large scale or bulk integration of the prosthesis can occur, further solidifying the integration of the implant strip with the bone. Details of these provisions can be found in U.S. Patent Publication Number US 2009/0048675 (U.S. patent application Ser. No. 11/840,707, filed on Aug. 17, 2007, entitled "Spinal Fusion Implants with Selectively Applied Bone Growth Promoting Agent"), the entirety of which is incorporated by reference herein.

In the current embodiment, teeth 4010 are substantially identical with the same size and shape. In particular, teeth 4010 are configured in a saw tooth orientation. Specifically, teeth 4010 extend height H9 from base to apex. Furthermore, teeth 4010 are regularly spaced on edges 4002 and 4006 and are separated by a distance D3 between apexes of consecutive teeth 4010. Generally, height H9 and distance D3 may have any values and may vary from one embodiment to another. In this embodiment, teeth 4010 are tightly spaced and distance D3 is approximately the same as height H9 of teeth 4010.

FIG. 41 is an exemplary embodiment of implant strip 4000 after implant strip 4000 has been coiled. In some embodiments, implant strip 4000 may be pre-formed and coiled prior to implantation. Generally, any of the embodiments discussed in this detailed description may be coiled prior to implantation. For example, a surgeon may receive a preformed coiled implant strip for implantation in some cases. For example, an implant strip may be shaped into a preformed coil according to various particular features of a particular patient or the desires of the surgeon. In other embodiments, as discussed previously implant strip 4000 may coil as implant strip 4000 is implanted.

Upon implantation, teeth 4010 preferably extend upward and downward to engage adjacent vertebrae. Preferably, using this arrangement, teeth 4010 facilitate the in-growth of bone from adjacent vertebrae. In this manner, teeth 4010 may help embed implant strip 4000 into adjacent vertebrae.

Generally, teeth on a periphery of an implant strip may be regularly or irregularly spaced. In some embodiments, portions of a periphery may include teeth that are regularly spaced, while other portions of a periphery may include teeth that are irregularly spaced. In some cases, a surgeon may consider particular anatomical characteristics of a site where an implant strip is to be inserted when choosing an implant strip with regularly spaced or irregularly spaced teeth.

Figure 42:
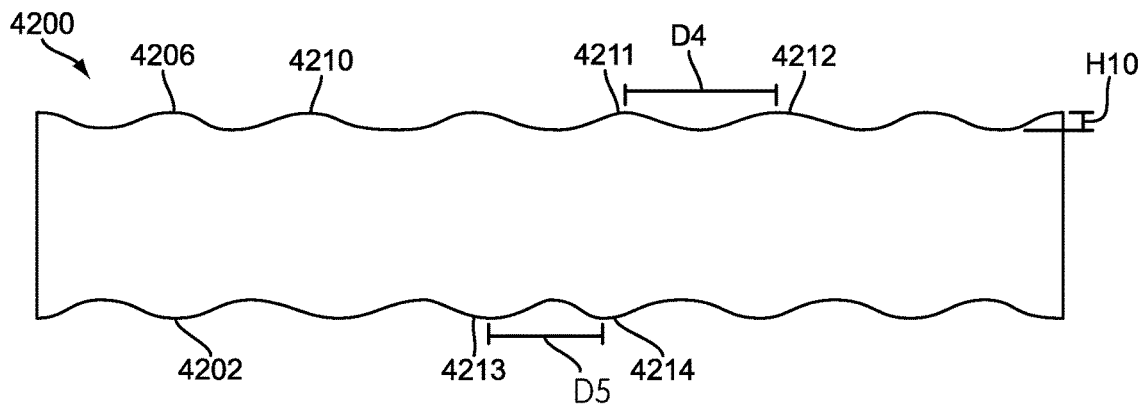
FIG. 42 is a preferred embodiment of an implant strip with rounded irregularly spaced teeth disposed on an upper and lower edge.
Figure 43:
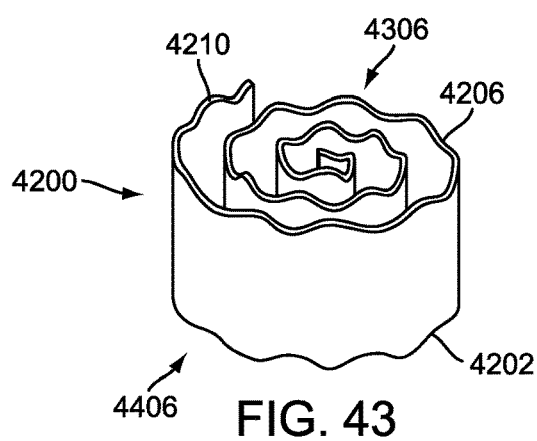
FIG. 43 is an isometric view of a preferred embodiment of an implant strip coiled with rounded irregularly spaced teeth disposed on an upper and lower edge.

FIGS. 42 and 43 illustrate an exemplary embodiment of implant strip 4200 with teeth 4210 spaced irregularly. In this embodiment, a periphery of implant strip 4200 includes lower edge 4202 and upper edge 4206. Teeth 4210 are disposed on the entirety of both edges 4202 and 4206. In this embodiment, teeth 4210 are configured with a rounded shape. Furthermore, the rounded shape of teeth 4210 includes a relatively low profile with an approximate height H10 at the apex. In some cases, the rounded shape of teeth 4210 may prevent burrs and shorten the healing time after the implantation of implant strip 4200.

While teeth 4210 include a rounded shape on edges 4202 and 4206, teeth 4210 are not identical due to irregular spacing. For example, apexes of consecutive first tooth 4211 and second tooth 4212 disposed on upper edge 4206 are separated by distance D4. In contrast, apexes of consecutive third tooth 4213 and fourth tooth 4214 on lower edge 4202 are separated by distance D5 that is less than distance D4. In this embodiment, the spacing between teeth 4210 is irregular and varies between consecutive teeth.

FIG. 43 illustrates an exemplary embodiment of implant strip 4200 coiled. In some cases, implant strip 4200 may be pre-formed prior to implantation. In other cases, implant strip 4200 may coil as implant strip 4200 is inserted. Preferably, teeth 4210 on lower edge 4202 and upper edge 4206 provide increased surface area to engage adjacent vertebrae and augment bone growth. Additionally, by spacing teeth 4210 irregularly on a periphery of implant strip 4200, top surface 4306 and bottom surface 4406 may be configured to present a desired shape to adjacent vertebrae as implant strip 4200 is coiled. In some cases, teeth 4210 may engage and provide support to adjacent vertebrae, while spacing between teeth 4210 may encourage the in-growth of bone and the attachment of implant strip 4200 to adjacent vertebrae.

Preferably, in the embodiments illustrated in FIGS. 40-43, teeth may be formed by cutting or removing portions of an implant strip. Cutting may be done using techniques known in the art, including, but not limited to, punching, laser fusion and/or water drilling, stamping, or any combination of techniques. In other embodiments, teeth may be formed using a die of some kind. Techniques are preferably used to create smooth edges on the teeth in order to prevent burrs. With this arrangement, scar tissue due to burrs may be substantially reduced following the implantation of the implant strips. In still other embodiments, however, techniques may be employed that leave burrs intact so that the remaining burrs facilitate in-growth of bone.

An implant strip may employ various provisions to prevent or limit contact between adjacent coils when the implant strip is coiled. In some cases, increasing the space between adjacent coils may reduce or substantially eliminate rubbing that may create particulate debris. In other cases, the creation of space between adjacent coils may enhance in-growth of bone into an implant strip. In still other cases, spacing of adjacent coils may allow a coiled implant strip to mimic the dynamic properties of an intervertebral disc.

Generally, an implant strip may be configured to coil in a manner that prevents or limits contact between all adjacent coils, a specific set of adjacent coils, or a portion of the coil of adjacent coils. In some embodiments, a coiled implant strip may be configured to prevent contact between a first set of coils, but allow contact between a second set of coils. In other embodiments, adjacent coils may be configured to be separated by a first distance on a first surface of an implant strip and separated by a second distance, different from a first distance, on a second surface of an implant strip. For example, in some cases, adjacent coils may be spaced apart on a top surface of a coiled implant strip, but adjacent coils on a bottom surface may coil tightly without space between adjacent coils. In a preferred embodiment, an implant strip may include identical spacing between all adjacent coils.

FIGS. 44-49 are exemplary embodiments of implant strips with provisions to prevent contact between adjacent coils. For the purpose of clarity, the implant strips in these embodiments are illustrated schematically. Typically, an implant strip will have a much greater length. Also, the implant strips in these embodiments may be inserted in an identical manner to the methods used to insert the previously discussed implant strips. In particular, the implant strips in these embodiments may coil during implantation or as previously discussed, may be pre-formed into a coil for implantation. Furthermore, the implant strips in these embodiments may include features discussed in any of the embodiments in this detailed description.

Generally, an implant strip may include one or more separating portions. The term "separating portion" as used throughout this detailed description and in the claims refers to any provision for separating adjacent coils of an implant strip. Separation portions may be configured on an implant strip in any manner known in the art. In some embodiments, separating portions may be integrally formed with an implant strip. In some cases, separating portions may be created by deforming portions of an implant strip. For example, separating portions may be formed by forcing portions of a first surface upward to create protrusions on an inner surface disposed opposite of the outer surface. Such a method of creating protrusions may also provide divots or recesses on a second opposing surface. In other embodiments, separating portions may be applied to an implant strip separately. In some cases, the separating portions could be integrally molded with the implant strip. In other cases, the separating portions could be bonded or attached to the implant strip.

Figure 44:
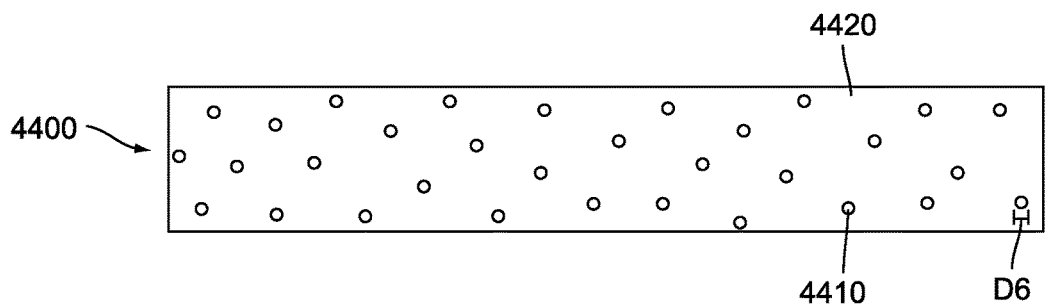
FIG. 44 is a plan view of an exemplary embodiment of an implant strip with protrusions.
Figure 45:
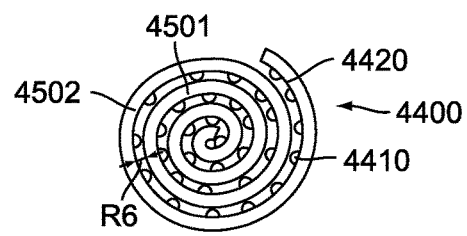
FIG. 45 is a plan view of an exemplary embodiment of a coiled implant strip with protrusions.

Referring to FIGS. 44-45, implant strip 4400 is configured with protrusions 4410. Protrusions 4410 are disposed on inner surface 4420 of implant strip 4400. In particular, protrusions 4410 thrust outward from inner surface 4420. In this embodiment, protrusions 4410 are substantially similar and shaped as half spheres. In addition, protrusions 4410 are irregularly and rather widely spaced. Specifically, the spacing between protrusions 4410 is relatively greater than diameter D6 of protrusions 4410.

Generally, protrusions may have different shapes such as oval, hexagonal, rectangular, or any type of polygon or irregular shape. These various shapes can be used singularly or in any desired combination. By using different shapes, size and spacing, the deflection properties and the coiling properties of an implant strip may be tuned. Typically, a tighter coil provides more surface area over which to receive axial loads from adjacent vertebrae and thereby increases the strength of the implant strip in the axial direction.

When implant strip 4400 is coiled, either prior to implantation or during implantation, protrusions 4420 create spacing between adjacent coils, as seen in FIG. 45. In particular, first inner coil 4501 and second outer coil 4502 are spaced apart by a radial distance R6. Generally, radial distance R6 may have any value and vary from one embodiment to another. In this embodiment, radial distance R6 is approximately equal to the height of protrusions 4410. Furthermore, when implant strip 4400 forms a coil, all coils of implant strip 4400 will be separated by radial distance R6, since protrusions 4410 are identical. With this preferred arrangement, adjacent coils may not rub and create particulate debris. In addition, due to the spacing between protrusions 4410, bone from adjacent vertebrae may grow between adjacent coils to secure implant strip 4400 in position.

In some embodiments, bone may be encouraged to grow between adjacent coils by the application of a material. Generally, any type of material may be applied including, but not limited to polymers, polymers embedded with biological matrices, bone growth promoting agent, or any biocompatible material. Furthermore, the material may be applied to an entirety or a portion of implant strip 4400 using any method known in the art. In some cases, biological matrices, bone growth promoting agent, or another biocompatible material may be applied in a sponge application. Also, the bone growth promoting agent could be applied in as a paste in, for example, a "peanut butter" type application.

While this embodiment includes protrusions disposed on an inner surface of an implant strip, other embodiments may include protrusions or other provisions for spacing on an outer surface opposite of the inner surface. In some embodiments, provisions for spacing may be included on both an outer and inner surface of an implant strip. Generally, protrusions or other provisions for spacing disposed on both surfaces will increase the distance separating adjacent coils when an implant strip is coiled.

Figure 46:
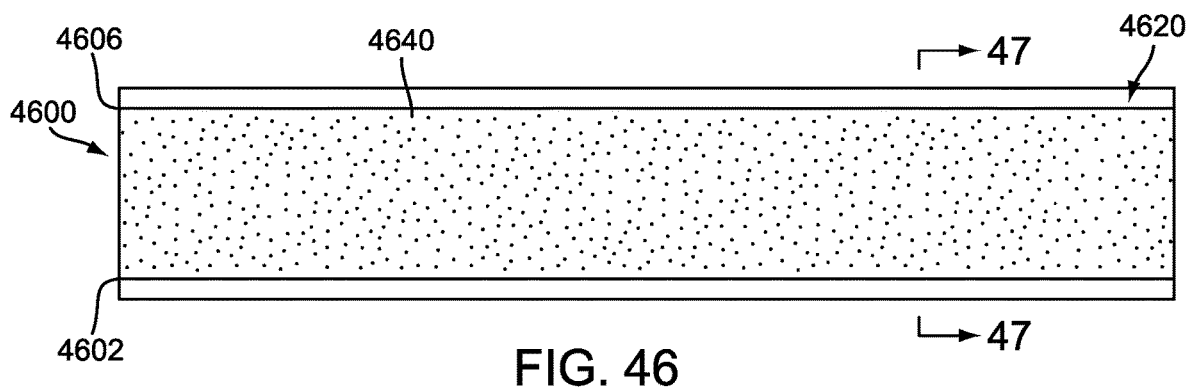
FIG. 46 is a plan view of an exemplary embodiment of polymer applied to an implant strip.
Figure 47:
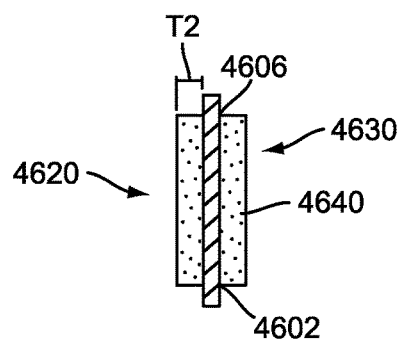
FIG. 47 is a cross sectional view of an exemplary embodiment of an implant strip with an application of polymer.

FIGS. 46-49 illustrate an exemplary embodiment of implant strip 4600 configured to coil in a manner that prevents contact between adjacent coils. Preferably, implant strip 4600 includes inner surface 4620 and outer surface 4630 disposed opposite of inner surface 4620. In this embodiment, material 4640 is applied to a portion of inner surface 4620 and outer surface 4630, as seen in FIG. 47. In particular, material 4640 is applied to cover regions on surfaces 4620 and 4630 between upper boundary 4606 and lower boundary 4602.

Generally, material 4640 may have any desired thickness to provide a desired separation between adjacent coils. In this embodiment, material 4640 is applied with thickness T2. With this preferred arrangement, material 4640 creates space between adjacent coils when implant strip 4600 is coiled.

Any type of material may be applied to an implant strip, including, but not limited to, polymers embedded with biological matrices, bone growth promoting agent, or any biocompatible material. In addition, the material may be applied to an implant strip in any manner known in the art. In some embodiments, the material may be applied in a pattern. In some cases, the material could be applied in a regular pattern. In other cases, the material may be applied in an irregular pattern. Generally, a material may be applied with varying levels of thickness to any portion of an implant strip. In some embodiments, a material may be applied to produce a particular spacing between adjacent coils of an implant strip.

Figure 48:
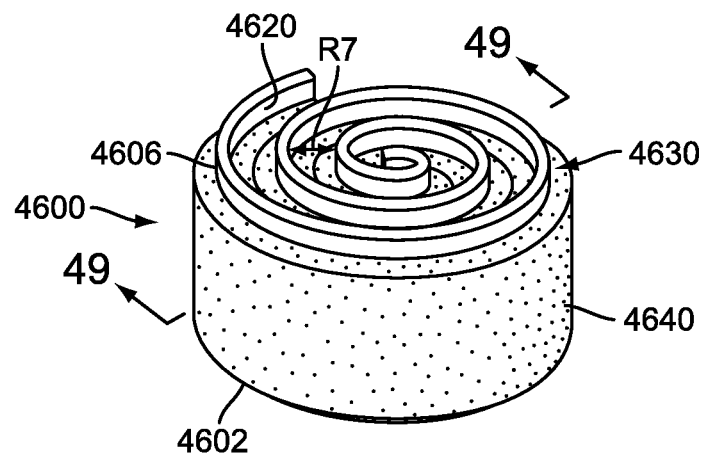
FIG. 48 is an isometric view of an exemplary embodiment of a coiled implant strip with an application of polymer.

Referring to FIG. 48, implant strip 4600 may be preformed and inserted or coiled during insertion. By applying material 4640 on both surfaces 4620 and 4630, coils of implant strip 4600 may be spaced apart a radial distance R7. Generally, radial distance R7 may be related to thickness T2. In this embodiment, radial distance R7 is two times thickness T2, since material 4640 is applied to both surface 4620 and 4630 of implant strip 4600. Using this preferred arrangement, adjacent coils of implant strip 4600 are spaced to prevent contact with one another when implant strip 4600 is formed into a coil.

Preferably, portions of implant strip 4600 extend above and below upper boundary 4606 and lower boundary 4602, respectively (see FIG. 46). This arrangement provides for the upper and lower edges of implant strip 4600 to contact adjacent vertebrae directly. In particular, this arrangement may facilitate implantation of implant strip 4600 into adjacent vertebrae. In some cases, the lower and upper edges may also be modified to include teeth or similar provisions for facilitating implantation.

Figure 49:
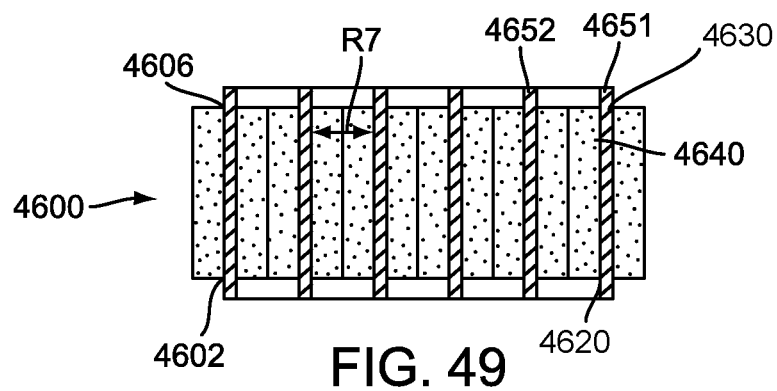
FIG. 49 is a cross sectional view of an exemplary embodiment of a coiled implant strip with an application of polymer.

Furthermore, since material 4640 is not applied to the entirety of surfaces 4620 and 4630, spaces or gaps may be created between adjacent radially spaced coils. In particular, portions of coiled implant strip 4600 above upper boundary 4606 and below lower boundary 4602 may include spaces, as seen in FIGS. 48-49. This arrangement may spur bone growth between the coils of implant strip 4600. In other embodiments, boundaries 4606 and 4602 may be adjusted to alter the size of gaps or spaces between adjacent coils. This feature may be particularly useful during procedures involving disc fusion as well as disc replacement by engaging adjacent vertebrae and facilitating bone growth into implant strip 4600.

Generally, a material may be used to help create separating portions for any type of implant strip. In the current embodiment, a material is applied to a substantially flat implant strip. However, in other embodiments, a material could be applied to other implant strips with different shapes. In some embodiments, a material can be applied to an implant strip with provisions for deflecting and/or deforming to endure bending, lateral, axial, and twisting forces. In some cases, separating portions may be applied to an implant strip to prevent the growth of bone into portions of the coiled implant strip.

Figure 72:
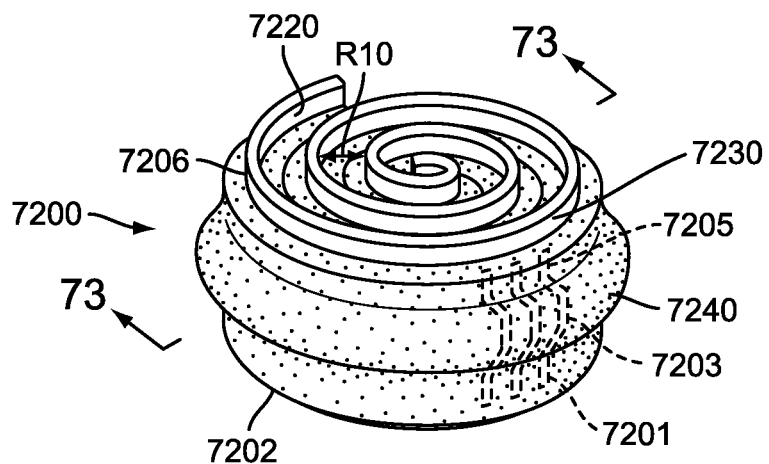
FIG. 72 is an isometric view of an exemplary embodiment of a coiled implant strip with slots and an application of polymer.
Figure 73:
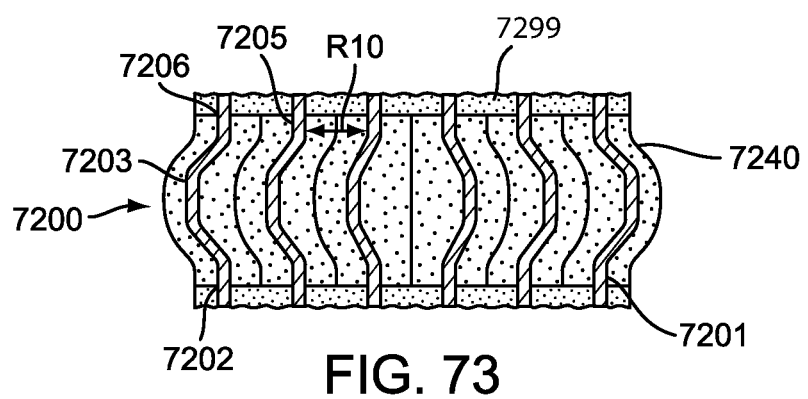
FIG. 73 is a cross sectional view of an exemplary embodiment of a coiled implant strip with slots and an application of polymer.
Figure 74:
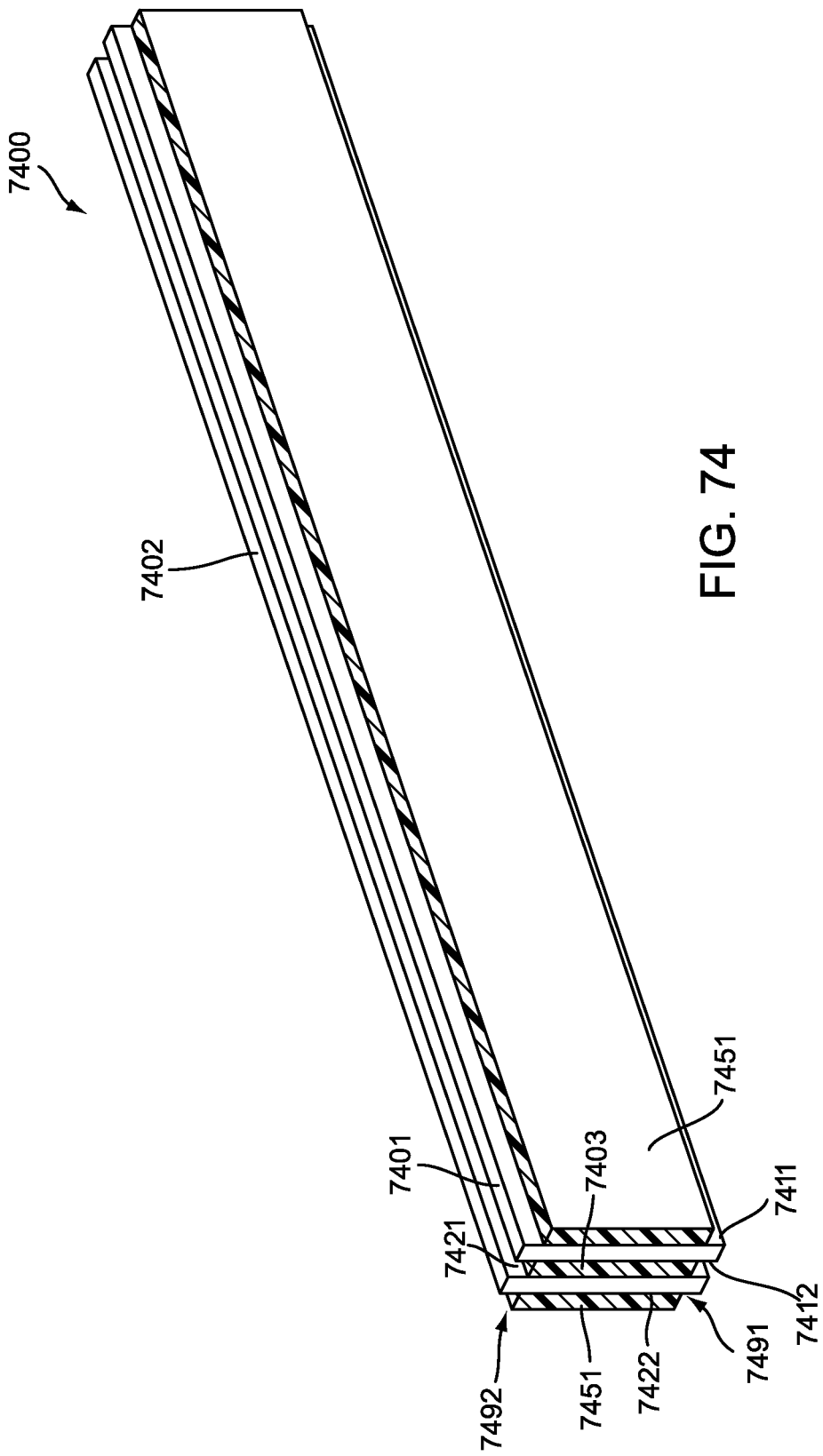
FIG. 74 is an isometric view of an exemplary embodiment of an implant strip comprised of two implant strips, a spacer portion and an application of polymer.

FIGS. 72-73 illustrate an exemplary embodiment of coiled implant strip 7200. In this embodiment, implant strip 7200 is configured to accommodate deflection in the axial direction. Preferably, implant strip 7200 is substantially similar to implant strip 2300 as seen in FIGS. 26-31. In particular, implant strip 7200 preferably includes protruding portion 7203 (a portion of which is shown in FIG. 72 in phantom) that extends outward from, and is preferably joined with, upper side 7205 and lower side 7201. With this arrangement, protruding portion 7203 may compress under axial loads.

In addition, implant strip 7200 may be configured with material 7240 that acts as a separating portion. In a similar manner to the previous embodiment, implant strip 7200 includes material 7240 that is applied to a portion of inner surface 7220 and outer surface 7230 of implant strip 7200. Specifically, material 7240 is applied to cover regions of inner surface 7220 and outer surface 7230 between upper boundary 7206 and lower boundary 7202. Preferably, protruding portion 7203 is disposed between upper boundary 7206 and lower boundary 7202. In this manner, material 7240 may cover protruding portion 7203 and prevent the growth of bone into protruding portion 7203.

In some embodiments, material 7240 may alter the deflection properties of implant strip 7200 when material 7240 covers protruding portion 7203. In some cases, material 7240 may decrease the flexibility of protruding portion 7203. In other embodiments, material 7240 may be configured with material properties that do not interfere with the deflection properties of implant strip 7200.

Referring to FIG. 72, implant strip 7200 may be preformed in some embodiments. In other embodiments, implant strip 7200 may be coiled during insertion. In this embodiment, coils of implant strip 7200 may be spaced apart by radial distance R10 by the application of material 7240 on inner surface 7220 and outer surface 7230. Since material 7240 is not applied to the entirety of inner surface 7220 and outer surface 7230, bone 7299 may grow into spaces between adjacent radially spaced coils above upper boundary 7206 and below lower boundary 7202. This arrangement preferably facilitates the attachment of implant strip 7200 to bone.

Referring to FIG. 73, a cross section of coiled implant strip 7200 may be clearly seen with protruding portion 7203 providing a flexible core for implant strip 7200. With material 7240 applied to implant strip 7200, the growth of bone 7299 between adjacent coils is blocked at upper boundary 7206 and lower boundary 7202. This arrangement prevents bone 7299 from contacting protruding portion 7203 and interfering with the deflection properties of protruding portion 7203.

Generally, the thickness of an implant strip will impact the diameter of the coiled implant strip. Typically, a thinner implant strip will require a greater length to achieve the same diameter when coiled as a thicker implant strip. In other words, a thicker implant strip may have a shorter length but form a coiled shape with approximately the same diameter as a longer and thinner implant strip. In some cases, a thicker implant strip with a shorter length may be preferable because it does not require as many coils to achieve a coiled shape with a particular diameter. Furthermore, a thicker implant strip with a shorter length may be easier to store than a thinner implant strip with a longer length.

The thickness of an implant strip may be increased in any manner known in the art. In some embodiments, an implant strip may be constructed with a greater thickness. In other embodiments, an implant strip may be configured with greater thickness by adding distinct portions to an implant strip. In some cases, multiple implant strips may be layered together to create a single layered implant strip with an increased thickness over a single implant strip. Preferably, every pair of adjacent implant strips in a layered implant strip may be separated by a spacer portion.

Figure 66:
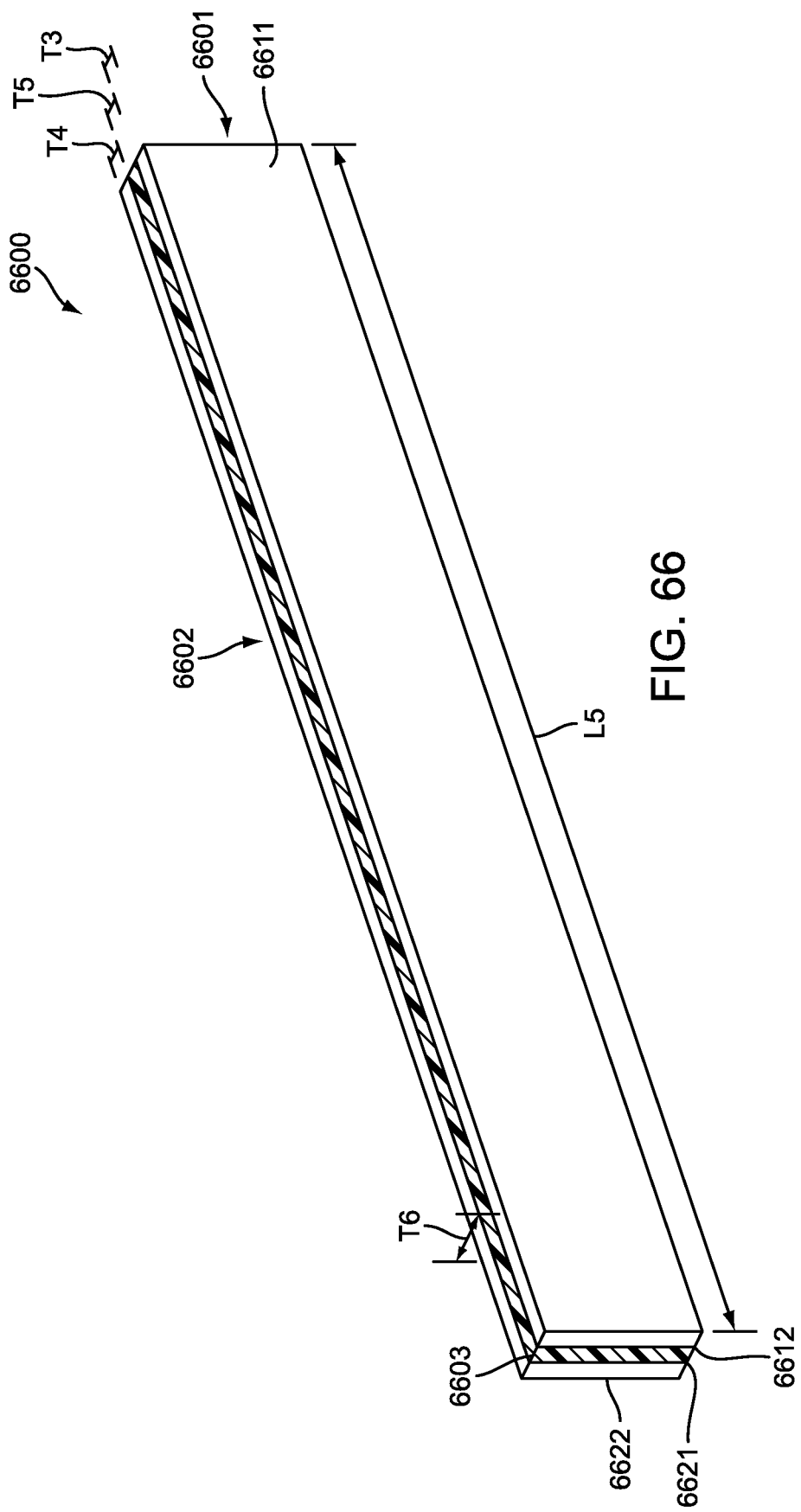
FIG. 66 is an isometric view of an exemplary embodiment of an implant strip comprised of two implant strips and a spacer portion.
Figure 67:
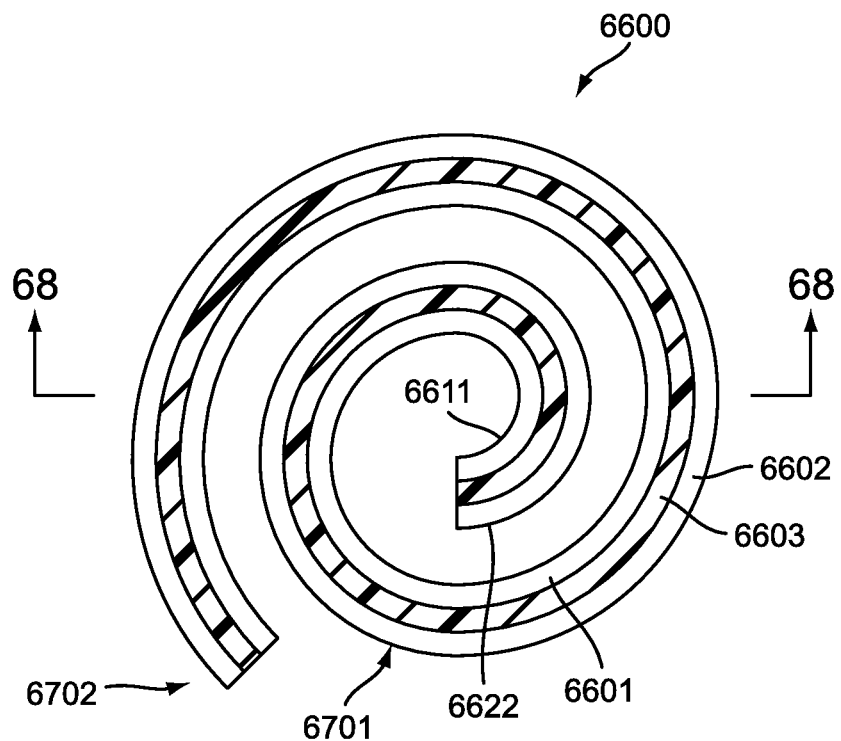
FIG. 67 is a top down view of an exemplary embodiment of a coiled implant strip comprised of two implant strips and a spacer portion.
Figure 68:
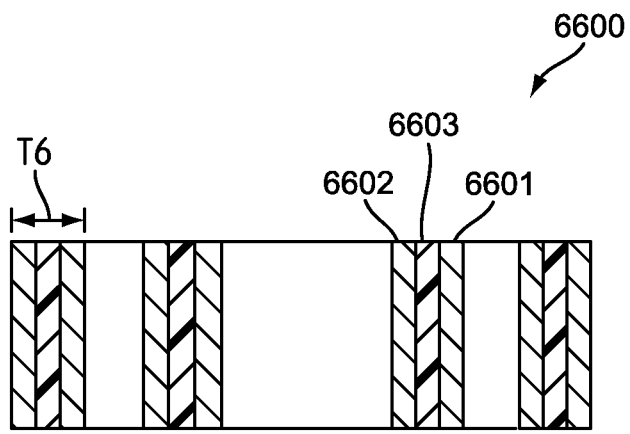
FIG. 68 is a cross sectional view of an exemplary embodiment of a coiled implant strip comprised of two implant strips and a spacer portion.

FIGS. 66-68 illustrate an exemplary embodiment of dual implant strip 6600. Although this embodiment is illustrated schematically, it should be understood that dual implant strip 6600 is configured with length L5 that is shorter than the typical length of thinner implant strips. Furthermore, dual implant strip 6600 is configured with thickness T6 that is greater than the typical thickness of longer implant strips. In order to achieve greater thickness T6, dual implant strip 6600 is configured with layered implant strips.

In particular, dual implant strip 6600 is comprised of first implant strip 6601 and second implant strip 6602. In this exemplary embodiment, first implant strip 6601 is configured with thickness T3. Likewise, second implant strip 6602 is configured with thickness T4. In addition, first implant strip 6601 includes inner surface 6611 and first central surface 6612 disposed opposite of inner surface 6611. In a similar manner, second implant strip 6602 includes second central surface 6621 and outer surface 6622 disposed opposite of second central surface 6621.

Generally, multiple implant strips may be joined in any manner to create a thicker implant strip. In some cases, multiple implant strips may be attached directly to each other. In other cases, multiple implant strips may be joined with another material disposed between the implant strips.

In this exemplary embodiment, dual implant strip 6600 includes spacer portion 6603. Spacer portion 6603 is disposed between first implant strip 6601 and second implant strip 6602. Specifically, spacer portion 6603 attaches to first central surface 6612 of first implant strip 6601. In a similar manner, spacer portion 6603 attaches to second central surface 6621 of second implant strip 6602. With this arrangement, dual implant strip 6600 is configured with thickness T6 that is approximately equal to the sum of thickness T3, thickness T4 and thickness T5 of spacer portion 6603.

Generally, spacer portion 6603 may be constructed of any material discussed in this detailed description. In some cases, spacer portion 6603 may be constructed of a flexible plastic to provide flexibility to dual implant strip 6600. In other cases, spacer portion 6603 may be constructed of shape memory alloy or shape-memory material to assist dual implant strip 6600 in coiling into a desirable shape following implantation.

Preferably, thickness T6 and length L5 of dual implant strip 6600 allow dual implant strip 6600 to form a coiled shape with fewer coils. FIG. 67 is a schematic top down view of an exemplary embodiment of dual implant strip 6600 formed in a coiled shape. Due to thickness T6 and length L5, dual implant strip 6600 forms two coils when shaped in a coil. In particular, dual implant strip 6600 is configured with first coil 6701 and second coil 6702. For illustrative purposes, only two coils are shown here, however it should be understood that in other embodiments dual implant strip 6600 may form additional coils as well.

Referring to FIG. 68, a cross section of coiled dual implant strip 6600 may be clearly seen with spacer portion 6603 disposed between first implant strip 6601 and second implant strip 6602. By forming a coiled shape with fewer coils, dual implant strip 6600 may be easier to implant than a longer thinner strip. Furthermore, the construction of dual implant strip 6600 with spacer portion 6603, as well as first implant strip 6601 and second implant strip 6602, provides opportunities to manipulate the coiling properties of dual implant strip 6600.

In some cases, a dual implant strip may include provisions to facilitate bone growth into the implant strip. Generally, the growth of bone into a dual implant strip may be encouraged in any manner known in the art. In some embodiments, teeth may be disposed on edges of the dual implant strip to facilitate bone growth into the dual implant strip. In other embodiments, bone growth promoting agent may be applied to portions of the dual implant strip to assist bone growth into the dual implant strip. In still other embodiments, a coiled dual implant strip may be configured with recesses or gaps so that bone may grow into the recesses and anchor the dual implant strip. In some cases, a dual implant strip may be configured with a spacer portion and separating portions that create space for the growth of bone into the coiled implant strip.

FIGS. 74-77 illustrate an exemplary embodiment of dual implant strip 7400. As discussed in the previous embodiment, an implant strip may be comprised of multiple implant strips to create a single thicker implant strip that requires fewer coils to achieve a coiled shape with a particular diameter. In this embodiment, dual implant strip 7400 comprises first implant strip 7401 and second implant strip 7402. First implant strip 7401 and second implant strip 7402 may be configured with any width typical for an implant strip. In addition, first implant strip 7401 includes inner surface 7411 and first central surface 7412 disposed opposite of inner surface 7411. Similarly, second implant strip 7402 includes second central surface 7421 and outer surface 7422 disposed opposite of second central surface 7421.

Preferably, first implant strip 7401 is joined to second implant strip 7402 by spacer portion 7403. Specifically, spacer portion 7403 attaches to a portion of first central surface 7412 of first implant strip 7401. Also, spacer portion 7403 attaches to a portion of second central surface 7421 of second implant strip 7402. In order to create space for the growth of bone, spacer portion 7403 preferably extends from upper boundary 7492 to lower boundary 7491 on first implant strip 7401 and second implant strip 7402. In this manner, the upper and lower edges of first implant strip 7401 and second implant strip 7402 may contact adjacent vertebrae directly.

Generally, an implant strip comprising multiple implant strips may include separating portions. In some cases, an implant strip may be configured with separating portions to limit contact between adjacent coils when the implant strip is coiled. In other cases, an implant strip may include separating portions to create space between adjacent coils to encourage bone growth into an implant strip.

In this embodiment, dual implant strip 7400 includes material 7451 that acts as a separating portion. Material 7451 may be any material that may serve as a separating portion discussed in previous embodiments. Preferably, material 7451 is applied to a portion of inner surface 7411 of first implant strip 7401 and a portion of outer surface 7422 of second implant strip 7402. In particular, material 7451 is applied to cover regions on inner surface 7411 and outer surface 7422 between upper boundary 7492 and lower boundary 7491. This arrangement creates space for the growth of bone above upper boundary 7492 and below lower boundary 7491. In addition, this configuration leaves the upper and lower edges of first implant strip 7401 and second implant strip 7402 free to contact adjacent vertebrae.

Spacer portion 7403 and material 7451 could be made of any material. In some embodiments, spacer portion 7403 and material 7451 could be made of similar materials. In other embodiments, spacer portion 7403 and material 7451 could be made of different materials. In a preferred embodiment, spacer portion 7403 and material 7451 are both made of a polymer of some kind.

Generally, material 7451 may be applied with any thickness necessary to achieve the desired width of coiled implant strip 7400. In addition, the width of spacer portion 7403 may be greater or lesser than the width of a typical implant strip. Preferably, adjusting the width of material 7451 as well as adjusting the width of spacer portion 7403 may allow the diameter of the coiled dual implant strip 7400 to be fine tuned.

Figure 75:
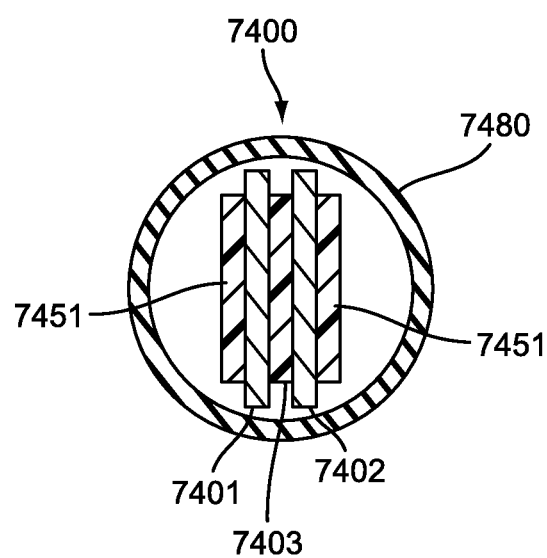
FIG. 75 is a cross sectional view of an exemplary embodiment of a cannula with an implant strip comprised of two implant strips, a spacer portion and an application of polymer.

In some embodiments, dual implant strip 7400 may be pre-formed and inserted. In other embodiments, dual implant strip 7400 may coil during implantation. In a preferred embodiment, dual implant strip 7400 may coil following insertion with a cannula. FIG. 75 illustrates a cross sectional view of an exemplary embodiment of cannula 7480 used for inserting dual implant strip 7400. Preferably, dual implant strip 7400 can be inserted between adjacent vertebrae in a manner similar to the insertion of a single implant strip. The details of this method have been previously discussed.

Figure 76:
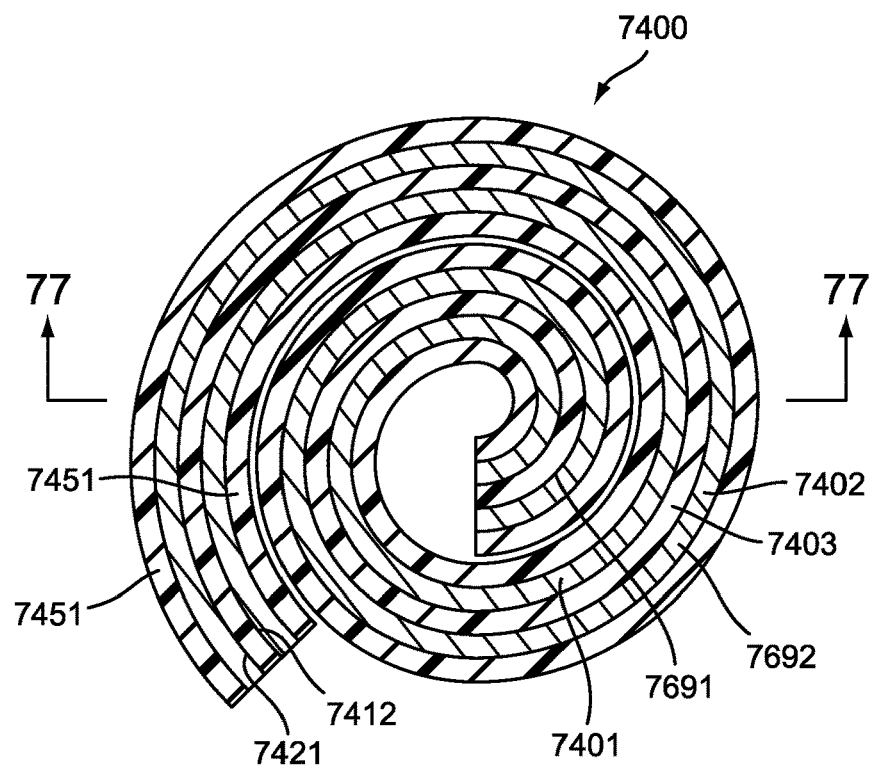
FIG. 76 is a top down view of an exemplary embodiment of a coiled implant strip comprised of two implant strips, a spacer portion and an application of polymer.

Referring to FIG. 76, dual implant strip 7400 is coiled following insertion. Due to the thickness of dual implant strip 7400, dual implant strip 7400 conforms to a coiled shape that includes first coil 7691 and second coil 7692. In other embodiments, dual implant strip 7400 may be configured with more or less coils in a coiled shape. Furthermore, first coil 7691 and second coil 7692 are spaced a distance apart by material 7451. Preferably, this spacing between first coil 7691 and second coil 7692 prevents undesirable rubbing of adjacent coils.

Figure 77:
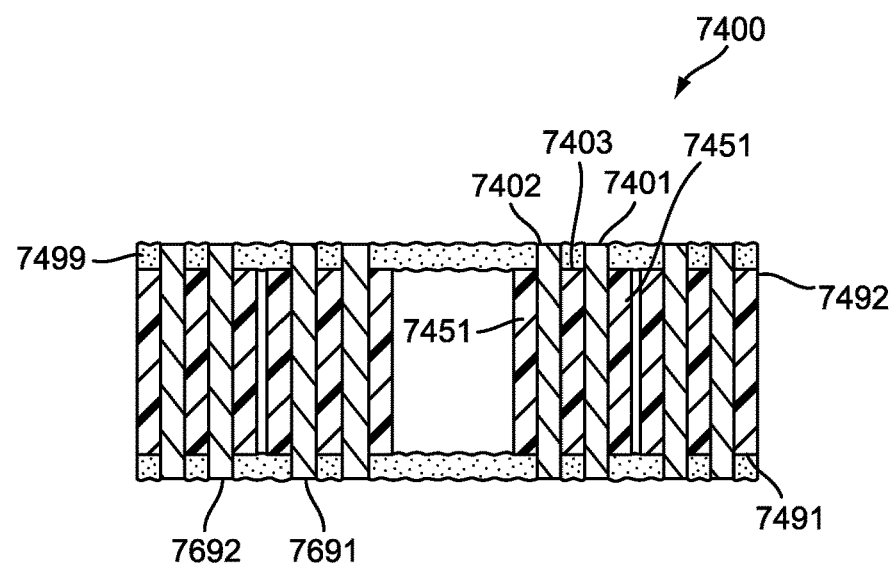
FIG. 77 is a cross sectional view of an exemplary embodiment of a coiled implant strip comprised of two implant strips, a spacer portion and an application of polymer.

FIG. 77 is a cross sectional view of the exemplary embodiment of coiled dual implant strip 7400. Preferably, the creation of space within coiled dual implant strip 7400 by spacer portion 7403 and material 7451 allows bone 7499 to grow into dual implant strip 7400. In particular, bone 7499 grows between first implant strip 7401 and second implant strip 7402 into the spaces created by spacer portion 7403. Additionally, bone 7499 grows into adjacent coils of coiled dual implant strip 7400. Specifically, bone 7499 grows into spaces created between first coil 7691 and second coil 7692 by material 7451. Furthermore, bone 7499 is blocked from growing between upper boundary 7492 and lower boundary 7491 of dual implant strip 7400 by spacer portion 7403 and material 7451. With this arrangement, the upper and lower edges of first implant strip 7401 and second implant strip 7402 are free to contact adjacent vertebrae. This configuration allows dual implant strip 7400 to be anchored into place between adjacent vertebrae.

As previously discussed, an implant strip may be configured with distinct portions that are made of different materials. Different materials may have different material properties, including deflection and/or deformation properties. By constructing distinct portions of an implant strip with different materials, the deflection and/or deformation properties of an implant strip may be fine tuned.

Figure 69:
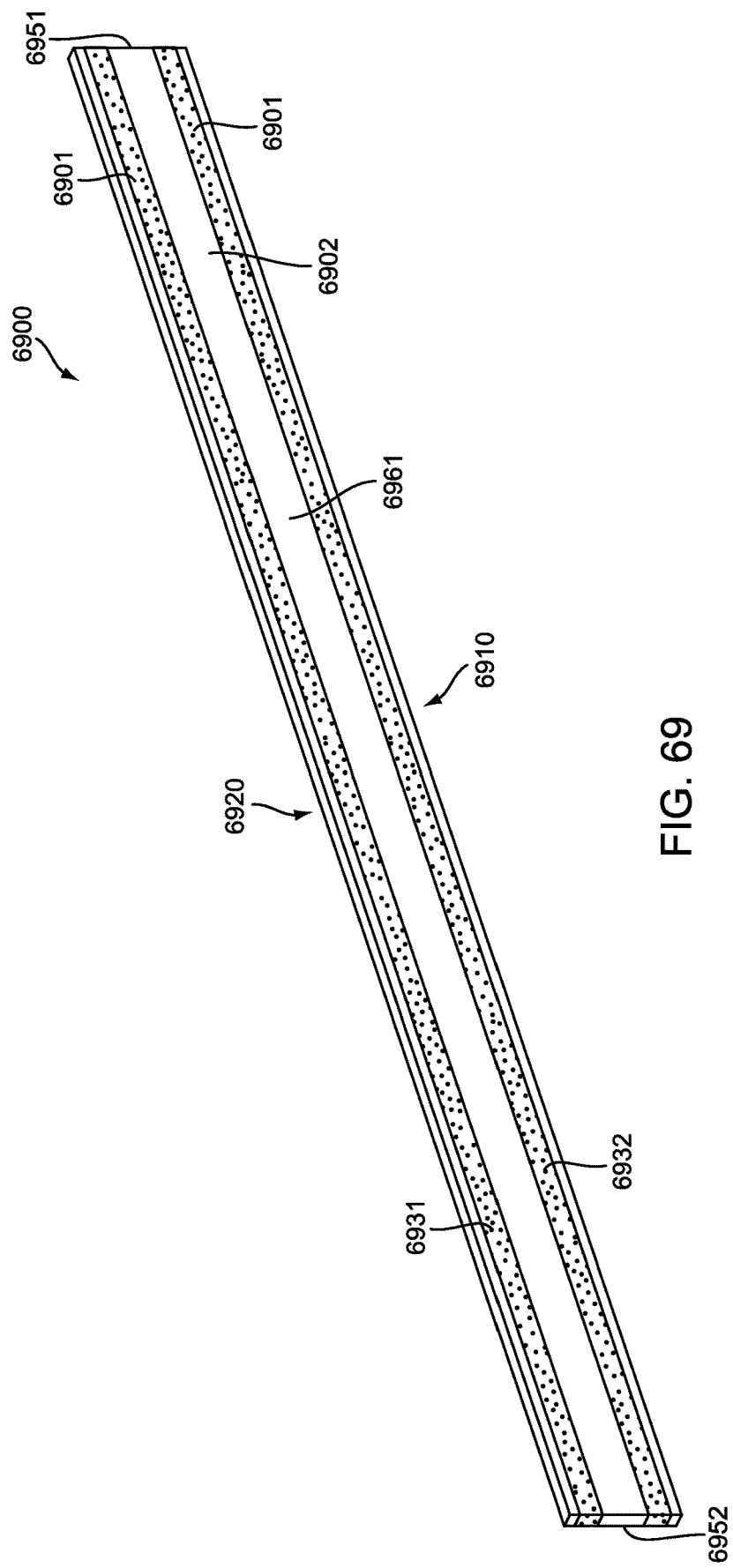
FIG. 69 is an isometric view of an exemplary embodiment of an implant strip constructed with multiple materials.

FIG. 69 illustrates an exemplary embodiment of implant strip 6900. In this embodiment, implant strip 6900 is comprised of first portion 6901 and second portion 6902. First portion 6901 is constructed of a first material. Similarly, second portion 6902 is constructed of a second material. In this case, the first material and second material are different materials. Furthermore, the first material and second material have different deflection and/or deformation properties. Generally, the first material and second material may be any type of discussed in this detailed description. In this exemplary embodiment, the first material is a more elastic material and the second material is a more rigid material.

Generally, distinct portions may be disposed in various configurations to create an implant strip. In this exemplary embodiment, first portion 6901, constructed of the more elastic first material, includes first region 6931 and second region 6932. First region 6931 and second region 6932 extend in a longitudinal direction between first end 6951 and second end 6952 of implant strip 6900. In particular, first region 6931 is disposed near upper edge 6920. In a similar manner, second region 6932 is disposed near lower edge 6910.

Second portion 6902 includes central region 6961 as well as upper edge 6920 and lower edge 6910. This provides implant strip 6900 with rigid central region 6961 as well as rigid upper edge 6920 and rigid lower edge 6910. Additionally, flexible first region 6931 and flexible second region 6932 are interspersed between central region 6961, upper edge 6920 and lower edge 6910. In this manner, implant strip 6900 may deform near upper edge 6920 and lower edge 6910 although upper edge 6920 and lower edge 6910 maintain a rigid shape. In some cases, this configuration may increase the strength of implant strip 6900 in the axial direction. Furthermore, this arrangement may assist implant strip 6900 in enduring bending, lateral, and twisting forces.

By selecting materials with particular deflection and/or deformation properties and incorporating those materials into distinct portions of an implant strip, the deflection and/or deformation characteristics of an implant strip may be fine tuned. For example, in an alternative embodiment of implant strip 6900, the second material may be more flexible than the first material. In other words, upper edge 6920 and lower edge 6910 as well as central region 6961 may be constructed of a flexible material while first region 6931 and second region 6932 are constructed of a more rigid material. In some cases, the flexible material may allow upper edge 6920 and lower edge 6910 to deform with contact from adjacent vertebrae. However, the rigid material of first region 6931 and second region 6932 may limit the deflection and/or deformation. Also, central region 6961 may defect and/or deform to endure bending, lateral, axial, and twisting forces. Preferably, the deflection and/or deformation properties of an implant strip may be tuned by altering the materials as well as the sizes and shapes of distinct portions of an implant strip.

Distinct portions of an implant strip may be attached in various manners to create the implant strip. In embodiments where distinct portions comprising materials of differing flexibility are used, these embodiments can include provisions for facilitating attachment between the distinct portions. Preferably, these embodiments can include provisions to help prevent the distinct portions from detaching over time and with use.

Figure 70:
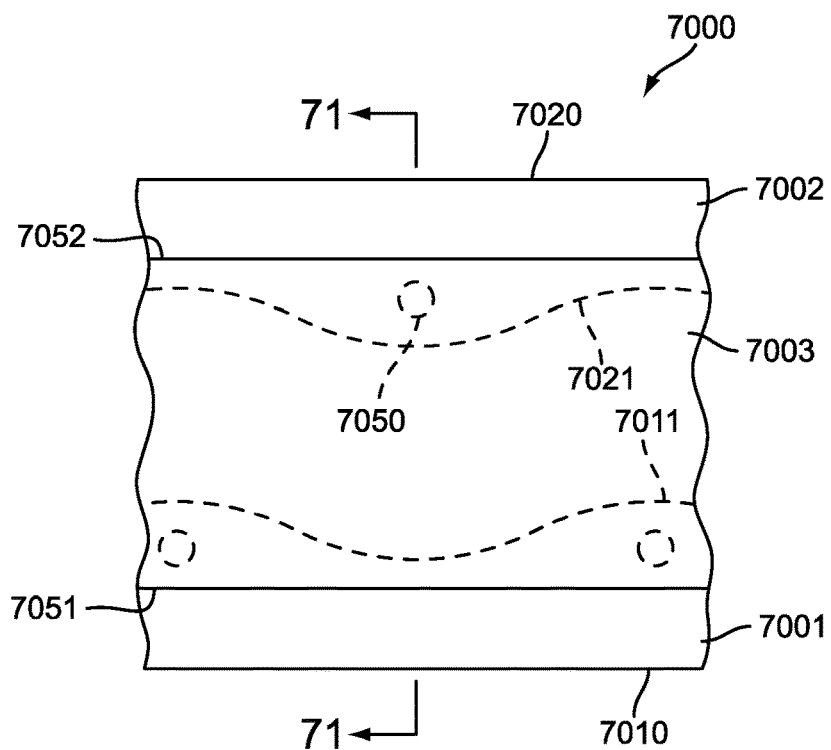
FIG. 70 is a schematic view of an exemplary embodiment of an implant strip configured with distinct portions.
Figure 71:
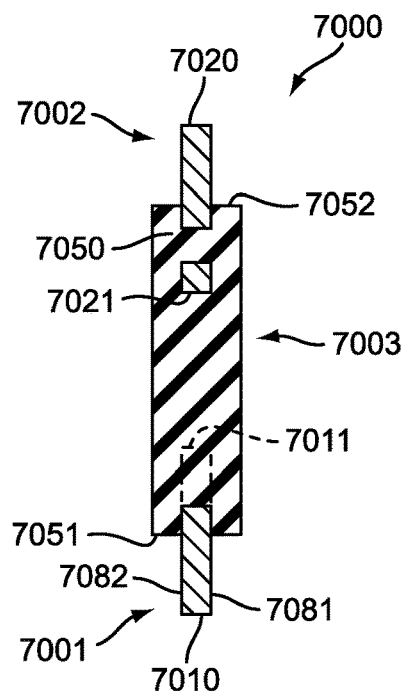
FIG. 71 is a cross sectional view of an exemplary embodiment of an implant strip configured with distinct portions.

FIGS. 70-71 illustrate an exemplary embodiment of a portion of implant strip 7000. In this embodiment, implant strip 7000 includes three distinct portions. In particular, implant strip 7000 includes upper portion 7002, lower portion 7001 and central portion 7003. Upper portion 7002 preferably includes upper edge 7020 of implant strip 7000. In addition, upper portion 7002 includes first bottom edge 7021. In a similar manner, lower portion 7001 preferably includes lower edge 7010 and first top edge 7011. Furthermore, central portion 7003 extends from second top edge 7052 to second bottom edge 7051. In a preferred embodiment, central portion 7003 may overlap with first bottom edge 7021 of upper portion 7002 and first top edge 7011 of lower portion 7001.

In different embodiments, the shape of first top edge 7011 and first bottom edge 7021 may vary. In some embodiments, first bottom edge 7021 and first top edge 7011 may have a wave like shape. In other embodiments, first bottom edge 7021 and first top edge 7011 could be generally straight. In this preferred embodiment, first bottom edge 7021 and first top edge 7011 have a wave like shape that varies in a periodic manner. This arrangement may provide periodically spaced portions that can facilitate attachment of upper portion 7002, lower portion 2001 and central portion 7003.

Generally, upper portion 7002, central portion 7003, and lower portion 7001 may be constructed from any material discussed in this detailed discussion. In this exemplary embodiment, upper portion 7002 and lower portion 7001 are constructed of a relatively rigid material. Additionally, central portion 7003 is configured of a relatively more elastic material. This configuration preferably allows implant strip 7000 to deform and endure axial loads from adjacent vertebrae.

Preferably, upper portion 7002 and lower portion 7001 include provisions to attach to central portion 7003. In this exemplary embodiment, upper portion 7002 and lower portion 7001 include gaps 7050. Gaps 7050 are disposed at intervals proximate to both first bottom edge 7021 and first top edge 7011. In particular, gaps 7050 may be associated with crests of first bottom edge 7021 and first top edge 7011. Although only a portion of implant strip 7000 is illustrated in FIG. 70, it may be assumed that gaps 7050 extend at intervals in a longitudinal direction between a first end and a second end of implant strip 7000.

Referring to FIG. 71, gaps 7050 extend from inner surface 7081 of upper portion 7002 and lower portion 7001 to outer surface 7082 of upper portion 7002 and lower portion 7001. Preferably, central portion 7003 may be configured to extend through gaps 7050 within upper portion 7002 and lower portion 7001. With this arrangement, portions of upper portion 7002 and lower portion 7001 may be embedded within central portion 7003. This configuration can assist in securely attaching central portion 7003 to upper portion 7002 and lower portion 7001.

Central portion 7003 also preferably extends between first bottom edge 7021 and first top edge 7011. As seen in FIG. 71, in a preferred embodiment, central portion 7003 may comprise a generally monolithic elastic material. This generally monolithic arrangement may provide increased structural stability for implant strip 7000. In other embodiments, however, central portion 7003 could include any number of holes, gaps, voids, and/or channels. In some cases, holes, gaps, voids and/or channels can be used to modify the overall elastic properties of central portion 7003.

The preferred arrangement illustrated in FIGS. 70 and 71 may help to prevent separation between portions comprising distinct materials. In particular, upper portion 7002 is prevented from separating from central portion 7003 since central portion 7003 is disposed through gaps 7050 in upper portion 7002. Likewise, lower portion 7001 is prevented from separating from central portion 7003 since central portion 7003 is disposed through gaps 7050 in lower portion 7001. By substantially reducing the likelihood that distinct portions of implant strip 7000 may separate, the lifetime of implant strip 7000 can be substantially increased.

Generally, an implant strip may be configured to coil into any particular shape. In some embodiments, a coiled shape of an implant strip may be tailored to the replacement of an intervertebral disc or vertebral body of a patient. In some cases, an implant strip may be configured to coil into a particular shape to partially or fully fill a cavity of an intervertebral disc and provide increased support to the adjacent vertebrae. In other cases, an implant strip may conform to a particular coiled shape to replace a vertebral body. In other embodiments, a coiled implant strip may be configured to a particular shape to increase the effectiveness of a disc fusion procedure. In still other embodiments, an implant strip may be designed with a particular coiled shape to accommodate the insertion of multiple implant strips.

FIGS. 50-53 illustrate exemplary embodiments of implant strips configured to coil into a particular shape. These embodiments are not meant to be limiting, in other embodiments, implant strips may be configured to coil into additional coiled shapes. Preferably, the implant strips in these embodiments may be inserted in an identical manner to the methods used to insert the previously discussed implant strips. In particular, the implant strips in these embodiments may be pre-formed and inserted (see FIGS. 51 and 53) or may coil during insertion (see FIGS. 50 and 52). Additionally, delivery devices may assist in the insertion and configuration of the implant strips into particular coiled shapes. Furthermore, the implant strips in these embodiments may include all the features discussed in the previous and following embodiments.

Generally, the implant strips in these embodiments may be made of any material, including shape memory alloys and spring steel, as well as other types of materials, including materials discussed in other embodiments. An implant strip may be constructed from any suitable material that may be configured to assume a desired shape when formed in a coil.

In some embodiments, the shape of a coiled implant strip may be modified. In previous embodiments, the implant strips retain a generally cylindrical shape. In other embodiments, however, it may be desirable to modify the shape of the implant strip to adjust various loading properties of the coil. For example, using a kidney shaped coil may allow the surgeon to modify the axial loading properties along various portions between two adjacent vertebrae.

Figure 50:
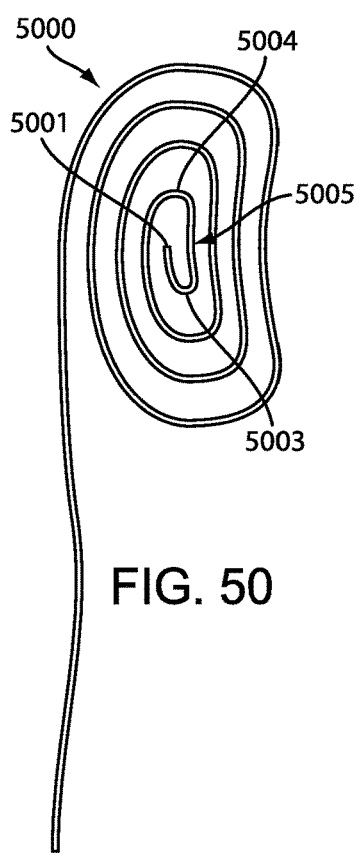
FIG. 50 is a schematic view of an exemplary embodiment of an implant strip coiling in a kidney shape.

Referring to FIG. 50, implant strip 5000 may be configured to coil into a kidney shape. In this schematic illustration of the coiling of implant strip 5000, distal end 5001 of implant strip 5000 preferably forms first curved portion 5003 and second curved portion 5004 to create a kidney shaped first inner coil 5005. By following first inner coil 5005, the remainder of implant strip 5000 may be configured to coil into a kidney shape.

Figure 51:
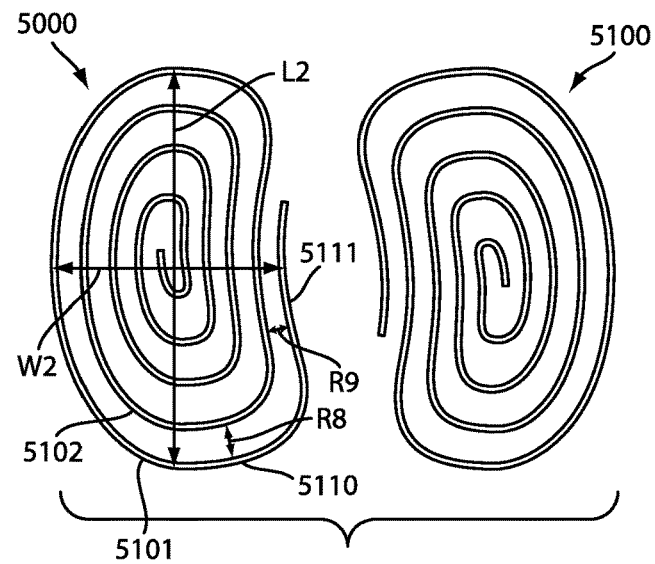
FIG. 51 is a schematic view of an exemplary embodiment of two coiled kidney shaped implant strips.

When coiled in the kidney shape, implant strip 5000 has width W2 and length L2, as seen in FIG. 51. In this embodiment, length L2 is significantly greater than width W2. Generally, length L2 and width W2 may have any value and vary from one embodiment to another.

Furthermore, the kidney shape of coiled implant strip 5000 produces different radial distances between different portions of adjacent coils. In some cases, adjacent coils may be separated by greater distances on portions of coils disposed along the longitudinal axis of implant strip 5000 and separated by shorter distances on portions of the coils disposed along the latitudinal axis. For example, first outer coil 5101 and second outer coil 5102 may be separated by radial distance R8 at first portion 5110, disposed along the longitudinal axis of implant strip 5000. At second portion 5111, disposed along the latitudinal axis of implant strip 5000, first outer coil 5101 and second outer coil 5102 are separated by radial distance R9 that is less than radial distance R8. In general, the coiled shape of an implant strip may produce various spacing between portions of adjacent vertebrae. With this preferred arrangement, the in-growth of bone may be encouraged at particular portions of implant strip 5000.

As previously discussed, multiple implant strips may be implanted simultaneously between adjacent vertebrae. In some cases, by modifying the shapes of one or more implant strips, a surgeon may implant multiple implant strips between adjacent vertebrae in different arrangements.

Implant strip 5000 may be implanted with second implant strip 5100, as seen in FIG. 51. In this embodiment, second implant strip 5100 is identical in size and shape to implant strip 5000. However, second implant strip 5100 is oriented as a mirror image of implant strip 5000. In other embodiments, any number of implant strips configured with various coiled shapes and oriented in a variety of directions may be implanted with implant strip 5000. In some cases, each implant strip may be associated with a different height to create Lordosis or correct scoliosis. Preferably, multiple implant strips may be inserted to fill a disc region and provide support to adjacent vertebrae.

Figure 52:
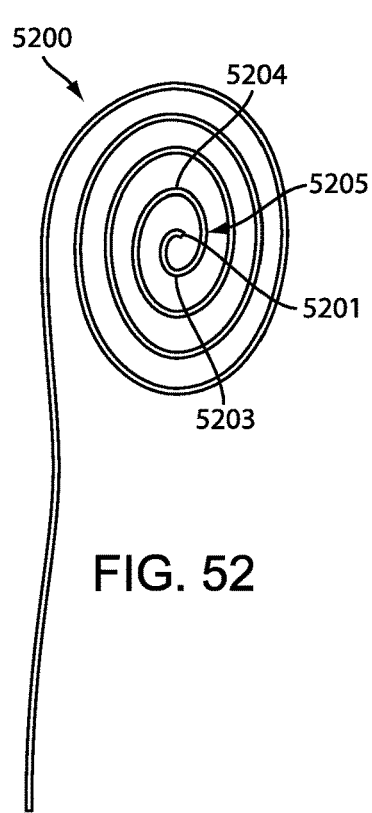
FIG. 52 is a schematic view of an exemplary embodiment of an implant strip coiling in an oval shape.
Figure 53:
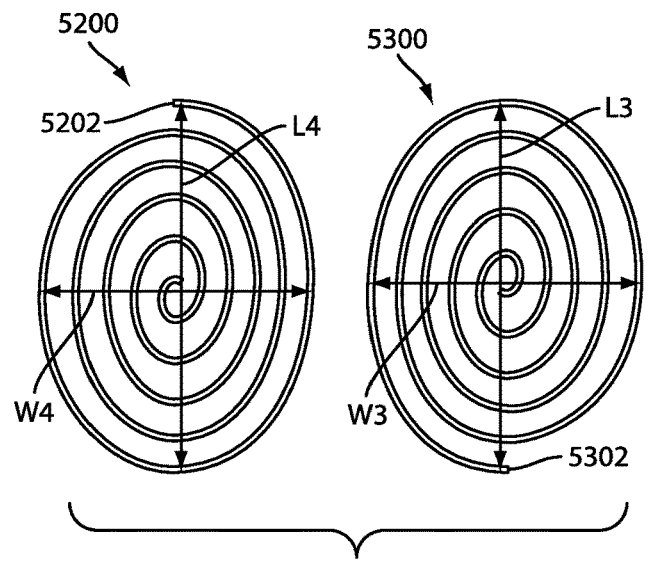
FIG. 53 is a schematic view of an exemplary embodiment of two coiled oval shaped implant strips.

FIGS. 52-53 illustrate a schematic view of an exemplary embodiment of implant strip 5200. In this embodiment, implant strip 5200 is configured to coil in an oval shape. In particular, first distal end 5201 introduces first curved portion 5203 and second curved portion 5204 to create first inner coil 5205. Preferably, by following first inner coil 5205, the remainder of implant strip 5200 may be configured to coil into an oval shape.

FIG. 53 illustrates a schematic view of an exemplary embodiment of coiled implant strip 5200 implanted with second implant strip 5300. Preferably, implant strips 5200 and 5300 are coiled in identical oval shapes. In particular, implant strip 5200 has length L4 and width W4 that is less then length L4. In a similar manner, second implant strip 5300 has length L3 and width W3. Lengths L3 and L4, as well as widths W3 and W4, are substantially identical in this embodiment. Generally, lengths L3 and L4, as well as widths W3 and W4, may have any value and vary from one embodiment to another. In this embodiment, the oval shape of implant strips 5200 and 5300 produces approximately similar radial distances between adjacent coils.

Additionally, in this embodiment, implant strips 5200 and 5300 are inserted in opposite orientations. Specifically, implant strips 5200 and 5300 are inserted so that second end 5202 of implant strip 5200 and second end 5302 of second implant strip 5300 are disposed opposite of each other. Preferably, the insertion of implant strips 5200 and 5300 provides spinal continuity.

Typically, vertebrae are not completely symmetric and so the spacing between adjacent vertebrae may vary. A coiled implant strip that presents a particular shape at the top and/or bottom surface of the implant strip may allow for a more natural fit of the implant strip between adjacent vertebrae. In particular, an implant strip that presents different portions with differing axial heights can provide for a better fit between a coiled implant strip and adjacent vertebrae. With this arrangement, an implant strip may fit the natural contours of the adjacent vertebrae and perform a similar function to a spinal disc.

In some embodiments, a coiled implant strip may provide a particular contour on a top surface, while presenting a flat profile on a bottom surface. In other embodiments, a coiled implant strip may provide a particular contour on a bottom surface, although a top surface of the coiled implant strip is generally flat. In still other embodiments, a coiled implant strip may provide a first contour on a top surface and a second contour, different from the first contour, on a bottom surface. In a preferred embodiment, an implant strip may include symmetrical surfaces on a top and bottom surface when coiled.

Preferably, in these embodiments, contours of a top and/or bottom surface of a coiled implant strip may be formed by shaping a top and/or bottom edge of an implant strip. The shape of a top and bottom edge of an implant strip may be created by cutting or removing portions of an implant strip. Cutting may be done using techniques known in the art, including, but not limited to, punching, laser fusion and/or water drilling, stamping, or any combination of techniques. In other embodiments, a shape on an edge may be formed using a die of some kind.

FIGS. 54-62 illustrate schematic views of exemplary embodiments of implant strips that present particular contours on the top and bottom surfaces of the implant strips when coiled. For the purpose of clarity, the implant strips in these embodiments are illustrated schematically and are typically much longer. Preferably, the implant strips in these embodiments may be inserted in an identical manner to the methods used to insert the previously discussed implant strips. In some cases, the implant strips in these embodiments may be pre-formed prior to insertion. In other cases, the implant strips in these embodiments may coil during insertion. Also, the implant strips in these embodiments may include any other features discussed in other embodiments in this detailed description.

Figure 54:
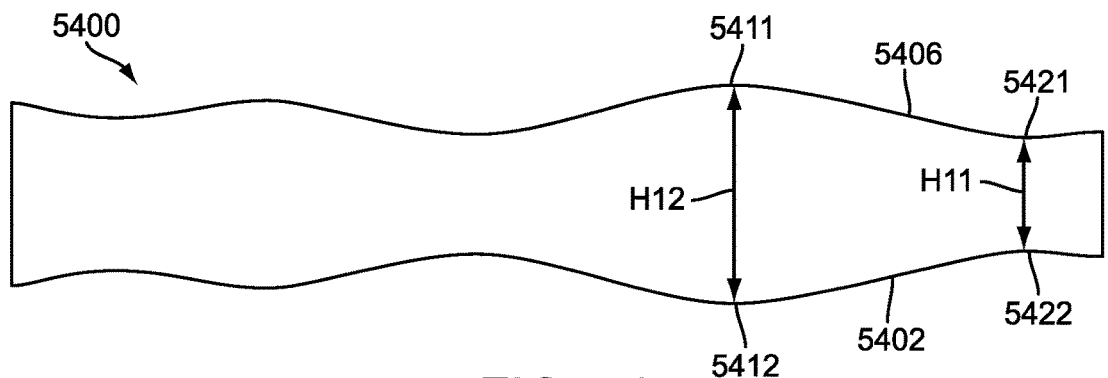
FIG. 54 is a plan view of an exemplary embodiment of an implant strip with a curvilinear shape on an upper and lower edge.
Figure 55:
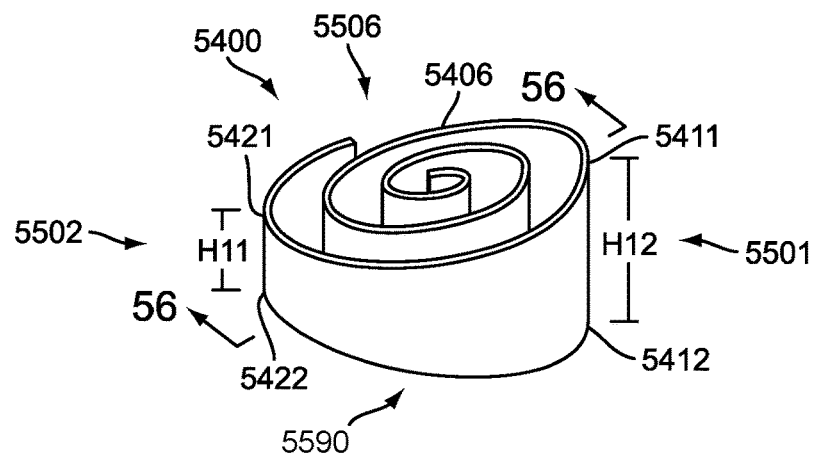
FIG. 55 is an isometric view of an exemplary embodiment of a coiled implant strip configured with a wedge shape.
Figure 56:
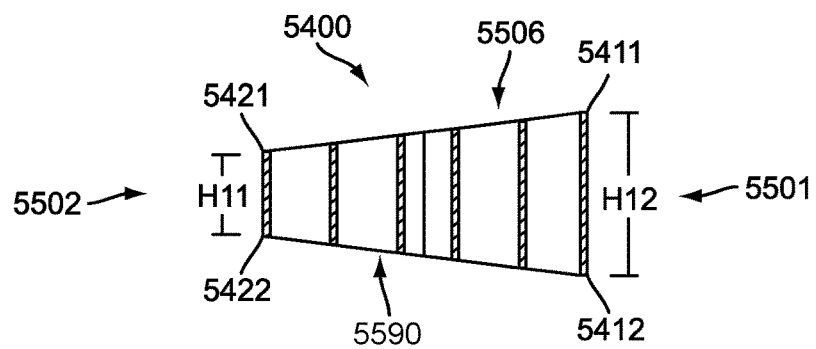
FIG. 56 is a cross sectional view of an exemplary embodiment of a coiled implant strip configured with a wedge shape.

FIGS. 54-56 illustrate an exemplary embodiment of implant strip 5400. Implant strip 5400 includes upper edge 5406 and lower edge 5402. In this embodiment, upper edge 5406 and lower edge 5402 are configured with a symmetrical curvilinear shape, including interspersed crests and troughs. Specifically, the shape on edges 5406 and 5402 is configured to provide implant strip 5400 with maximum height H12 at first crest 5411 disposed on upper edge 5406 and corresponding second crest 5412 disposed on lower edge 5402. In addition, implant strip 5400 is configured with minimum height H11 at first trough 5421 disposed on upper edge 5406 and corresponding second trough 5422 disposed on lower edge 5402. Furthermore, the crests and troughs on edges 5406 and 5402 confer intervening heights between maximum height H12 and minimum height H11 on implant strip 5400. In particular, successive crests on edges 5406 and 5402 are separated by a distance approximately equal to one 360 degree turn of a coil when implant strip 5400 is in a coiled state. In a similar manner, successive troughs on edges 5406 and 5402 are separated by a distance approximately equal to one 360 degree turn of a coil when implant strip 5400 is in a coiled state.

When implant strip 5400 is coiled, the curvilinear shape on edges 5406 and 5402 preferably creates a wedge shape, as seen in FIG. 55. In particular, coiled implant strip 5400 has maximum height H12 at first portion 5501 and minimum height H11 at second portion 5502. With this preferred arrangement, upper edge 5406 creates an inclined plane on top surface 5506. In a similar manner, lower edge 5402 provides an inclined plane on bottom surface 5590. FIG. 56 is a cross sectional view of the exemplary embodiment of implant strip 5400 in a coiled state.

In some cases, a wedge shaped implant strip may be used to correct scoliosis or spondylolisthesis. In other cases, a wedge shaped implant strip may assist in providing lordosis to a vertebral column. In particular, in some embodiments, a coiled implant strip with a wedge shape may be inserted to orient a portion of the coiled implant strip with a maximum height to the anterior and a portion of the coiled implant strip with a minimum height to the posterior of a patient. In other embodiments, the orientation of an implanted wedge shaped coiled implant strip may be tailored to a specific patient. For example, a wedge shaped coiled implant strip may be oriented to correct scoliosis in a patient.

Figure 57:
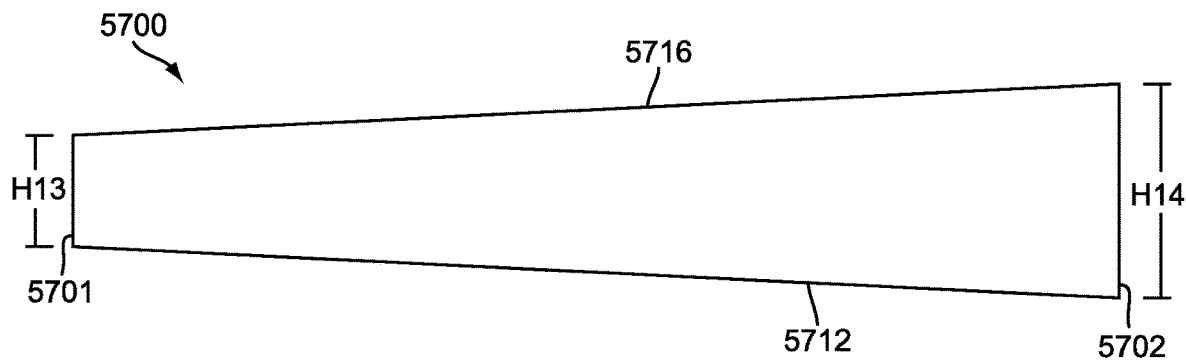
FIG. 57 is a plan view of an exemplary embodiment of a tapered implant strip.
Figure 58:
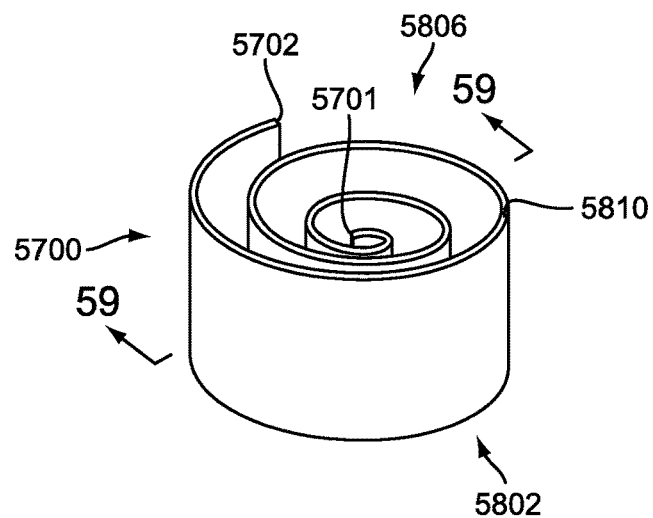
FIG. 58 is an isometric view of an exemplary embodiment of a coiled implant strip configured with a concave shape on a top and bottom surface.
Figure 59:
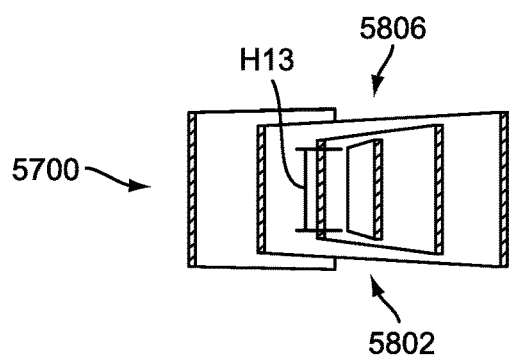
FIG. 59 is a cross sectional view of an exemplary embodiment of coiled implant strip configured with a concave shape on a top and bottom surface.

In some embodiments, an implant strip may be tapered to create a concave shape on a top and/or bottom surface when the implant strip is coiled. FIGS. 57-59 illustrate an exemplary embodiment of implant strip 5700 tapered from second end 5702 to first end 5701. In particular, second end 5702 extends maximum height H14 and first end 5701 extends minimum height H13. Generally, maximum height H14 and minimum height H13 may have any values and may vary from one embodiment to another. In addition, in the current embodiment upper edge 5716 and lower edge 5712 smoothly decline from second end 5702 to first end 5701. In other embodiments, edges 5716 and 5712 may decline in another manner.

Referring to FIG. 58, implant strip 5700 is coiled with first end 5701 disposed on an inner coil. Second end 5702 is disposed on outer coil 5810. With this arrangement, coiled implant strip 5700 presents a generally concave shape on top surface 5806. Likewise, a generally concave shape is disposed on bottom surface 5802. FIG. 59 provides a cross sectional view of the exemplary embodiment of implant strip 5700. Minimum height H13 may be clearly seen at the center of coiled implant strip 5700 in this Figure. Using this configuration, adjacent vertebrae may be supported and in-growth of bone into implant strip 5700 may assist in anchoring implant strip 5700 in position.

Figure 60:
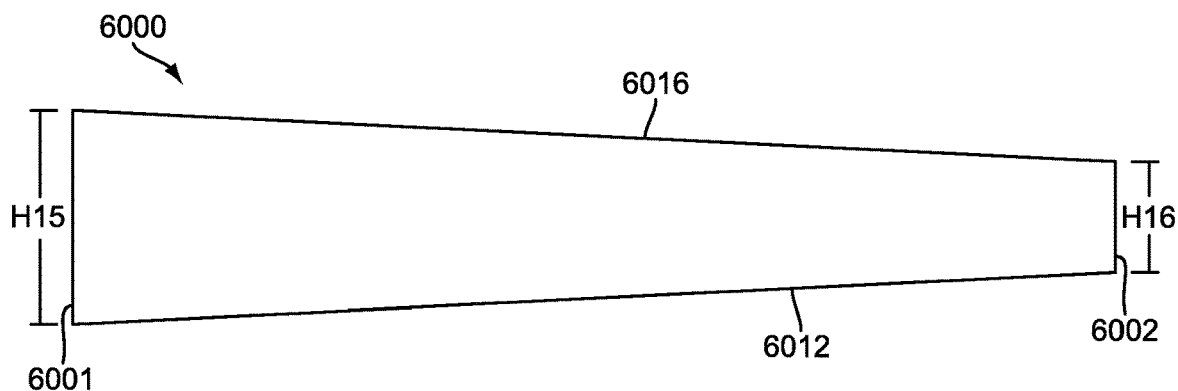
FIG. 60 is a plan view of an exemplary embodiment of a tapered implant strip.
Figure 61:
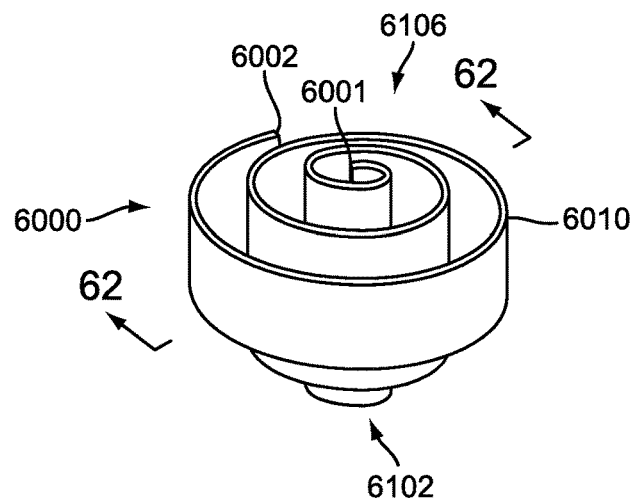
FIG. 61 is an isometric view of an exemplary embodiment of a coiled implant strip configured with a convex shape on a top and bottom surface.
Figure 62:
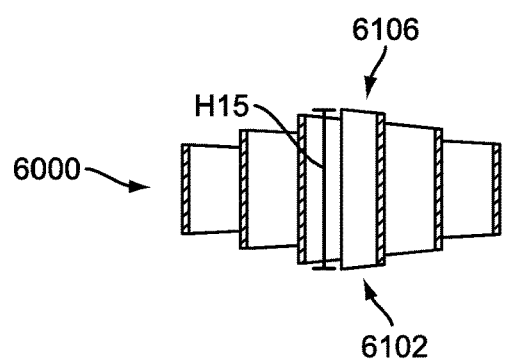
FIG. 62 is a cross sectional view of an exemplary embodiment of coiled implant strip configured with a convex shape on a top and bottom surface.

In other embodiments, an implant strip may be configured to create a convex shape on a top and/or bottom surface of the coiled implant strip. FIGS. 60-62 illustrate an exemplary embodiment of implant strip 6000, including first end 6001 and second end 6002. In this embodiment, implant strip 6000 is tapered with upper edge 6016 and lower edge 6012 smoothly declining from first end 6001 to second end 6002. In particular, first end 6001 is configured with maximum height H15. In a similar manner, second end 6002 is configured with minimum height H16. Generally, maximum height H15 and minimum height H16 may have any values and may vary from one embodiment to another.

With this arrangement, implant strip 6000 is coiled with first end 6001 disposed at the center of the coiling, as seen in FIG. 61. Also, second end 6002 is disposed on outer coil 6010. Preferably, upper edge 6016 of coiled implant strip 5700 creates a generally convex shape on top surface 6106. Likewise, lower edge 6012 creates a generally convex shaped on bottom surface 6102. A cross sectional view of the exemplary embodiment of implant strip 6000 is illustrated in FIG. 62. The convex shape on top surface 6106 and bottom surface 6102 with maximum height H15 disposed at the center of the coiling of implant strip 6000 may be clearly seen in this Figure. This preferred arrangement may provide spinal continuity and encourage bone growth, in particular, on a periphery of coiled implant strip 6000.

Preferably, the different provisions of implant strips discussed in this detailed description may be combined to create a spinal implant strip that maximizes the utility of the implant strip for a particular patient. Furthermore, a bone growth promoting agent may be applied to a portion or an entirety of an implant strip in concert with any other provisions described in this detailed description. Generally, a surgeon or medical expert may assess a patient and configure a spinal implant device based on factors specific to the patient. In some cases, for example, a surgeon or medical expert may consider the location of the damaged tissue, size of the vertebrae, and anatomical shape of the vertebrae or spinal disc as factors in the design choice of an implant strip. In other cases, a particular combination of provisions of an implant strip may be chosen to correct scoliosis or spondylolisthesis. In still other cases, an implant strip may be configured to alleviate compression of the nerves in the spinal foramen and canal. Generally, an implant strip may be configured with particular provisions to approximate the natural biomechanics of the spine and provide for spinal continuity.

Figure 63:
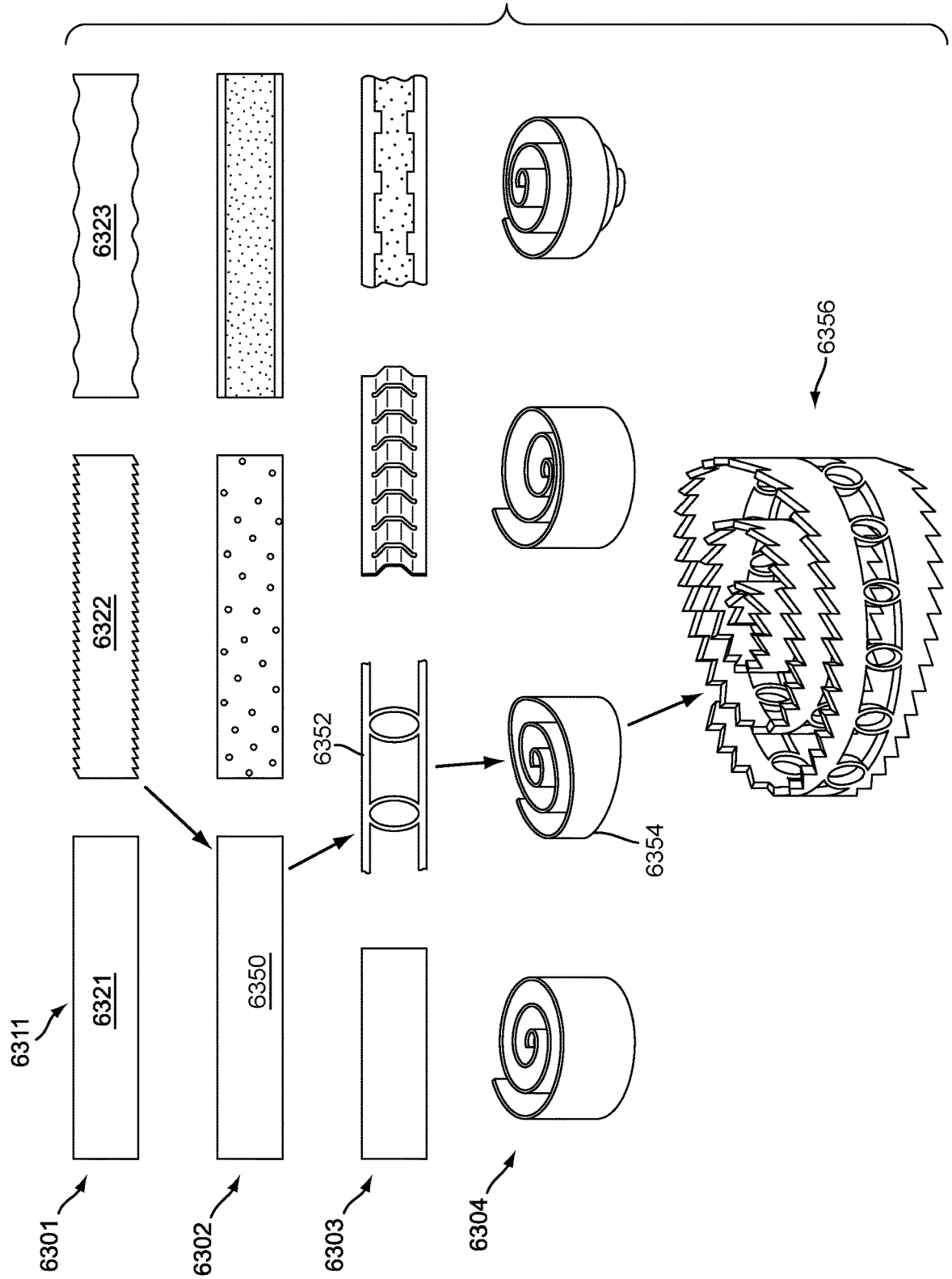
FIG. 63 is a schematic view of an exemplary embodiment of a possible configuration of an implant strip using a plurality of provision sets.
Figure 64:
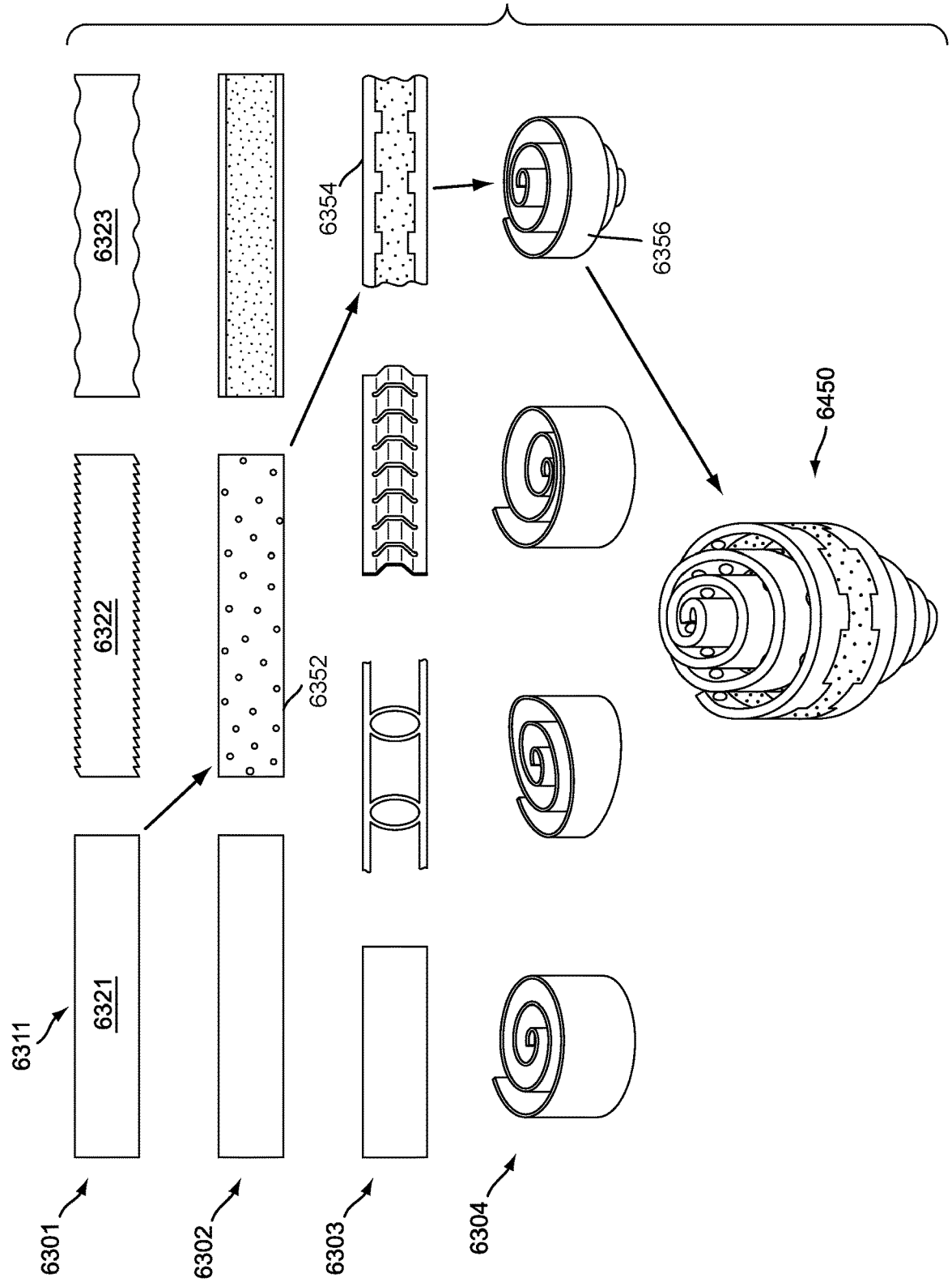
FIG. 64 is a schematic view of an exemplary embodiment of a possible configuration of an implant strip using a plurality of provision sets.
Figure 65:
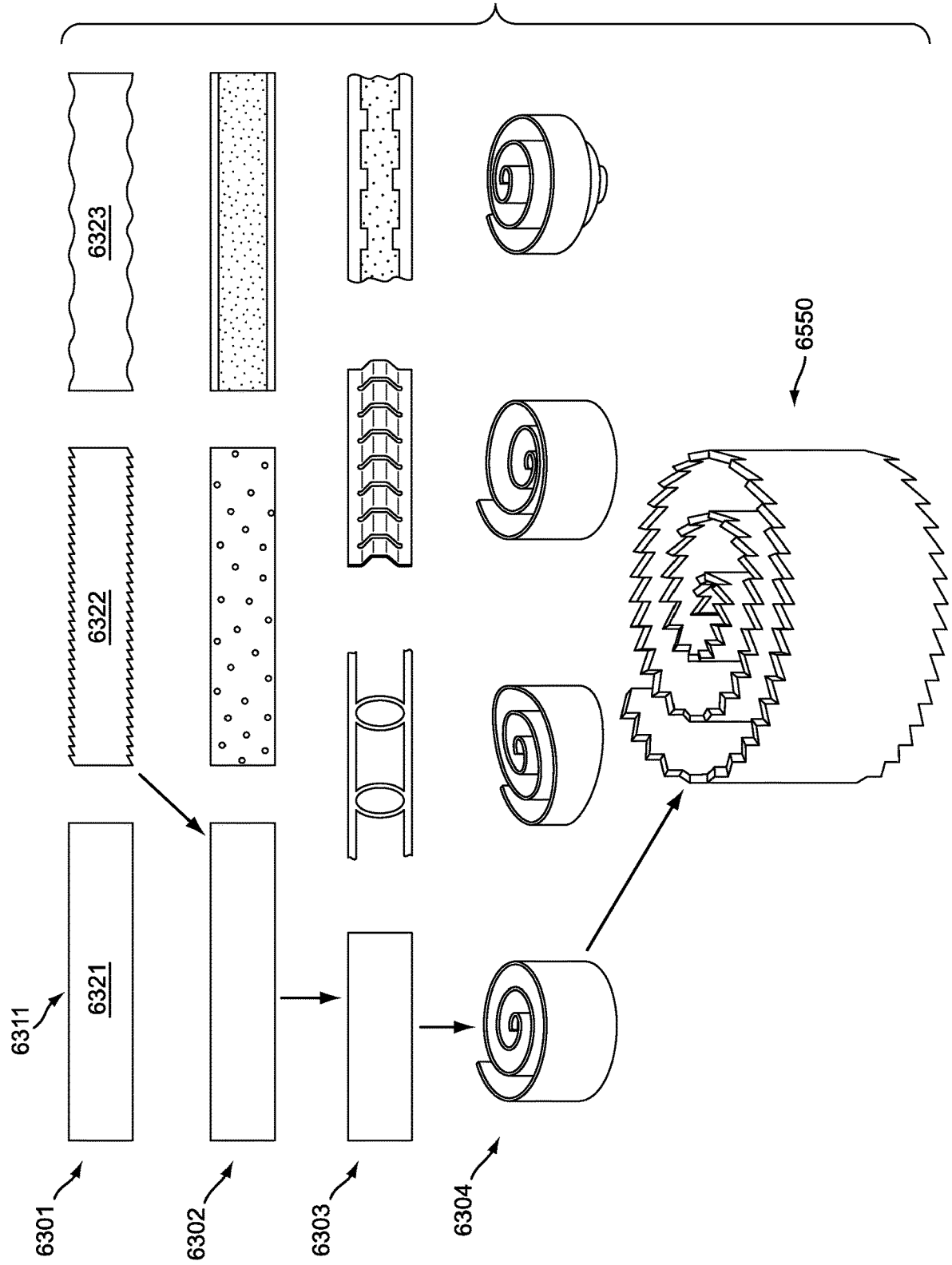
FIG. 65 is a schematic view of an exemplary embodiment of a possible configuration of an implant strip using a plurality of provision sets.

FIGS. 63-65 illustrate a schematic representation of an embodiment of various provisions associated with implant strips and exemplary combinations of those various provisions to create implant strips. In this embodiment, these provisions are arranged into various provision sets, grouped with common properties. In other embodiments, these provisions may be arranged differently. In this embodiment, a first row includes teeth set 6301 with a choice of teeth disposed on an upper and lower edge of an implant strip. Additionally, a second row contains spacing set 6302 with a choice of spacing features that may be disposed on an implant strip. In a similar manner, a third row contains deflection set 6303 with provisions for the deflection of an implant strip. Also, a fourth row includes shape set 6304 that includes various shapes configured on the top and bottom surfaces of implant strips.

Furthermore, the first choice in each set 6301-6304, notably first column 6311, provides the option for not selecting the feature associated set. For example, first implant strip 6321 of teeth set 6301 has no teeth on an upper or lower edge. However, second implant strip 6322 of teeth set 6301 includes teeth disposed in a saw tooth pattern on an upper edge and lower edge. Teeth set 6301 further includes third implant strip 6323 with irregularly spaced rounded teeth disposed on an upper and lower edge. In some embodiments, additional elements with other provisions may be added to sets 6301-6304. In some cases, for example, an implant strip with regularly spaced rounded teeth disposed on an upper edge may be added to teeth set 6301. Also, in other embodiments, additional sets with other provisions may be considered when selecting features for an implant strip tailored for a particular patient.

FIG. 63 illustrates a schematic view of an exemplary embodiment of a selection of provisions for implant strip 6350. In this embodiment, a saw tooth pattern for teeth is selected from second implant strip 6322 of teeth set 6301. Additionally, first option 6350 with no spacing is chosen from spacing set 6302. Also, second option 6352 of an implant strip with provisions for axial deflection is selected from deflection set 6303. Finally, wedge shape 6354 is chosen from shape set 6304. With this combination of features, implant strip 6356 is created and preferably tailored to different properties of a deformation of a spine of a particular patient.

FIG. 64 illustrates a schematic view of the selection of features for a second exemplary embodiment of spinal implant strip 6450. In this embodiment, first option 6321 with no teeth disposed on an upper and lower edge from teeth set 6301 is selected. Next, protrusion option 6452 is chosen as spacers from spacing set 6302. In a third choice, an elastomer strip option 6354 is selected from deflection set 6303. In a fourth choice, convex shape option 5356 with a convex top and bottom surface is chosen from shape set 6304. With this combination of selections, implant strip 6450 may be constructed and preferably be tailored to conditions in a spine of a specific patient.

FIG. 65 illustrates a schematic view of the combination of features for a third exemplary embodiment of spinal implant strip 6550. In this embodiment, saw tooth option 6322 for teeth is selected from teeth set 6301. In a second choice, no spacing provisions are selected from spacing set 6302. Additionally, no deflection provisions are selected from deflection set 6303. Finally, no modified shape provisions are chosen from shape set 6304. This combination of provisions yields implant strip 6550. With this preferred arrangement, implant strip 6550 includes features to embed into adjacent vertebrae following insertion.

In addition to the combinations of implant strips that have already been described, it is also possible to form other combinations. If there are three distinct elements in a teeth set, three distinct elements in a spacing set, four distinct elements in a deflection set, and four distinct elements in a shape set, then there are one hundred and forty-four distinct implant strips that can be formed. As the number of distinct feature sets and the number of elements within feature sets increases, the total number of possible implant strips grows. A larger number of distinctly configured implant strips allows a medical expert or surgeon to make more subtle adjustments to an implant disc to increase the ability of an implant strip to mimic the dynamic properties of a disc and/or provide for the continuity of a spine.

As discussed previously, an implant strip may include provisions to change shape. In some embodiments, an implant strip with provisions to change shape may be constructed of a shape-memory material. An implant strip constructed of a shape-memory material may be configured in a first shape prior to implantation. After implantation, the implant strip may assume a second shape that is different from the first shape.

In some cases, a signal associated with implantation may trigger the implant strip to transform to the second shape. Generally, the signal associated with implantation may be any type of signal including, but not limited to, heat, light, a local chemical environment, or mechanical or electrical stimulation. For example, when an implant strip is implanted, the body temperature of a patient may trigger the implant strip to transform into a second shape.

Generally, an implant strip constructed of shape-memory material may form various types of second shapes following implantation. In some cases, the second shape may be an oval shape. In other cases, the second shape may be any desired shape, including a circular shape or a kidney shape. Preferably, incisions to implant an implant strip constructed of shape-memory material may be smaller because the implant strip may assume a second shape without assistance from a surgeon.

It is also possible that an implant strip constructed of a shape-memory material may expand in size following implantation. Preferably, this may allow an implant strip to be constructed with a smaller size than necessary. With this arrangement, an implant strip may be constructed with a first size. Following implantation, the implant strip may expand to a second size that is larger than the first size. In this manner, smaller incisions may be made to implant the implant strip. This can provide reduced trauma and faster healing rates following implantation of an implant strip constructed of shape-memory material.

While various embodiments of the invention have been described, the description is intended to be exemplary, rather than limiting, and it will be apparent to those of ordinary skill in the art that many more embodiments and implementations are possible that are within the scope of the invention. Accordingly, the invention is not to be restricted except in light of the attached claims and their equivalents. Also, various modifications and changes may be made within the scope of the attached claims.

What is claimed is:

1. A method for implanting a spinal prosthesis comprising:
 making an incision in a patient;
 inserting the spinal prosthesis in an uncoiled state through the incision and into a space between adjacent vertebrae,
 wherein the spinal prosthesis comprises an implant strip and a separating strip,
 wherein the implant strip extends in a longitudinal direction,
 wherein the implant strip has a first lateral edge and a second lateral edge opposite to the first lateral edge,
 wherein the implant strip is made of a shape-memory material that coils the implant strip into a coiled state in the space between the adjacent vertebrae,
 wherein the implant strip includes a first surface between the first lateral edge and the second lateral edge, and a second surface opposite to the first surface and between the first lateral edge and the second lateral edge, and
 wherein the separating strip is disposed against the first surface of the implant strip;
 coiling the implant strip in the space between the adjacent vertebrae, wherein the separating strip covers less than an area of the first surface of the implant strip so as to provide gaps between coils of the first lateral edge of the implant strip when the implant strip is in the coiled state; and
 positioning the coils of the first lateral edge of the implant strip against a first vertebra of the adjacent vertebrae to facilitate bone growth into the gaps between the coils of the first lateral edge of the implant strip.

2. The method according to claim 1, further comprising applying a bone growth promoting agent in the gaps between the coils of the first lateral edge of the implant strip.

3. The method according to claim 2, wherein applying the bone growth promoting agent comprises applying the bone growth promoting agent in a sponge application and/or applying the bone growth promoting agent as a paste.

4. The method according to claim 1, wherein the spinal prosthesis further comprises a bone growth promoting agent disposed in the gaps between the coils of the first lateral edge of the implant strip.

5. The method according to claim 1, wherein the first lateral edge of the implant strip forms an inclined surface across a width of the spinal prosthesis when the implant strip is in the coiled state, and
 wherein the method further comprises positioning the inclined surface so as to fit a natural contour of the first vertebra of the adjacent vertebrae.

6. The method according to claim 5, further comprising positioning the inclined surface to correct scoliosis and/or spondylolisthesis.

7. The method according to claim 5, further comprising positioning the inclined surface to provide lordosis to a vertebral column.

8. The method according to claim 1, wherein the shape-memory material is a metal.

9. The method according to claim 1, wherein inserting the spinal prosthesis in the uncoiled state through the incision and into the space between adjacent vertebrae comprises inserting a tube into the incision and inserting the spinal prosthesis through the tube, which holds the spinal prosthesis in a generally linear shape.

10. A method for implanting a spinal prosthesis comprising:
 making an incision in a patient;
 inserting the spinal prosthesis in an uncoiled state through the incision and between a first vertebra and a second vertebra,
 wherein the spinal prosthesis comprises an implant strip and a continuous separating portion,
 wherein the implant strip is elongated in a longitudinal direction and is made of a shape-memory material that biases the implant strip toward a coiled state,
 wherein the implant strip extends in a lateral direction from a first lateral side portion to a second lateral side portion,
 wherein the implant strip includes a first surface between the first lateral side portion and the second lateral side portion, and a second surface opposite to the first surface and between the first lateral side portion and the second lateral side portion, and
 wherein the separating portion is disposed at the first surface of the implant strip;
 coiling the implant strip between the first vertebra and the second vertebra, such that the implant strip forms a first inner coil and a second outer coil that coils around the first inner coil, the separating portion is disposed between the first inner coil and the second outer coil, and the separating portion covers less than an area of the first surface of the implant strip so as to provide gaps between the first inner coil and the second outer coil at the first lateral side portion of the implant strip; and
 positioning the spinal prosthesis between the first vertebra and the second vertebra so that the first lateral side portion of the implant strip engages the first vertebra to facilitate bone growth into the gaps at the first lateral side portion of the implant strip.

11. The method according to claim 10, further comprising:
 coiling the implant strip between the first vertebra and the second vertebra such that gaps are provided between the first inner coil and the second outer coil at the second lateral side portion of the implant strip; and
 positioning the spinal prosthesis between the first vertebra and the second vertebra so that the second lateral side portion of the implant strip engages the second vertebra to facilitate bone growth into the gaps at the second lateral side portion of the implant strip.

12. The method according to claim 11, further comprising applying a bone growth promoting agent in the gaps at the first lateral side portion of the implant strip and in the gaps at the second lateral side portion of the implant strip.

13. The method according to claim 10, further comprising applying a bone growth promoting agent in the gaps at the first lateral side portion of the implant strip.

14. The method according to claim 10, wherein the spinal prosthesis further comprises a bone growth promoting agent disposed in the gaps at the first lateral side portion of the implant strip.

15. The method according to claim 10, wherein the first lateral side portion of the implant strip forms an inclined surface across a width of the spinal prosthesis when the implant strip is in the coiled state, and
 wherein the method further comprises positioning the inclined surface so as to fit a natural contour of the first vertebra of the adjacent vertebrae.

16. The method according to claim 10, wherein the implant strip is made of metal and the separating portion is made of a polymer.

17. The method according to claim 10, wherein inserting the spinal prosthesis in the uncoiled state through the incision and between the first vertebra and the second vertebra comprises inserting a tube into the incision and inserting the spinal prosthesis through the tube, which holds the spinal prosthesis in a generally linear shape.

18. A method for implanting a spinal prosthesis comprising:
- making an incision in a patient;
- inserting an implant strip in an uncoiled state through the incision and between adjacent vertebrae,
- wherein the implant strip is made of a shape-memory material that biases the implant strip to coil into a coiled state,
- wherein the implant strip extends in a longitudinal direction,
- wherein the implant strip has a first lateral edge and a second lateral edge opposite to the first lateral edge,
- wherein the first lateral edge of the implant strip forms an inclined surface across a width of the spinal prosthesis when the implant strip is in the coiled state,
- wherein the implant strip includes a first surface between the first lateral edge and the second lateral edge, and a second surface opposite to the first surface and between the first lateral edge and the second lateral edge,
- wherein the spinal prosthesis further comprises a separating portion disposed against the first surface of the implant strip, and
- wherein the separating portion covers less than an area of the first surface of the implant strip so as to provide gaps between coils of the first lateral edge of the implant strip when the implant strip is in the coiled state;
- coiling the implant strip between the adjacent vertebrae; and
- positioning the inclined surface of the coiled implant strip so as to fit a natural contour of a first vertebra of the adjacent vertebrae.

19. The method according to claim 18, further comprising positioning the coils of the first lateral edge of the implant strip against the first vertebra of the adjacent vertebrae to facilitate bone growth into the gaps between the coils of the first lateral edge of the implant strip.

20. The method according to claim 19, further comprising applying a bone growth promoting agent in the gaps between the coils of the first lateral edge of the implant strip.

* * * * *